(12) United States Patent
Andrus et al.

(10) Patent No.: US 8,841,477 B2
(45) Date of Patent: Sep. 23, 2014

(54) SIRTUIN ACTIVATING COMPOUNDS AND PROCESSES FOR MAKING THE SAME

(75) Inventors: Merritt B. Andrus, Lindon, UT (US); Jing Liu, Provo, UT (US)

(73) Assignee: Brigham Young University, Provo, UT (US)

( * ) Notice: Subject to any disclaimer, the term of this patent is extended or adjusted under 35 U.S.C. 154(b) by 1440 days.

(21) Appl. No.: 12/503,239

(22) Filed: Jul. 15, 2009

(65) Prior Publication Data

US 2010/0185006 A1    Jul. 22, 2010

Related U.S. Application Data

(63) Continuation of application No. 10/597,335, filed as application No. PCT/US2005/002229 on Jan. 19, 2005, now Pat. No. 7,714,161.

(60) Provisional application No. 60/537,622, filed on Jan. 20, 2004, provisional application No. 60/616,537, filed on Oct. 6, 2004.

(51) Int. Cl.
| | | |
|---|---|---|
| C07C 69/88 | (2006.01) | |
| C07C 67/29 | (2006.01) | |
| C07C 69/017 | (2006.01) | |
| C07C 67/287 | (2006.01) | |
| C07C 67/293 | (2006.01) | |
| C07C 67/08 | (2006.01) | |
| C07C 67/14 | (2006.01) | |

(52) U.S. Cl.
CPC .............. *C07C 69/017* (2013.01); *C07C 67/29* (2013.01); *C07C 67/287* (2013.01); *C07C 67/293* (2013.01); *C07C 67/08* (2013.01); *C07C 67/14* (2013.01)
USPC .......................................................... 560/70

(58) Field of Classification Search
None
See application file for complete search history.

(56) References Cited

U.S. PATENT DOCUMENTS

| | | | |
|---|---|---|---|
| 5,214,168 A | 5/1993 | Zajacek et al. | |
| 5,360,924 A | 11/1994 | Beller et al. | |
| 5,827,898 A | 10/1998 | Khandwala et al. | |
| 6,008,260 A | 12/1999 | Pezzuto et al. | |
| 6,022,901 A | 2/2000 | Goodman | |
| 6,124,364 A | 9/2000 | Breton et al. | |
| 6,211,247 B1 | 4/2001 | Goodman | |
| 6,270,780 B1 | 8/2001 | Carson et al. | |
| 6,333,441 B1 | 12/2001 | Sato et al. | |
| 6,414,037 B1 | 7/2002 | Pezzuto et al. | |
| 6,552,213 B1 | 4/2003 | Deshpande et al. | |
| 6,572,882 B1 | 6/2003 | Vercauteren et al. | |
| 6,790,869 B2 | 9/2004 | Ghai et al. | |
| 6,878,751 B1 | 4/2005 | Donnelly et al. | |
| 6,974,895 B1 | 12/2005 | Paiva et al. | |
| 7,026,518 B2 | 4/2006 | Gokaraju et al. | |
| 7,037,945 B2 | 5/2006 | Docherty | |
| 7,145,025 B2 | 12/2006 | Lockwood et al. | |
| 7,544,497 B2 | 6/2009 | Sinclair et al. | |
| 2003/0118617 A1 | 6/2003 | Soby et al. | |
| 2005/0059733 A1 | 3/2005 | Chen et al. | |
| 2005/0096256 A1 | 5/2005 | Sinclair | |
| 2005/0171027 A1 | 8/2005 | Sinclair et al. | |
| 2006/0014705 A1 | 1/2006 | Howitz et al. | |
| 2006/0025337 A1 | 2/2006 | Sinclair et al. | |
| 2006/0084135 A1 | 4/2006 | Howitz et al. | |
| 2006/0111435 A1 | 5/2006 | Sinclair et al. | |
| 2006/0205792 A1 | 9/2006 | Wong et al. | |
| 2006/0229265 A1 | 10/2006 | Milburn et al. | |
| 2006/0276393 A1 | 12/2006 | Milburn et al. | |

(Continued)

FOREIGN PATENT DOCUMENTS

| | | |
|---|---|---|
| CA | 2 452 159 A1 | 2/2003 |
| CA | 2 581 201 A1 | 4/2006 |

(Continued)

OTHER PUBLICATIONS

Andrus, Merritt et al. Tet. Let. 44 (2003) 4819-4822.*
Andrus, Merritt B., et al., "Synthesis of resveratrol using a direct decarbonylative Heck approach from resorcylic acid," 44 *Tetrahedron Letters* 4819-4822 (2003).
Andrus, M.B., et al. "Synthesis of polyhydroxylated ester analogs of the stilbene resveratrol using decarbonylative Heck couplings". *Tetrahedron Letters*. 2006. 47(32). 5811-5814.

(Continued)

*Primary Examiner* — Clinton Brooks
(74) *Attorney, Agent, or Firm* — Brinks Gilson & Lione; Ryan L. Marshall

(57) ABSTRACT

The present invention includes methods for preparing resveratrol, resveratrol esters and substituted and unsubstituted stilbenes of the formula given below; where each Y is —O or halogen, each Z is —O or halogen, each n and each m is independently the value of 0, 1, 2, 3, 4 or 5, each A and each B is independently selected from $P_n$, R or absent, each V and each W is independently selected from $P_n$, straight or branched alkyl of from 2 to 6 carbon atoms and cycloalkyl of from 3 to 8 carbon atoms, alkoxy, phenyl, benzyl or halogen, R is independently selected from the group comprising alkyl with at least one carbon atom, aryl and aralkyl, $P_n$ is an alcohol protecting group and diastereoisomers of the foregoing. The compounds are made from a multi-step process including a N-heterocyclic carbene-type ligand coupling in the presence of a base with benzyol halide and styrene coupling partners. These compounds show increased stability for use in the food, cosmetic and pharmaceutical industries.

(I)

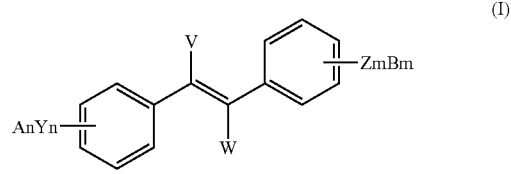

27 Claims, No Drawings

(56) References Cited

U.S. PATENT DOCUMENTS

| | | | |
|---|---|---|---|
| 2006/0276416 | A1 | 12/2006 | Sinclair et al. |
| 2006/0292099 | A1 | 12/2006 | Milburn et al. |
| 2007/0014833 | A1 | 1/2007 | Milburn et al. |
| 2007/0149466 | A1 | 6/2007 | Milburn et al. |
| 2007/0197819 | A1 | 8/2007 | Haerter et al. |
| 2007/0276172 | A1 | 11/2007 | Sinha et al. |
| 2008/0255382 | A1 | 10/2008 | Andrus et al. |
| 2009/0012130 | A1 | 1/2009 | Wolberger et al. |
| 2009/0076114 | A1 | 3/2009 | Kang et al. |

FOREIGN PATENT DOCUMENTS

| | | | |
|---|---|---|---|
| CN | 101264069 | | 9/2008 |
| CN | 101343214 | | 1/2009 |
| DE | 100 15 525 | A1 | 10/2001 |
| EP | 0 587 050 | B1 | 3/1994 |
| EP | 1 336 602 | | 8/2003 |
| FR | 2 816 843 | A1 | 5/2002 |
| FR | 2 887 251 | A1 | 12/2006 |
| JP | 54-070249 | A | 6/1979 |
| JP | 7 053 359 | A | 2/1995 |
| JP | 08175960 | | 7/1996 |
| JP | 9-241617 | | 9/1997 |
| JP | 2001-048904 | A | 2/2001 |
| WO | WO 97/07790 | A1 | 3/1997 |
| WO | WO 99/03816 | A1 | 1/1999 |
| WO | WO 01/60774 | A1 | 8/2001 |
| WO | WO 2004/000302 | A1 | 12/2003 |
| WO | WO 2004/006881 | A2 | 1/2004 |
| WO | WO 2004/011423 | | 2/2004 |
| WO | WO 2005/069998 | A2 | 8/2005 |
| WO | WO 2005/102298 | A1 | 11/2005 |
| WO | WO 2006/024099 | A1 | 3/2006 |
| WO | WO 2007/104867 | A2 | 9/2007 |
| WO | WO 2008/012108 | A2 | 1/2008 |
| WO | WO 2008/150093 | A2 | 12/2008 |
| WO | WO 2009/012551 | A1 | 1/2009 |
| WO | WO 2009/126700 | A1 | 10/2009 |
| WO | WO 2009/128050 | A2 | 10/2009 |

OTHER PUBLICATIONS

Angeloni, A., et al. Liquid crystalline poly(β-aminoester)s containing different mesogenic groups. *Makromolekulare Chemie*. 1985. 186(5). 977-997.

Ashok, D.; et al. "Roxburghin—a new stilbene from the wood of Cassia roxburghii". *Journal of the Indian Chemical Society*. 1987. 64(9). 559-61.

Betts, W.D. "Fluidized-bed production of phthalic anhydride." *Ind. Chemist*. 1963. 39(6;7;8). 302-308;370-378;411-416.

Billard, C.; et al. "The inducible NO synthase is down-regulated during apoptosis of malignant cells from B-cell chronic lymphocytic leukemia induced by flavopiridol and polyphenols". *Annals of the New York Academy of Sciences*. 2003. 1010(Apoptosis). 381-383.

Castagnino Chantal, et al., "Stabilized resveratrol derivatives," 2$^{nd}$ *International Electronic Conference on Synthetic Organic Chemistry* (ECSOC-2), http://www.mdpi.org/ecxoc/, Sep. 1-30, 1998, 2 pages (Aug. 2, 2004).

Castedo, L., et al. "Selective reductive carbonyl couplings with titanium." *Journal of Organic Chemistry*. 1981. 46(21), 4292-4294.

Cardile, Venera, et al., "Chemo-enzymatic synthesis and cell-growth inhibition activity of resveratrol analogues," *Bioorganic Chemistry* 33:22-33 (2005).

Chang, S.; et al. "A short and efficient synthetic approach to hydroxyl (E)-stilbenoids via solid-phase cross metathesis". *Tetrahedron Letters*. 2002. 43(41). 7445-7448.

Cunningham, J.; et al. "The constitution of piceatannol". *Journal of the Chemical Society*. 1963. 2875-83.

Derrida, M., "Resveratrol—The chemistry and biosynthesis of resveratrol," *GDOA Discussion Board*, http://www.gdoa.com/_disc3/00000088.htm, 2 pages (Jan. 16, 2004).

DeTar, D. F.; et al. "Intramolecular reactions. V. Factors affecting the yield on diazonium cyclization reactions". *Journal of the American Chemical Society*. 1957. 79. 2498-502.

Ding, N.; et al. "Study on the synthesis of (E)-3-methoxy-4,4'-dihydroxystilbene by Heck reaction". *Youji Hauxue*. 2004. 24(8). 898-901.

Drewes, S.E.; et al. "Polyhydroxystilbenes from the heartwood of Schotia brachypetala". *Journal of the Chemical Society*. 1974. 9. 961-2.

Engler, et al., "Lewis Acid-Promoted Reactions of Unsymmetrically Substituted Stilbenes with 2-Methoxy-1,4-benzoquinones: Stereoselective Synthesis of trans-2,3-Diaryl-2,3-dihydrobenzofurans," *Journal of Organic Chemistry*. 1995. 60(12). 3700-3706.

Farina, A.; et al. "An improved synthesis of resveratrol". *Natural Product Research, Part A: Structure and Synthesis*. 2006. 20(3). 247-252.

Farina, A.; et al. "Synthesis of hydroxystilbenes and their derivatives via Heck reaction". *Natural Product Research*. 2007. 21(6). 564-573.

Finkel, Tornen, "A toast to long life," 425 *Nature* 132-133 (Sep. 11, 2003).

Franzén, Robert, "The Suzuki, the Heck, and the Stille reaction—three versatile methods for the introduction of new C—C bonds on solid support," 78 *Can. J. Chem*. 957-962 (2000).

Funaoka, K.; et al. "Flavonoids of Zelkova serrata wood. VIII". *Mokuzai Gakkaishi*. 1957. 3. 218-24.

Gierer, J.; et al. "Lignin chromophores. Part III. Syntheses of hydroxyl- and alkoxystilbenes via aryl migration". *Journal of Wood Chemistry and Technology*. 1991. 11(2). 171-93.

Gorham, John. "Effect of lunularic acid analogs on liverwort growth and IAA oxidation." *Phytochemistry (Elsevier)*. 1978. 17(1), 99-105.

Gotoh, T.; et al. "TFT-addressed cholesteric liquid crystal projection display". *NEC Research & Development*. 1997. 38(4). 394-404.

Gromova. A.S.; et al. "Stilbenes from the bark of some Pinaceae species". *Koksnes Kimija*. 1979. (3). 103-9.

Guiso, Marcella, "A new efficient resveratrol synthesis," 43 *Tetrahedron Letters* 597-598 (2002).

Hashimoto, T.; et al. "A highly efficient preparation of lunularic acid and some biological activities of stilbene and dihydrostilbene derivatives". *Phytochemistry*. 1988. 27(1). 109-13.

Hata, K.; et al. "Chemical studies on the heartwood of Cassia garrettiana Craib. II. Nonanthraquinonic constituents". *Chemical & Pharmaceutical Bulletin*. 1979. 27(4). 984-9.

Hermann, et al., Chelating N-heterocyclic Carbene Ligands in Palladium-Catalyzed Heck-Type Reactions, 557 *J. of Organometallic Chemistry* 93-96 (1998).

Hillis, W.E.; et al. "Chromatorgraphic and spectral properties of stilbene derivatives". *Journal of Chromatography*. 1968. 32(2). 323-36.

Howitz, Konrad T., et al., "Small molecule activators of sirtuins extend Saccharomyces cerevisiae lifespan," 425 *Nature* 191-196 (Sep. 2003).

Inamori, Y.; et al. "Physiological activities of 3,3',4,5'-tetrahydroxystilbene isolated from the heartwood of Cassia garrettiana Craib". *Chemical & Pharmaceutical Bulletin*. 1984. 32(1). 213-18.

Inamori, Y.; et al. "The coronary vasodilatory and hypotensive effects of 3,3',4,5'-tetrahydroxystilbene and its derivatives". *Yakugaku Zasshi*. 1984. 104(7). 819-21.

Ito, M., et al. "Vibrational spectra of resonance-stabilized anions (CnOn)2-." *Proc. Intern. Symp. Mol. Struct. Spectryl*, Tokyo. 1962. (A214). 4 pp.

Johnson, W., et al. "2,8-Dihydroxy-5,6,11,12-tetrahydrochrysene." *Journal of the American Chemical Society*. 1952. 74. 2251-2253.

Kimura, Y.; et al. "Inhibitory effects of active substances isolated from Cassia garrettiana heartwood on tumor growth and lung metastasis in Lewis lung carcinoma-bearing mice. Part 2". *Anticancer Research*. 2000. 20(5A). 2923-2930.

King, F.E.; et al. "Chemistry of extractives from hardwoods. XXVIII. The occurrence of 3,3',4,5'-tetrahydroxy- and 3,3',4,5,5'-pentahydroxystilbene in Vouacapoua species". *Journal of Chemical Society*. 1956. 4477-80.

Kondo, T.; et al. "Wood extractives. V. Heartwood components of Platycarya strobilacea". *Nippon Nogei Kagu Kaishi*. 1956. 30. 281-3.

(56) References Cited

OTHER PUBLICATIONS

Kubota, T.; et al. "New description of the substituent effect on electronic spectra by means of substituent constants. III. Charge transfer spectra of EDA complexes". *Molecular Crystals and Liquid Crystals*. 1985. 126(1). 111-20.

Kunimoto, H. "Infrared absorption of cis-stilbene and its 4,4'-disubstituted derivatives." *Proc. Intern. Symp. Mol. Struct. Spectry.*, Tokyo. 1962. (A219). 4 pp.

Kunimoto, H. "Preparation of stilbenes and $\alpha,\alpha'$-dideuterio derivatives." *Nippon Kagaku Zasshi*. 1963. 84(1). 65-68.

Laidlaw, R.A.; et al. "Heartwood extractives of some timbers of the family *Moraceae*". *Chemistry & Industry* (London, United Kingdom). 1959. 1604-5.

Lapkin, I., et al. "Organoberyllium compounds and their chemical transformations. VII. Reaction of haloberyllium acyls with aromatic aldehydes." *Zhurnal Obshchei Khimii*. 1973. 43(9). 1984-1986.

le Noble, W.J. "The effect of pressure on the homogenous alkylation of phenoxide ion". *Journal of the American Chemical Society*. 1963. 85. 1470-2.

Learmonth, D.A. "A Concise Synthesis of the 3-O-β-D- and 4'-O-β-D-Glucuronide Conjugates of trans-Resveratrol". *Bioconjugate Chemistry*. 2003. 14(1). 262-267.

Ma, Yudao, et al., "Sonogashira Coupling Using Bulky Palladium-Phenanthryl Imidazolium Carbene Catalysis," 5(18) *Organic Letters* 3317-3319 (2003).

Majumder, P.L.; et al. "Thunalbene, a stilbene derivative from the orchid *Thunia alba*". *Phytochemistry*. 1998. 49(8). 2375-2378.

Matsuo, T., et al. "Charge-transfer complexes. V. Complexes of tetracyanoethylene with trans-stilbene and related compounds." *Bulletin of the Chemical Society of Japan*. 1968. 41(2). 271-274.

Mongolsuk, S.; et al. "2,3',4,5'-Tetrahydroxystilbene from *Artocarpus lakoocha*". *Journal of the Chemical Society*. 1957. 2231-3.

Morgan, J.W.W.; et al. "The chemistry of color changes in wood. I. The Significance of stilbenes". *Holzforchung*. 1968. 22(1). 11-16.

Nicolosi, Giovanni, et al., "Chemo-enzymatic preparation of resveratrol derivatives," 16 *Journal of Molecular Catalysis B: Enzymatic* 223-229 (2002).

Nicotra, Silvia, et al., "Biotransformation of resveratrol: synthesis of trans-dehydrodimers catalyzed by laccases from *Myceliophthora thermophyla* and from *Trametes pubescens*," *Tetrahedron* 60:595-600 (2004).

Nomura, Eisaku, et al., "Synthesis and Conformational Property of Tannin-like p-tert-Butylcalix[4]arene 1,3-Diesters Stabilized by Intramolecular Hydrogen Bonds," *Chemical Abstracts*, XP-002458152, retrieved from STN, Database accession No. 2001:795467, 1 page. (2001).

Nonomura, Susumu, et al., "Chemical constituents of polygonaceous plants. I. Components of *Polygonum cuspidatum*," *Chemical Abstracts*, XP-002058089, retrieved from STN, Database accession No. 1964:23690, 1 page (1964).

Oki, M., et al. "The characteristic infrared absorption bands of cis-stilbene and its para,para'-disubstituted derivatives." *Spectrochimica Acta*. 1963. 19(9). 1463-1471.

Petralia, Salvatore, et al., "Hydrogen atom abstraction from resveratrol and two lipophilic derivatives by *tert*-butoxyl radicals. A laser flash photolysis study," XP-002458151, *New Journal of Chemistry* 28(12):1484-1487 (2004).

Reimann, E. et al. "Natural stilbenes. II. Synthesis of polyhydroxystilbenes". *Justus Liebigs Annalen der Chemie*. 1971. 750. 109-27.

Ryu, S.Y.; et al. "Monoamine oxidase—A inhibitors from medicinal plants". *Archives of Pharmacal Research*. 1988. 11(3). 230-9.

Sauvage, X.; et al. "Homobimetallic ruthenium-N-heterocyclic carbine complexes: synthesis, characterization, and catalytic applications". *Advanced Synthesis & Catalysis*. 2007. 349(1-2). 255-265.

"SIRT1: A New Target for Cancer," 2(5) *Biomol Drug Discovery News* 1-4 (Jul. 17, 2003).

"SIRT1: A Promising Target for Age-related Diseases," 2(6) *Biomol Drug Discovery News* 1-4 (Oct. 3, 2003).

Sreeramulu, K.; et al. "Anthraquinone constituents of Cassia Montana heyne". *Indian Journal of Heterocyclic Chemistry*. 1999. 8(3). 233-236.

Strakowsky, N.A.; et al. "Addition of urea, thiourea, and iodine to the natural benzopyrones of *Ammi visnaga* and *Ammi majus*". *Egyptian Journal of Chemistry*. 1959. 2. 111-17.

Supplementary European Search Report from corresponding EP Application No. 05711939.8, dated Nov. 13, 2007 (4 pages).

Van Der Klashorst, G.H. "Low molecular mass lignin fragments present in industrial kraft pine spent liquor". *Holzforschung*. 1988. 42(1). 65-66.

Velder, J.; et al. "A simple access to biologically important trans-stilbenes via Ru-catalyzed cross metathesis". *Synthesis*. 2006. (2). 273-278.

Wade, Nicholas, "Life-Extending Chemical is Found in Certain Red Wines," http://sirtuins.com/life-extension.html, 7 pages (Jan. 16, 2004).

Weiss, Rick, "Scientists Find Way to Stimulate Anti-Aging Enzyme," http://sirtuins.com/index.html, 5 pages (Jan. 16, 2004).

"What is MDidea Transresveratrol: Basic Botanical Data and Product Data of Mdidea Transresveratrol," *Mdidea: Extracts Professional*, http://www.mdidea.com/products/herbextract/resveratrol/data.html, 8 pages (Jan. 16, 2004).

Xu, G.; et al. "Inhibition of protein kinase C by stilbenoids". *Yaoxue Xueba*. 1994. 29(11). 818-22.

Yang, D.; et al. "Significant Effects of Nonconjugated Remote Substituents in Catalytic Asymmetric Epoxidation". *Journal of the American Chemical Society*. 1998. 120(30), 7659-7660.

Zaman, A., et al. "Isolation and structure of gnetol, a novel stilbene from Gnetum ula." *Indian Journal of Chemistry, Section B: Organic Chemistry Including Medicinal Chemistry*. 1983. 22B(2). 101-104.

\* cited by examiner

SIRTUIN ACTIVATING COMPOUNDS AND PROCESSES FOR MAKING THE SAME

RELATED APPLICATIONS

This application is a continuation of U.S. patent application Ser. No. 10/597,335, filed Jul. 20, 2006, which is a national stage entry under 35 USC §371 of International Application No. PCT/US05/02229, filed Jan. 19, 2005, which claims the benefit under 35 U.S.C. §119(e) of U.S. Provisional Patent Application No. 60/616,537, filed Oct. 6, 2004, and of U.S. Provisional Patent Application No. 60/537,622, filed Jan. 20, 2004, the disclosures of which are incorporated, in their entirety, by this reference.

BACKGROUND

Technical Field

The present invention relates to compounds that activate sirtuin enzymes, and more particularly to analog compounds of resveratrol.

The sirtuins are a class of $NAD^+$-dependent protein deacetylase enzymes that regulate a wide variety of cellular activities that promote cell survival and extend lifespan in response to environmental stress. Sirtuins exert their effect by removing acetyl groups from certain target proteins in the presence of oxidized nicotinamide adenine dinucleotide ($NAD^+$). For example, the yeast sirtuin enzyme Sir2 (silent information regulator 2), originally identified for its role in silencing transcription of DNA, has also been shown to promote cell survival in response to caloric restriction. Similarly, in C. elegans, the sirtuin enzyme SIR-2.1 has been shown to extend lifespan. In mammalian cells, the sirtuin enzyme SIRT1 (a homolog of the yeast Sir2 and C. elegans SIR-2.1 enzymes) deacetylates the tumor suppressor p53 to promote cell survival. Sirtuins therefore appear to be activated as part of a beneficial cellular response to stress, resulting in cell survival and extended lifespan. Activators of sirtuins may therefore be beneficial in effecting fundamental cellular processes that protect cells from stress and prevent or treat age-related diseases, and lengthen healthy life.

Resveratrol (3,5,4'-trihydroxy-trans-stilbene) is a polyphenol compound, known to be the most potent activator of sirtuins. As a stilbene phytoalexin, resveratrol continues to receive increasing attention for its role in mitigation of numerous and diverse human pathological processes including inflammation, atherosclerosis, and carcinogenesis. Resveratrol is known for its activity as an antioxidant, cyclooxygenase inhibitor, lipid modifier, platelet aggregation inhibitor and vasodilator, inhibitor of tumor initiation, promotion and progression, neuroprotector, and antiviral compound.

Resveratrol is an especially abundant component of red wines produced from grapes grown in cooler climates where plants are under stress from heavy disease pressure. Indeed, the consumption of red wine containing resveratrol is believed to be responsible for the surprisingly normal lifespan of the French, despite their heavy consumption of fatty foods that cause heart disease, a phenomenon referred to as the "French Paradox." Resveratrol, however, is not an optimal sirtuin activator. Its practical use is also limited due to difficult isolation and stereo-selectively of extracts obtained from plant sources. More significantly, resveratrol is highly unstable due to its potential for oxidation, resulting in the formation of unstable radicals and quinones, and requiring that the final isolation of the product be carried out from impure mixtures containing multiple components.

Conventional methods of synthesizing resveratrol and resveratrol derivatives are expensive, inefficient, and do not provide for selective hydroxyl substitution. Many synthetic routes rely on Wittig and Horner-Emmons couplings that give mixtures of olefin isomers while still requiring 7-8 procedural steps. In addition, several conventional synthetic methods use methyl or benzyl ether protecting groups that require the use of boron tribromide or other inconvenient reagents for removal of those protecting groups.

In order to address the above problems, the present invention provides a novel and efficient route to synthetic resveratrol and novel derivative compounds of resveratrol having significantly improved activity and stability. Furthermore, the present invention provides a novel and efficient route to synthetic stilbene compounds.

BRIEF SUMMARY

The present invention provides novel stilbene compounds, in particular sirtuin activator compounds, and more particular ester analog compounds of resveratrol. These compounds have significantly improved biological activity and can be stored over a long period without alteration. The present invention also provides novel processes for synthesis of novel stilbene compounds, in particular novel sirtuin activator compounds, and more particular decarbonylative Heck couplings to synthesize stilbene derivatives. The present invention also provides an optional stilbene olefin isomerization procedure.

The instant invention is a compound of Formula I where each Y and each Z is independently selected from —O (ethers), —O—C═O, —C═O—O (esters), —O—C═O—O (carbonates), —O—C═O—NH, —O—C═O—NR, —NH—C═O—O, —NR—C═O—O (carbamates), —NH—C═O, —NR—C═O, —C═O—NH, —C═O—NR (primary and secondary amides)-NH, —NR (primary and secondary amines), —N (heterocyclic rings), —S (thiol ethers), and halogen, each n and each m is independently the value of 0, 1, 2, 3, 4 or 5, where each A and each B is independently selected from H, R or absent, where each V and each W is independently selected from H, straight or branched alkyl of from 1 to 6 carbon atoms and cycloalkyl of from 3 to 8 carbon atoms, alkoxy, phenyl, benzyl or halogen, and where R is independently selected from the group comprising alkyl with at least one carbon atom, aryl and aralkyl, and includes diastereoisomers of the foregoing. In some embodiments R is alkyl with at least two carbon atoms. In some embodiments the sum of m and n is greater than or equal to one but less than nine. In other embodiments the sum of m and n is three or more but less than nine.

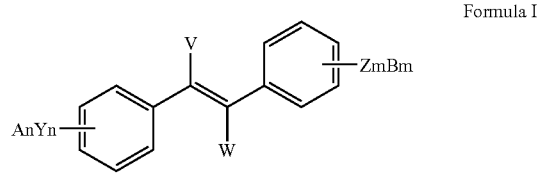

Formula I

Preferred compounds are those of Formula I wherein each Y and each Z is independently selected from —O, —O—C═O and halogen, each n and each m is independently the value of 0, 1, 2, 3, 4 or 5, and the sum of n and m is 1 or more, V and W are each H, each A and each B is independently selected from H, R or absent, and where R is independently selected from the group comprising alkyl with at least one carbon atom, aryl and aralkyl, and includes diastereoisomers of the foregoing. In some embodiments R is alkyl with at least two carbon atoms. In some embodiments the sum of m and n is greater than or equal to one but less than nine. In other embodiments the sum of m and n is three or more but less than nine.

In a particular embodiment, compounds of Formula 1B

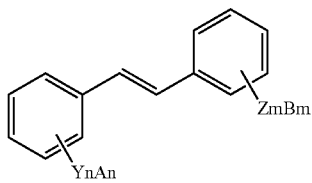

1B can be prepared where Y is independently selected from NH and O, n is equal to 0 1, 2, 3, 4 or 5, Z is independently selected from NH and O, m is equal to 0 1, 2, 3, 4 or 5, each A and each B is independently selected from R, $P_1$, $P_2$ and $P_3$ and each R is independently selected from alkyl with at least one carbon atom, aryl, aralkyl, and diastereoisomers of the foregoing and $P_1$, $P_2$ and $P_3$ are protecting groups, comprising the step of coupling a benzoyl halide compound of Formula 1B2

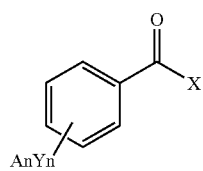

1B2 where X is halogen, with styrene compound of Formula 1B3

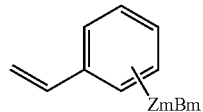

1B3 in solution or in suspension of a first solvent, transition metal catalyst, N-heterocyclic carbene-type ligand and a first base. In other embodiments, each R are independently selected from alkyl with at least two carbon atoms.

In another aspect of the invention, the resveratrol (3,5,4'-trihydroxy-trans-stilbene) esters of Formula II are characterized in that they comprise at least one ester group of formula —O—C=O—R at one or more of the 3, 5 and 4' positions, wherein R represents an alkyl with at least one carbon atom, aryl and aralkyl, and includes diastereoisomers of the foregoing. In some embodiments R is alkyl with at least two carbon atoms. In some embodiments the sum of m and n is greater than or equal to one but less than nine. In other embodiments the sum of m and n is three or more but less than nine.

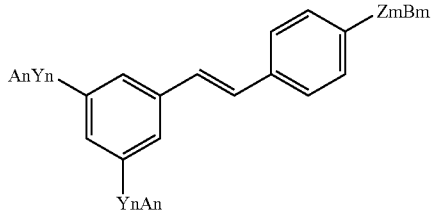

Formula II

In a particular embodiment, compounds of Formula 1A3

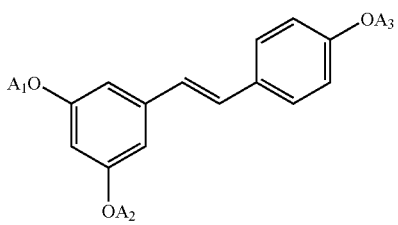

1A3 can be prepared where $A_1$ is selected from $P_1$ and $(CO)R_1$; $A_2$ is selected from $P_2$ and $(CO)R_2$; $A_3$ is selected from $P_3$ and $(CO)R_3$; where $P_1$ when present is a first alcohol protecting group, $P_2$ when present is a second alcohol protecting group, $P_3$ when present is a third alcohol protecting group, $R_1$, $R_2$ and $R_3$ when present are each independently selected from alkyl with at least one carbon atom, aryl, aralkyl, and diastereoisomers of the foregoing, comprising the step of coupling a benzoyl halide compound of Formula 1A4

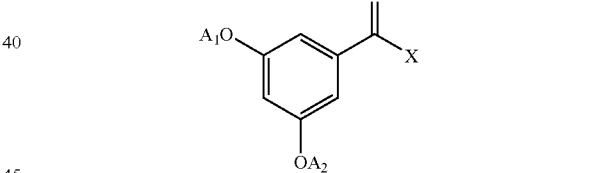

1A4 where X is halogen, with a 4-substituted styrene compound of Formula 1A5

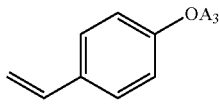

1A5 in solution or in suspension of a first solvent, transition metal catalyst, N-heterocyclic carbene-type ligand and a first base. In other embodiments, $R_1$, $R_2$ and $R_3$ when present are each independently selected from alkyl with at least two carbon atoms.

In some embodiments, R represents a saturated or unsaturated fatty acid group or radical. In the case of an unsaturated fatty acid, the double bonds are advantageously cis, which corresponds to the most frequent case found in the natural products. With products obtained more particularly by synthesis or hemisynthesis, the bonds are trans. Fatty acid derivatives which are suitable for the implementation of the invention include but are not limited to: butyric C4:O; valeric, C'5:O hexanoic, C6:O: sorbic, C6:2(n-2); lauric C12:O; palmitic C16:O; stearic, C18:O; oleic, C18:1(n-9) linoleic, C18:2(n-6); linolenic, C18:3(n-6); .alpha. linolenic, C18:3(n-3); arachidonic, C20:4(n-3) eicosapentaenoic C20:5(n-3); and docosahexanoic. C22:6(n-3). The C16 and more fatty acids are particularly appropriate as regards cosmetic uses. These fatty acids are extracted, for example, from microalgae.

In another embodiment, R represents an aryl group, the aryl group being more particularly phenyl, benzyl or styryl.

In yet another embodiment, R represents an aralkyl or aralkylene group, the alkyl or alkylene group being more particularly $C_1$ to $C_8$, in particular $C_1$ to $C_4$. In particular the aryl portion is phenyl, benzyl or styryl group.

In still another aspect of the invention, an improved process for the preparation of compounds of Formulas I and II involves a decarbonylative coupling of compounds of Formula 1C and Formula 1E in solution or in suspension of a solvent, transition metal catalyst, N-heterocyclic carbene-type ligand and base, where X is halogen, and each A and each B is independently selected from a protecting group and alkyl with at least one carbon atom, aryl and aralkyl, or absent when A or B is halogen.

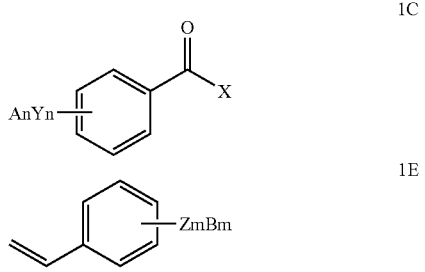

In yet another aspect of the invention, an improved process for the preparation of resveratrol arises from the 1) acetoxylation of 3,5-dihydroxy benzoic acid with an acetoxy esterification agent in solution with a base; 2) halogenation in solution; 3) reaction with an acetoxy styrene in solution, transition metal catalyst, N-heterocyclic carbene-type ligand, and base; and, 4) hydrolysis in solution with an alkali metal hydroxide.

In another aspect of the invention, novel benzoic acid derivatives of Formula 1C are characterized in that each Y is independently selected from —O, —O—C=O, A is H or R, n is equal to the value of 0, 1, 2, 3, 4 or 5, X is any halogen, and R is independently selected from the group comprising alkyl with at least one carbon atom, aryl, and aralkyl. In some embodiments R is alkyl with at least two carbon atoms. In some embodiments the sum of m and n is greater than or equal to one but less than nine. In other embodiments the sum of m and n is three or more but less than nine.

In still another aspect of the invention, a novel process for preparing derivatives of benzoic acid halides of the Formula 1C are characterized in that said compounds are halogenated with a halogenating agent in a solvent and benzotriazole. Preferred halogenating agents are thionyl chloride and oxalyl chloride.

In yet another aspect of the invention, preferred compounds of Formula 1C are those where X is Cl.

In another aspect of the processes of the invention, the base used in the step for coupling an acid chloride with a styrene derivative is a non-coordinating amine base. Preferred non-coordinating amine bases are selected from the group comprising: N,N-dimethylbenzylamine, N-methylmorpholine, dimethylaminopyridine. A more preferred non-coordinating amine base is N,N-dimethylbenzylamine.

In another aspect of the invention, an N-heterocyclic carbene-type ligand is employed in a decarbonylative Heck reaction. Preferred N-heterocyclic carbene-type ligands are selected from imidazolium, 1,3-disubstituted imidazolium (N,N'-bis-substituted imidazolium), 1,3-disubstituted-4,5-dihydroimidazolium carbene-type ligands. More preferred N-heterocyclic carbene-type ligands are those selected from N,N'-bis-carbocycle imidazolium ligands. Even more preferred N-heterocyclic carbene-type ligands are those selected from N,N'-bis-(2,6-diisopropylphenyl)imidazolium chloride, N,N'-bis-(dimesityl)imidazolium chloride, N,N'-bis-adamantylimidazolium chloride.

In still another aspect of the invention, a halogenating agent is used. Preferred halogenating agents are selected from the group comprising: thionyl chloride, thionyl bromide, thionyl iodide, oxalyl chloride, oxalyl bromide, oxalyl iodide, $PCl_3$, $PBr_3$, $PI_3$, $POCl_3$, $POBr_3$, and $POI_3$. More preferred halogenating agents are thionyl chloride and oxalyl chloride.

In another aspect of the invention, an acylating agent is used. Preferred acylating agents are selected from the group comprising: ester anhydrides, mixed ester anhydrides, acid halides. A more preferred acylating agent is acetic anhydride.

In yet another aspect of the invention a process includes the use of a protecting agent. Preferred protecting agents are those selected from the group comprising MOMCl, lev$_2$O, and chloroacetoxy chloride.

In another aspect of the invention, a hydrolysis step is performed using a reagent selected from alkaline earth hydroxides and alkoxides. Preferred hydrolysis reagents are lithium hydroxide, sodium hydroxide, potassium hydroxide, lithium methoxide, sodium methoxide, lithium methoxide, and lithium ethoxide.

In another aspect of the invention includes the use of a transition metal catalyst. Preferred transition metal catalysts are palladium, rhodium, and ruthenium catalysts. More preferred transition metal catalysts are palladium catalysts. Preferred palladium catalysts are selected from the group comprising: Pd(OAc)$_2$, PdCl$_2$, PdBr$_2$, palladium bis triphenylphosphine, and palladium tris triphenyl phosphine. A more preferred Pd II catalyst is Pd(OAc)$_2$.

In still another aspect of the invention, a deprotection reagent is used. Preferred deprotection agents are those selected from the group comprising: sodium sulfite and sodium thiosulfite, aqueous pyridine at pH 6.7, NaI and TMSCl, and alkaline earth metal hydroxide and a polar aprotic solvent.

In yet another aspect of the invention, pharmaceutical compositions of the compounds of Formulas I and II comprising a therapeutically effective amount of a compound of Formulas I and II in admixture with a pharmaceutically acceptable carrier are described.

In another aspect of the invention, cosmetic compositions of the compounds of Formula I and II comprising a cosmetically effective amount of a compound of Formula I and II in admixture with a cosmetically acceptable carrier are described.

In still another aspect of the invention, nutritional compositions of the compounds of Formula I and II comprising a nutritionally effective amount of a compound of Formula I and II in admixture with an nutritionally acceptable carrier are described.

The compounds Formula I and II are sirtuin activator compounds that interact with mammalian enzymes including SIRT1 promoting cell survival.

In still another aspect of the invention, levulinic halides and anhydrides are used to protect phenolic hydroxyls.

DETAILED DESCRIPTION OF THE DRAWINGS AND THE PRESENTLY PREFERRED EMBODIMENTS

In the compounds of Formulas I, II and 1-7 and as further used herein, the term "heteroatom" means nitrogen, oxygen, or sulfur. The term "halogen" as used herein means bromine, chlorine, fluorine, or iodine.

The term "cis" as used herein means the stereoisomerism about a carbon-carbon double bond, a monocyclic ring, a fused bicyclic ring, or a bridged bicyclic ring wherein the highest ranking substituent on each of the two carbons of relevance are on the same side, which substituent ranking is based on the sequence rules of the Cahn-Ingold-Prelog system (March, J., Advanced Organic Chemistry, $4^{th}$ ed., 1992, New York: John Wiley & Sons, 1992:109, 127-133 and references cited therein). The term "trans" means the stereoisomerism about a carbon-carbon double bond, a monocyclic ring, a fused bicyclic ring, or a bridged bicyclic ring wherein the highest ranking substituent on each of the two carbons of relevance are on opposite sides, which substituent ranking is based on the sequence rules of the Cahn-Ingold-Prelog system (March J., supra., 1992; 109:127-133 and references cited therein).

The term "alkyl" as used herein means a straight or branched hydrocarbon radical or group having at least one carbon atom including but not limited to saturated $C_1$-$C_6$ such as: methyl, ethyl, 1-propyl and 2-propyl, 1-butyl, 2-butyl, 2-methyl-1-propyl, 1,1-dimethylethyl, 1-pentyl, 2-pentyl, 3-pentyl, 2-methyl-1-butyl, 3-methyl-1-butyl, 2,2-dimethylpropyl, 1-hexyl, 2-hexyl, 3-hexyl, 2-methyl-1-pentyl, 3-methyl-1-pentyl, 4-methyl-1-pentyl, 3,3-dimethyl-1-butyl, 3,3-dimethyl-2-butyl, 2-ethyl-1-butyl and the like; $C_7$-$C_{12}$ such as: 1-heptyl, 2-heptyl, 3-heptyl, 4-heptyl, 2-methyl-1-hexyl, 4-methyl-1-hexyl, 5-methyl-1-hexyl, 1-octyl, 2-octyl, 3-octyl, 4-octyl, 6-methyl-1-heptyl, 5,5-dimethyl-1-hexyl, 2-ethyl-1-hexyl, 2-methyl-1-1-heptyl, 2-propyl-1-pentyl, 1-nonyl, 2-nonyl, 2-ethyl-2-methyl-1-hexyl, 4-methyl-1-octyl, 3,5,5-trimethyl-1-hexyl, 1-decyl, 2-decyl, 4-ethyl-1-octanyl, 2-methyl-1-nonyl, 4-methyl-1-nonyl, 8-methyl-1-nonyl, 1-undecyl (1-hendecyl), 2-undecyl, 7-methyl-1-decyl, 1-dodecyl, 5-dodecyl, 2-butyl-1-octyl, 10-methyl-1-undecyl and the like; $C_{13}$-$C_{18}$ such as: 1-tridecyl, 4-methyl-1-dodecyl, 11-methyl-1-dodecyl, 1-butyldecyl, 11-methyl-1-tridecyl, 1-pentadecyl, 1-hexadecyl, 2-hexyl-1-decyl, 1-heptadecyl, 14-methyl-1-hexadecyl, 15-methyl-1-hexadecyl, 1-octadecyl, 16-methyl 1-heptadecyl and the like; $C_{19}$-$C_{32}$ such as 1-nonadecyl, 2-methyl-1-octadecyl, 10-methyl-1-octadecyl, 17-methyl-1-octadecyl, 2,6,10,14-tetramethylpentadecyl, 1-eicosyl (1-arachidinyl, 1-leicosanyl), 18-methyl-1-nonadecyl, 1-heneicosyl, 19-methyl-1-eicosyl and 1-docosyl (1-behenyl), 1-tricosyl, 1-tetracosyl, 1-pentacosyl, 1-hexacosyl, 1-heptacosyl, 1-octacosyl, 1-nonacosyl, 1-triaconstyl, 2,6,10,15,19,23-hexamethyl-1-tetracosyl, 1-hentriaconsyl, 1-dotriacontyl and the like. Alkyl groups may be unsubstituted or substituted.

Alkyl groups having two or more carbons may optionally contain 1 or more sites of unsaturation, the groups being known as alkenyl groups or radicals and alkynyl groups or radicals. Alkenyl groups are analogous to alkyl groups which are saturated, but have at least one double bond (two adjacent $sp^2$ carbon atoms). Depending on the placement of a double bond and substituents, if any, the geometry of the double bond may be trans (E), or is (Z). Similarly, alkynyl groups have at least one triple bond (two adjacent sp carbon atoms). Unsaturated alkenyl or alkynyl groups may have one or more double or triple bonds, respectively, or a mixture thereof. Like alkyl groups, unsaturated groups may be straight chain or branched. Examples of alkenyls include vinyl, allyl, 2-methyl-2-propenyl, cis-2-butenyl, trans-2-butenyl, and acetyl, propene, 1-butene, 2-butene, 2-methylpropene, 1-pentene, 2-pentene, 2-methyl-1-butene, 2-methyl-2-butene, 3-methyl-1-butene, 1-hexene, 2-hexene, 3-hexene, 2,3-dimethyl-1-butene, 2,3-dimethyl-2-butene, 3,3-dimethyl-1-butene, 2-dimethyl-2-butene, 2-ethyl-1-butene, 2-methyl-1-pentene, 2-methyl-2-pentene, 3-methyl-1-pentene, 3-methyl-2-pentene, 4-methyl-1-pentene, 4-methyl-2-pentene, 1-heptene, 2-heptene, 3-heptene, 3,4-dimethyl-2-pentene, 4,4-dimethyl-2-pentene, 3-methyl-2-hexene, 3-methyl-3-hexene, 4-methyl-2-hexene, 2,3-dimethyl-1-pentene, 2,3-dimethyl-2-pentene, 2,4-dimethyl-1-pentene, 2,4-dimethyl-2-pentene, 3,3-dimethyl-1-pentene, 3,4-dimethyl-1-pentene, 4,4-dimethyl-1-pentene, 4,4-dimethyl-2-pentene, 3-ethyl-1-pentene, 3-ethyl-2-pentene, 2-methyl-1-hexene, 2-methyl-2-hexene, 3-methyl-1-hexene, 4-methyl-1-hexene, 5-methyl-1-hexene, 2,3,3-trimethyl-1-butene, 1-octene, 2-octene, 3-octene, 4-octene, 2,2-diemethyl-3-hexene, 2,3-dimethyl-2-hexene, 2,3-dimethyl-3-hexene, 3-ethyl-2-methyl-1-pentene, 3-ethyl-2-methyl-pent-2-ene, 2-isopropyl-1-pentene, 2-methyl-1-heptene, 2-methyl-2-heptene, 4-methyl-2-heptene, 2,3,4-trimethyl-2-pentene, 2,4,4-trimethyl-1-pentene, 2,4,4-trimethyl-2-pentene, 3,4,4-trimethyl-2-pentene, 1-nonene, 2-nonene, 3-nonene, 4-nonene, 2,2-dimethyl-3-heptene, 3,5,5-trimethyl-1-hexene, 1-decene, 4-decene, 5-decene, 3,7-dimethyl-1-octene, 2-methyl-1-nonene, 1-undecene, trisisobutylene, 2,2,4,6,6-pentamethyl-3-heptene, 1-dodecene, 2-methyl-1-undecene, 1-tridecene, 1,1-dineopentylethylene, 1-tetradecene, 7-tetradecene, 1-pentadecene, 1-hexadecene, 1-heptadecene, 8-heptadecene, 1-octadecene, 1-nonadecene, 1-eicosene, 9-heneicosene, 1-docosene and the like.

Examples of dialkenes include but are not limited to propandiene (allene), 1,3-butadiene, 1,3-pentadiene, 1,4-pentadiene, 2-methyl-1,3-butadiene (isoprene), 3-methyl-1,2-butadiene, 1,3-hexadiene, 1,4-hexadiene, 1,5-hexadiene, 2,4-hexadiene, 2,3-dimethyl-1,3-butadiene, 2-methyl-1,3-pentadiene, 2-methyl-1,4-pentadiene, 3-methyl-1,4-pentadiene, 4-methyl-1,3-pentadiene, 3-methyl-1,3-pentadiene 1-heptyne, 2-heptyne, 3-heptyne, 2,4-dimethyl-1,3-pentadiene, 2,4-dimethyl-2,3-pentadiene, 1,6-heptadiene, 1,7-octadiene, 1,4-octadiene, 3-methyl-1,5-heptadiene, 2,5-dimethyl-1,5-hexadiene, 2,5-dimethyl-1,4-hexadiene, 1,8-nonadiene, 7-methyl-1,6-octadiene 1,9-decadiene, 7-dimethyl-1,6-octadiene, 5,7-dimethyl-1,6-octadiene 1,7-hexadecadiene and the like.

Examples of trialkenes include but are not limited to 5-methyl-1,3,6-heptatriene, 2,6-dimethyl-2,4,6-octatriene (neoalloocimene), 1,5,9-decatriene, 2,6-dimethyl-2,4,6-octatriene, 3,7-dimethyl-1,3,6-octatriene, 7-methyl-3-methylene-1,6-octadiene, 3,7-dimethyl-1,3,6-octatriene, 1,4, 9-decatriene, 1,3,5-undecatriene and the like. Examples of alkynyls include, but are not limited to 1-butyne, 2-butyne, 1-pentyne, 2-pentyne, 4-methyl-pent-1-yne, 1-hexyne, 2-hexyne, 3-hexyne, 3,3-dimethyl-1-butyne, 1-heptyne, 2-heptyne, 3-heptyne, 5-methyl-1-hexyne, 1-octyne, 2-octyne, 3-octyne, 4-octyne, 1-nonyne, 1-decyne, 5-decyne and 1-dodecyne, 1-pentadecyne and the like. Alkenyl and Alkynl groups may be unsubstituted or substituted.

As used herein, alkyl also includes mixed alkenyl and alkynl groups. An unsaturated hydrocarbon may thus include subunits of double bonds and subunits of triple bonds. Examples of these mixed alkenyl and alkynl groups include 2-methyl-1-buten-3-yne, 2-methyl-1-hexen-3-yne and the like. Mixed alkenyl and alkynl groups may be unsubstituted or substituted.

Alkyl also includes groups having three or more carbons that contain 1 or more sites of unsaturation, that group being known as cycloalkyl groups or radicals.

The term "cycloalkyl" as used herein means a monocyclic or polycyclic hydrocarbyl group. Illustrative examples of a cycloalkyl group or radical include cyclopropyl, cycloheptyl, cyclooctyl, cyclodecyl, cyclobutyl, adamantyl, norpinanyl, decalinyl, norbornyl, cyclohexyl, and cyclopentyl. Cycloalkyl groups may be unsubstituted or substituted. Also included are rings in which 1 to 3 heteroatoms replace carbons. Such groups are termed "heterocyclyl", which means a cycloalkyl group also bearing at least one heteroatom selected from O, S, or N, examples being oxiranyl, pyrrolidinyl, piperidyl, tetrahydropyran, and morpholine.

The term "aryl" as used herein means an aromatic carbocyclic ring having from 6 to 14 carbon atoms. Illustrative examples of an aryl group or radical include phenyl, 1-naphthyl, 2-naphthyl, 1-anthryl, 2-anthryl, 9-anthryl, 1-phenanthryl, 2-phenanthryl, 3-phenanthryl, 4-phenanthryl, 5-phenanthryl, and the like; including fused ring systems with rings that have less than 6 carbons such as 1-acenaphthyl, 3-acenaphthyl, 4-acenaphthyl, 5-acenaphthyl, 1-azulyl, 2-azulyl, 4-azulyl, 5-azulyl, 6-azulyl and the like. Aryl groups may be unsubstituted or substituted.

The term "aryl" also includes heteroaryls. The term "heteroaryl" means an unsaturated monocyclic group or radical of 5 or 6 atoms, an unsaturated fused bicyclic group or radical of from 8 to 10 atoms, or an unsaturated fused tricyclic group or radical of from 11 to 14 atoms, the cyclic groups having 1 or 2 heteroatoms independently selected from O, N, or S. Illustrative examples of monocyclic heteroaryl include 2- or 3-thienyl, 2- or 3-furanyl, 1-, 2-, or 3-pyrrolyl, 1-, 2-, or 4-imidazolyl, 1-, 3-, or 4-pyrazolyl, 2-, 4-, or 5-oxazolyl, 2-, 4-, or 5-thiazolyl, 3-, 4-, or 5-isoxazolyl, 3-, 4-, or 5-isothiazolyl, 2-, 3-, or 4-pyridinyl, 3- or 4-pyridazinyl, 2- or 3-pyrazinyl, and 2-, 4-, or 5-pyrimidinyl. Illustrative examples of bicyclic heteroaryl include 2-, 3-, 4-, 5-, 6-, 7-, or 8-quinolinyl, 1-, 3-, 4-, 5-, 6-, 7-, or 8-isoquinolinyl, 1-, 2-, 3-, 4-, 5-, 6-, or 7-indolyl, 2-, 3-, 4-, 5-, 6-, or 7-benzo[b]thienyl, 2-, 4-, 5-, 6-, or 7-benzofuran, 2-, 4-, 5-, 6-, or 7-benzoxazolyl, 2-, 4-, 5-, 6-, or 7-benzothiazolyl, and 1-, 2-, 3-, 4-, 5-, 6-, or 7-benzimidazolyl. Illustrative examples of tricyclic heteroaryl include 1-, 2-, 3-, or 4-dibenzofuranyl, 1-, 2-, 3-, or 4-dibenzothienyl, and 1-, 2-, 3-, 4-, 5-, 6-, 7-, 8-, or 9-(1,2,3,4-tetrahydroacridinyl). Heteroaryl groups may be unsubstituted or substituted.

As used above, a fused bicyclic group or radical is a group wherein two ring systems share two and only two atoms. As used above, a fused tricyclic group or radical is a group wherein three ring systems share four and only four atoms.

The term "aralkyl" as used herein means an aryl-alkyl group or radical wherein aryl and alkyl have the meanings as defined above including where alkyl includes alkenyl, alkynyl and cycloalkyl and where aryl includes heteroaryl. Illustrative examples of an arylalkyl group or radical include benzyl, 4-fluorophenylmethyl, 2-phenylethyl, 3-phenylpropyl, 4-phenylbutyl, 3-methyl-3-phenylpropyl, 1-naphthylmethyl, 1-naphthylethyl, 3-(1-naphthyl)-propyl, 4-(1-naphthyl)-butyl, 4-(2-naphthyl)-butyl, 4-phenylheptyl, and 12-(2-hydroxyphenyl)-dodec-3-yl.

The term "alcohol protecting group" as used herein means a conventional alcohol protecting group known to those skilled in the art such as is used to protect a hydroxy group. Such alcohol protecting groups are described in T. W. Greene, Protective Groups in Organic Synthesis, John Wiley & Sons, New York, N.Y., 1991, 2nd Edition, which is hereby incorporated by reference and include for example, esters such as formyl, ($C_1$-$C_{10}$) alkanoyl optionally mono-, di- or tri-substituted with ($C_1$-$C_6$) alkoxy, halo, aryl, aryloxy or haloaryloxy; aroyl optionally mono-, di- or tri-substituted on carbon with halo, ($C_1$-$C_6$) alkyl, ($C_1$-$C_6$) alkoxy wherein aryl is phenyl, 2-furyl etc; carbonates; sulfonates; and ethers such as benzyl, paramethoxybenzyl, methoxymethyl, etc. The lev protecting group is discussed by van Boom, J. H.; Burgers, P. M. J. Tetrahedron Letters, 1976, 4875.

The term "N-heterocyclic carbene-type ligand" as used herein means N-heterocyclic carbene-type ligands generated from their corresponding salts. Preferred N-heterocyclic carbene-type ligands are those which include bulky groups that shield the carbene from dimerizing. Preferred N-heterocyclic carbene-type ligands include imidazolium, 1,3-disubstituted imidazolium (N,N'-bis-substituted imidazolium), 1,3-disubstituted-4,5-dihydroimidazolium carbene-type ligands. More preferred 1,3-disubstituted imidazolium carbene-type ligands include N,N'-bis-carbocycle imidazolium ligands. In the N,N'-bis-carbocycle imidazolium ligands, the term "carbocycle" (and variations thereof such as "carbocyclic" or "carbocyclyl") as used herein broadly refers to substituted and unsubstituted, saturated or unsaturated, mono, bi, and tricyclic ring systems in which the rings are independent or fused and in which each ring is saturated or unsaturated. Examples of an unsaturated substituted monocylic N,N'-bis-carbocycle-imidazolium salts are: N,N'-bis-(2,6-diisopropylphenyl)imidazolium chloride (also called 1,3-di-(2,6-diisopropylphenyl)imidazolium chloride) and N,N'-bis-(dimesityl)imidazolium chloride (also called 1,3-di-(2,4,6-trimethylphenyl)imidazolium chloride). An example of a saturated unsubstituted tricyclic N,N'-di-carbocycleimidazolium salt is N,N'-bis-adamantylimidazolium chloride.

The term "transition metal catalyst" as used herein means any transition metal useful in forming carbon-carbon bonds including salts, carbonyl compounds, chelates, or complexes with ligands having trivalent donor groups of the metals in Group VIII or copper. A Group VIII metal includes Fe, Co, Ni, Ru, Rh, Pd, Os, Ir, or Pt. Complex catalysts are those with ligands having trivalent donor atoms and are comprised of a Group VIII metal complexed by one or more ligands. These complexes are formed by the reaction of a Group VIII metal compound and a ligand having a trivalent donor atom. Such trivalent donor atoms include phosphorus, nitrogen, arsenic, antimony and bismuth. These types of complexes are well known to those of ordinary skill in the art and most commonly involve phosphorus-type ligands. (see R. F. Heck, Palladium Reagents in Organic Syntheses, Academic Press, N.Y., N.Y., 1985, pages 1-7; S. G. Davies, Organotransition Metal Chemistry Applications to Organic Syntheses, Pergamon Press, N.Y., N.Y., 1985, pages 13-17). Examples of the most common phosphorus-type ligands include phosphines of which the preferred are triphenylphosphine, trimethylphosphine, methyldiphenylphosphine, dimethylphenylphosphine, dicyclohexylphenylphosphine, diphenylenephenylphosphine, tri-p-tolylphosphine, tri-(p-chlorophenyl)phosphine, tris(p-methoxyphenyl)phosphine, bis-(diphenylphosphino)methane, 1,2-bis-(diphenylphosphino)ethane, bis-(dicyclohexylphosphino)ethane, bis-(2-diphenylphosphinoethyl)phenylphosphine, 1,1,1-tris-(diphenylphosphinomethyl)ethane, tris-(2- diphenylphosphinoethyl)phosphine, 1,1,4,7,10,10-hexaphenyl-1,4,7,10-tetraphosphadecane, and 1,1-bis-(diphenylphosphino)ferrocene. The complex catalysts are used in conjunction with a ligand having a trivalent donor atom. The preferred ligand is phosphine or a phosphine derivative such as those listed above. The relative amounts of phosphine and Group VIII metal which can be used in the processes according to the invention are best expressed as a ratio of the number of moles of phosphorus in the phosphine compound to the number of moles of Group VIII metal. The preferred catalysts are salts, carbonyl compounds, chelates, or complexes of Rh, Pd, Ir, and Ru. Particularly preferred catalysts are $RhCl_3$, $PdCl_2$, $PdBr_2$, $IrCl_3$, $Pd(OOCCH_3)_2$, $(RhCl(CO)_2)_2$, palladium bis triphenylphosphine, and palladium tris triphenyl phosphine. A more preferred Pd II catalyst is $Pd(OAc)_2$.

The term "polyprotection" as used herein means reacting one or more protecting reagents at one or more heteroatoms.

Synthetic Schemes

Scheme 1 illustrates the general procedure for the preparation of the compounds of Formula 1 where each Y and each Z are independently selected from halogen, —OH, —OR, —O—C=O—R, n is equal to 0, 1, 2, 3, 4 or 5, m is equal to 0, 1, 2, 3, 4 or 5, each A and each B are independently selected from the group comprising alkyl with at least one carbon atom, aryl, aralkyl, $P_n$ (wherein $P_n$ is a protecting group), and H. It should be appreciated that with regard to compounds of Formulas 1B, 1C, 1D, 1E, and 1F, A and B do not represent H; and, with regard to compounds of Formula 1A, when any Y or any Z is halogen, A or B is absent. Preferably, the sum of n and m is 1 or more. In some embodiments R is alkyl with at least two carbon atoms.

Scheme 1.

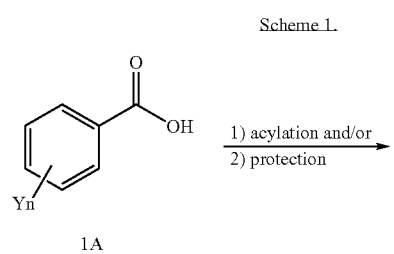

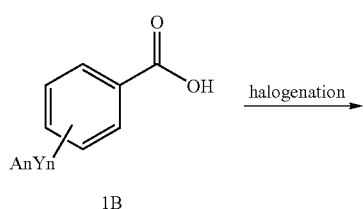

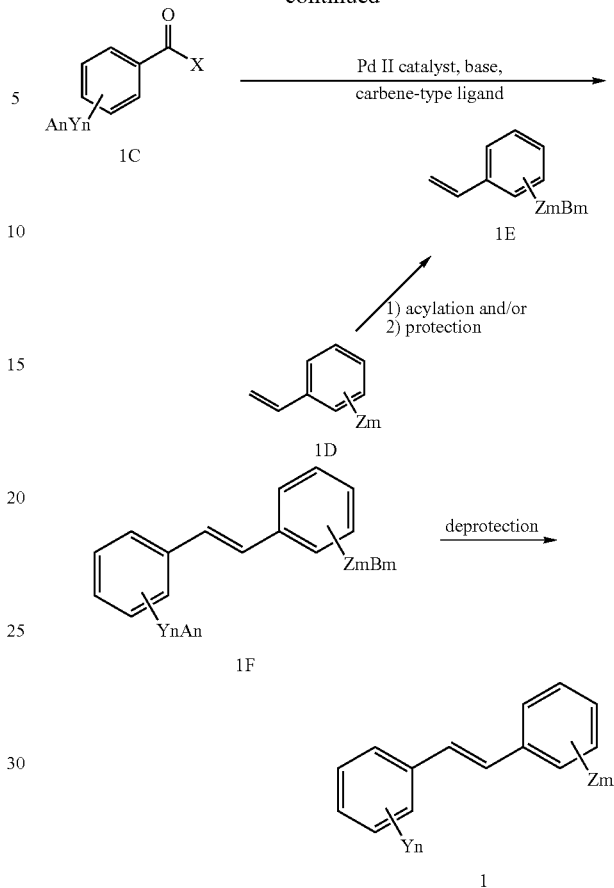

Protection/Acylation of Benzoic Acid Halide Coupling Partner

As depicted in Scheme 1, the benzoic acid derivative 1A is optionally acylated and/or optionally protected with a desired number and type of acyl group(s) equal to or less than n and/or with the desired number and type of protecting group(s) equal to or less than n to yield benzoic acid derivative 1B where A is selected from the group comprising alkyl with at least one carbon atom, aryl, aralkyl, and $P_n$.

A variety of reaction pathways starting with benzoic acid derivative 1A can be used to obtain the benzoic acid derivative 1B. These include homogenous peracylation or polyacylation (condition I), homogenous polyprotection (condition II), selective acylation followed by selective protection (condition III), selective protection followed by selective acylation (condition IV), heterogeneous peracylation (condition V), heterogeneous polyprotection (condition VI), selective acylation followed by homogeneous or heterogeneous polyprotection (condition VII) and selective protection followed by homogeneous or heterogeneous peracylation (condition IIX). It is contemplated that under condition VII, selective acylation may occur at one or more substituent sites and polyprotection may occur at one or more substituents sites. In like manner, it is contemplated that under condition IIX, selective protection may occur at one or more substituent sites and peracylation may occur at one or more substituents sites. When each Y or each Z is halogen, the acylation and/or protection and diprotection steps may be entirely omitted. Where one or more of Y and Z are halogen and one or more of Y and Z is neither H nor halogen, the acylation and/or protection and diprotection steps may be implemented.

It is to be understood from this description that benzoic acid 1A includes benzoic acid and monohydroxyl benzoic acids 2-hydroxy benzoic acid (salicylic acid), 3-hydroxy benzoic acid and 4-hydroxy benzoic acid in which case only conditions I or II can apply.

Benzoic acid 1A also includes but is not limited to the dihyroxyl benzoic acids. Illustrative examples of which include but are not limited to 2,3-dihydroxybenzoic acid, 3,5-dihydroxybenzoic acid (α-resorcylic acid), 2,4-dihydroxybenzoic acid (β-resorcylic acid), 2,6-dihydroxybenzoic acid (γ-resorcylic acid), 2,5-dihydroxybenzoic acid (hydroquinonecarboxylic acid, gentisic acid) and 3,4-dihyroxybenzoic acid (protocatechuic acid) in which case conditions I-VI can apply.

Benzoic acid 1A also includes but is not limited to the trihydroxyl benzoic acids. Illustrative examples of which include but are not limited to 3,4,5-trihydroxybenzoic acid (gallic acid), 2,3,4-trihydroxybenzoic acid, 2,4,5-trihydroxybenzoic acid and 2,4,6-trihydroxybenzoic acid (phloroglucinolcarboxylic acid) in which case conditions I-IIX can apply.

By way of illustration, the resorcylic acid analogs of 1A, where n=2 and each Y is OH, has two hydroxyls that can be 1) both esterified with one or more esterifying agents (condition I), 2) both protected with a one or more protecting agents (condition II), 3) selectively esterified with an esterifying agent and selectively protected with a protecting agent (condition III), 4) selectively protected with a protecting agent and selectively esterified with an esterifying agent (condition IV), 5) heterogeneous diesterification with both hydroxyls esterified with two different esterifying agents (condition V), or 6) heterogeneous diprotection with both hydroxyls protected with two different protecting agents (condition VI).

In the example of diesterification (condition I), both hydroxyls are reacted with at least 2 equivalents of an esterifying agent in a basic solvent (or in an inert solvent with added base) to give the diester resorcylic acid derivative $1B_a$ where $A_1$ and $A_2$ are the same. Preferably, a 5 molar equivalent excess of the esterifying agent is used.

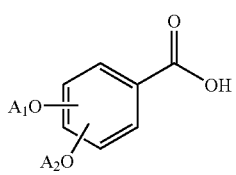

1Ba

In the example of diprotection (condition II), both hydroxyls are reacted with at least 2 equivalents of a protection agent and under conditions known to one skilled in the art for the desired alcohol protecting group to give diprotected resorcylic acid derivative $1B_a$ where $A_1$ and $A_2$ are the same.

In the example of selective esterification followed by selective protection (condition III), resorcylic acid is first reacted with 1 equivalent or more of an esterifying agent in a basic solvent (or in an inert solvent with added base) to give resorcylic acid derivative $1B_b$ where $OA_1$ represents an ester. Intermediate $1B_b$ is then reacted with 1 equivalent or more of a protection agent and under conditions known to one skilled in the art for the desired alcohol protecting group to give resorcylic acid derivative $1B_a$ where $OA_2$ represents a protected alcohol.

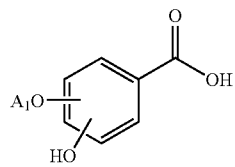

1Bb

In the example of selective protection followed by selective esterification (condition IV), resorcylic acid is first reacted with 1 equivalent or more of a protection agent and under conditions known to one skilled in the art for the desired alcohol protecting group to give resorcylic acid derivative $1B_b$ where $OA_1$ represents a protected alcohol. Intermediate $1B_b$ is then reacted with 1 equivalent or more of a esterifying agent in a basic solvent (or in an inert solvent with added base) to give resorcylic acid derivative $1B_a$ where $OA_2$ represents an ester.

In the example of heterogeneous diesterification (condition V), resorcylic acid is first reacted with 1 equivalent or more of a first esterifying agent in a basic solvent (or in an inert solvent with added base) to give resorcylic acid derivative $1B_b$ where $OA_1$ represents a first ester. Intermediate $1B_b$ is then reacted with 1 equivalent or more of a second esterifying agent to give resorcylic acid derivative $1B_a$ where $OA_2$ represents a second ester.

In the example of heterogeneous diprotection (condition VI), resorcylic acid is first reacted with 1 equivalent or more of a first protection agent under conditions known to one skilled in the art for the desired alcohol protecting group to give resorcylic acid derivative $1B_b$ where $OA_1$ represents a first protected alcohol. Intermediate $1B_b$ is then reacted with 1 equivalent or more of a second protecting agent to give resorcylic acid derivative $1B_a$ where $OA_2$ represents a second protected alcohol.

Suitable acylating agents useful in the step or steps described above include but are not limited to acid anhydrides, acid halides, and mixed acid anhydrides of the formulas $R_4CO_2COR_4$, $R_4COX$, $R_4CO_2COR_5$ respectively where $R_4$ is alkyl with at least one carbon atom, aryl, aralkyl and diastereoisomers of the foregoing, $R_5$ is alkyl with at least one carbon atom, aryl, aralkyl and diastereoisomers of the foregoing, X is halogen. Cl is a preferred halogen. Acylation is carried out with basic solvents including but not limited to ethyl amine, diethyl amine, triethylamine, pyrrole, imidazole, triazole, pyrazole, pyridine, pyrazine, pyrimidine, pyridazine, pyrazine, triazine, pyrrolidine, piperidine, DMF, NMP, dimethylpropyl urea, hexamethyl phosphortriamide (HMPA), and mixtures of said solvents. Other appropriate solvents are known to one skilled in the art. Pyridine is a preferred basic solvent. Alternatively, acylation can be carried out in an inert solvent with added base.

In the examples where acylation results in an ester (i.e. X is O), esterification is followed by treatment with aqueous formic acid and optionally by recrystallization. In the examples where acylation results in an amide (i.e. X is NH), acylation is followed by treatment with any mild acid and optionally by recrystallization.

Suitable protecting groups are described in T. W. Greene, Protective Groups in Organic Synthesis, John Wiley & Sons, New York, N.Y., 1991, 2nd Edition. Preferred alcohol protecting groups are those that can be selectively cleaved over a phenyl ester and include those derived from chloromethoxymethyl acetate (MOMCl), chloroacetoxy anhydride, levulonic anhydride. Silicon protecting groups such as tert-butyldimethylsilyl and tert-butylsilyl were not found to be compatible. Ether protecting groups such as methyl and benzyl ethers do not work as well since the Lewis acid conditions employed during deprotection are harsher as to other portions of the desired products.

Preferred amine protecting groups are those that can be selectively cleaved over a phenyl amine and include tert-butyloxycarbonyl (BOC), fluorinomethyloxycarbonyl (FMOC), and benzyloxycarbonyl (Cbz).

Halogenation of Acid Chloride Coupling Partner

Returning to Scheme 1, benzoic acid derivative 1B is reacted with a halogenating agent in an inert solvent to yield the benzoic acid halide derivative 1C where X is any halogen.

Suitable halogenating agents useful in this step include but are not limited to any of the halogenating agents known to the art, such as thionyl halides including thionyl chloride, thionyl bromide and thionyl iodide, oxalyl halides including oxalyl chloride, oxalyl bromide and oxalyl iodide, phosphorous tri- and pentahalides and phosphorous oxyhalides. Halogenation is carried out in an inert solvent including but not limited to halogenated alkanes such as methylene chloride and chloroform; cyclic ethers, such as THF and dioxane; N,N-dialkyl-substituted acylamides, such as DMF and DMAC; and mixtures of said solvents.

The halogenation reaction may optionally include a buffering agent capable of associating with HX acid. Suitable buffering agents include weak bases. Benzotriazole is a preferred buffering agent during halogenation because it precipitates as a salt after reacting with a HX acid.

The reaction is effected at a temperature from about 0° to about 100° C. Preferably, the reaction is effected using thionyl chloride or oxalyl chloride in a polar solvent such as methylene chloride, at 80° C., in the presence of benzotriazole to yield the corresponding acid chloride.

Optionally, the intermediate 1C is recrystallized from hexane.

Preparation of Styrene Coupling Partner

Also depicted in Scheme 1 is styrene derivative 1D. Styrene 1D is optionally acylated and/or optionally protected with a desired number and type of acyl group(s) equal to or less than m and/or with the desired number and type of protecting group(s) equal to or less than m to yield styrene benzoic acid derivative 1E where A is selected from the group comprising alkyl with at least one carbon atom, aryl, aralkyl, and $P_m$.

A variety of reaction pathways starting with styrene derivative 1D can be used to obtain the styrene derivative 1E. These pathways include homogenous peracylation or polyacylation (condition I), homogenous polyprotection (condition II), selective acylation followed by selective protection (condition III), selective protection followed by selective acylation (condition IV), heterogeneous peracylation (condition V), heterogeneous polyprotection (condition VI), selective acylation followed by homogeneous or heterogeneous polyprotection (condition VII) and selective protection followed by homogeneous or heterogeneous peracylation (condition IIX). It is contemplated that under condition VII, selective acylation may occur at one or more substituent sites and polyprotection may occur at one or more substituents sites. In like manner, it is contemplated that under condition IIX, selective protection may occur at one or more substituent sites and peracylation may occur at one or more substituents sites.

It is to be understood from this description that styrene derivative 1A includes styrene and the monohydroxyl styrenes 2-hydroxy styrene, 3-hydroxy styrene and 4-hydroxy styrene in which case only conditions I or II can apply. Styrene derivative 1D also includes but is not limited to the dihyroxyl styrenes. Illustrative examples of which include but are not limited to 2,3-dihyroxystyrene, 3,5-dihydroxystyrene, 2,4-dihyroxystyrene, 2,6-dihydroxystyrene, 2,5-dihydroxystyrene and 3,4-dihydroxystyrene in which case conditions I-VI can apply. Styrene derivative 1D also includes but is not limited to the trihydroxyl styrenes. Illustrative examples of which include but are not limited to 3,4,5-trihydroxystyrene, 2,3,4-trihydroxystyrene, 2,4,5-trihydroxystyrene and 2,4,6-trihydroxystyrene in which case conditions I-IIX can apply.

By way of illustration, the monohydroxyl styrene analogs of 1D (where n=1 and Y is OH) has one hydroxyl that can be 1) esterified with an esterifying agent (condition I) or 2) protected with a protecting agent (condition II). The monohydroxyl styrenes can be prepared by saponification of the corresponding acetoxy styrenes, e.g. 4-hydroxystyrene from 4-acetoxystyrene.

Coupling Step Via Decarbonylative Heck Reaction

Returning to Scheme 1, benzoic acid halide 1C is reacted with styrene 1E via a decarbonylative coupling reaction to give stilbene 1F. The reaction conditions associated with the coupling reaction can include an inert apolar, high-boiling point aromatic or hydrocarbon solvent with a transition metal catalyst, N-heterocyclic carbene-type ligand and base.

Suitable inert solvents useful in the coupling step include but are not limited to benzene, toluene, xylene, chlorobenzne, decane, dodecane, and mixtures of those solvents. Xylene is a preferred solvent in the coupling step.

A preferred transition metal catalyst used in the coupling step is $Pd(OAc)_2$.

A preferred N-heterocyclic carbene-type ligands useful in the coupling step is N,N-bis-(2,6-diisopropylphenyl) 4,5-dihydroimidazolium chloride in an amount of 0.1-10 mol %, preferably 5-10 mol %.

Surprisingly, the nature of the added base significantly affects the efficiency of the reaction. Non-coordinating amine bases result in greater yields than coordinating amine bases. Examples of non-coordinating bases useful in the process include but are not limited to N-ethylmorpholine (NEM), N,N-dimethylbenzylamine, dimethylaminopyridine (DMAP), proton sponge (1,8-diaminonaphthalene), diisopropylethylamine (Hunig's base) and triethylamine. N-ethylmorpholine and N,N-dimethylbenzylamine are preferred bases in the coupling step. Use of smaller amines capable of transition metal coordination still work to obtain the coupled product 1F but are less efficient. Furthermore, phosphine ligands can also be added to the reaction; however, added phosphine ligand inhibits the reaction giving greatly lowered yields.

The reaction is effected at a temperature from about 0 to about 150° C. Preferably, the reaction is refluxed in xylene.

The reaction depicted in Scheme 1 is concluded using standard work-up conditions and the reaction products can be purified using a variety of techniques known to those skilled in the art including silica gel chromatography.

Deprotection Step

After performing the coupling reaction, in those cases where one or more protecting groups exist on the stilbene derivative 1F, the protection groups may be deprotected as described in T. W. Greene, Protective Groups in Organic Synthesis, John Wiley & Sons, New York, N.Y., 1991, 2nd Edition for each of the respective protection groups and may require one or more steps to complete. With respect to the preferred hydroxyl protecting groups, the methoxymethyl acetate (MOM) may be selectively hydrolyzed by reaction with sodium iodide and trimethylsilyl chloride (TMSCl); chloroacetoxy groups may be selectively hydrolyzed when treated with 50% aqueous pyridine at a pH of 6.7; the levulinoate (lev) may be selectively hydrolyzed with sodium thiosulfate (Na2SO3) and sodium metabisulfite.

If desired, phenolic esters may also be cleaved, if present, by hydrolysis using saponification techniques known to one skilled in the art. Ester hydrolysis may be carried out before or after deprotection of any protecting groups.

In the example of stilbene derivatives 1F akin to resveratrol, where Y=O at the 3 and 5 positions, n=2, Z=O at the 4' position and m=1, the derivative may be 1) deesterified at all three phenolic sites (3,5, and 4'), 2) deprotected and/or deesterified at all three phenolic sites and 3) selectively deprotected at any of the three phenolic sites.

In the example of deesterification at any of the three phenolic sites, basic hydrolysis (saponification) can be carried out in a polar aprotic inert solvent including but not limited to dimethylsulfoxide (DMSO), N-methylpyrrolidone, tetrahydrofuran (THF), acetone, acetonitrile, methylene chloride, chloroform, mixtures of said polar aprotic inert solvents and others known to one skilled in the art with a suitable base including but not limited to alkali metal hydroxides (e.g., LiOH, NaOH and KOH) and alkaline earth metal hydroxides (e.g., $Mg(OH)_2$, $Ca(OH)_2$, and $Ba(OH)_2$). A preferred solvent is THF. A preferred alkaline earth metal hydroxide base is KOH.

Olefin Isomerization

The stilbene compounds of the present invention possess a conjugated double bond. The double bond may exist in the cis or trans configuration. The present invention includes both cis and trans isomers as mixtures or in purified form. Furthermore, one aspect of the present invention includes a process for isomerizing the trans configuration to the cis configuration. As depicted in Scheme 2, the isomerization step may be conducted to the stilbene derivatives when Y and/or Z are acylated, protected, or the free alcohol. Compounds of the Formulas 1A3, 1B, I, II, 1, 3-7 can be diluted in an inert solvent and irradiated with ultraviolet light, preferably of wavelength λ=280-350 nm. This ultraviolet irradiation is carried in organic solution, at temperatures of 0° to 50°, preferably of 10° to 30°. The irradiation can be carried out with the aid of the most diverse commercial ultraviolet apparatuses. By way of example, irradiation can be carried out with a medium-pressure mercury vapor lamp through a pyrex filter. The irradiation time is generally from 2 to 100 hours, preferably 5 to 50 hours, especially 10 to 20 hours.

Resveratrol Esters Coupling Step Via Decarbonylative Heck Reaction

In the preferred embodiments that follow, selective ester derivatives of resveratrol can be prepared where the 3-hydroxyl, 5-hydroxyl and 4'-hydroxyl can independently be selectively substituted. In the preferred ester derivatives of resveratrol, $R_1$, $R_2$ and $R_3$ are each independently selected from the group comprising alkyl with at least one carbon atom, aryl, aralkyl, and diastereoisomers of the foregoing and $P_1$, $P_2$ and $P_3$ are alcohol protecting groups. In some embodiments R is alkyl with at least two carbon atoms. In some embodiments the sum of m and n is greater than or equal to one but less than nine. In other embodiments the sum of m and n is three or more but less than nine.

With reference to Formula $1A_3$, a first preferred embodiment constitutes the 3-ester derivatives of resveratrol. In that embodiment, $A_1$ is $R_1$, $A_2$ is $P_2$ or OH, and $A_3$ is $P_3$ or OH. As explained more specifically later in this description, this embodiment is equivalent (or degenerate) when $A_1$ is $P_1$ or OH, $A_2$ is $R_2$, and $A_3$ is $P_3$ or OH. A second preferred embodiment constitutes the 3,5-diester derivatives of resveratrol. Therein, $A_1$ is $R_1$, $A_2$ is $R_2$, and $A_3$ is $P_3$ or OH. A third preferred embodiment constitutes the 3,4'-diester derivatives of resveratrol when $A_1$ is $R_1$, $A_2$ is $P_2$ or OH, and $A_3$ is $R_3$. As explained more specifically later in this description, this embodiment is equivalent (or degenerate) when $A_1$ is $P_1$ or OH, $A_2$ is $R_2$, and $A_3$ is $R_3$. A fourth preferred embodiment constitutes the 4' ester derivatives of resveratrol. Therein, $A_1$ is $P_1$ or OH, $A_2$ is $P_2$ or OH, and $A_3$ is $R_3$. A fifth preferred embodiment constitutes the 3,5,4'-triester derivatives of resveratrol. In the embodiments which constitute diester and triester derivatives of resveratrol, the esters may the same or different. Furthermore, in the embodiments that follow with more than one protecting group, $P_1$, $P_2$ and $P_3$ may the same or different. The resveratrol ester derivatives can be of the cis-stilbene or trans-stilbene configuration.

Scheme 3 illustrates one procedure for the preparation of the mono- and di-esters of resveratrol.

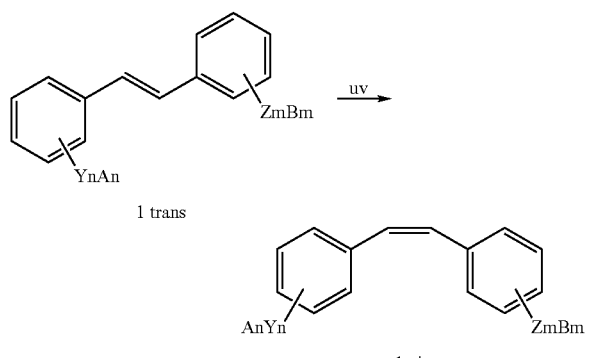

Scheme 2.

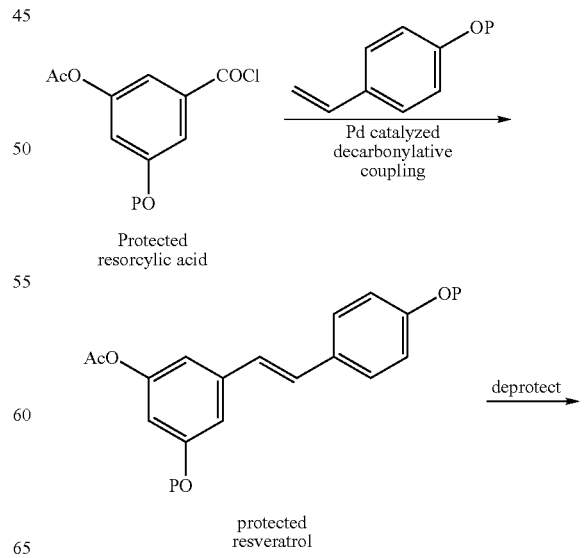

Scheme 3.

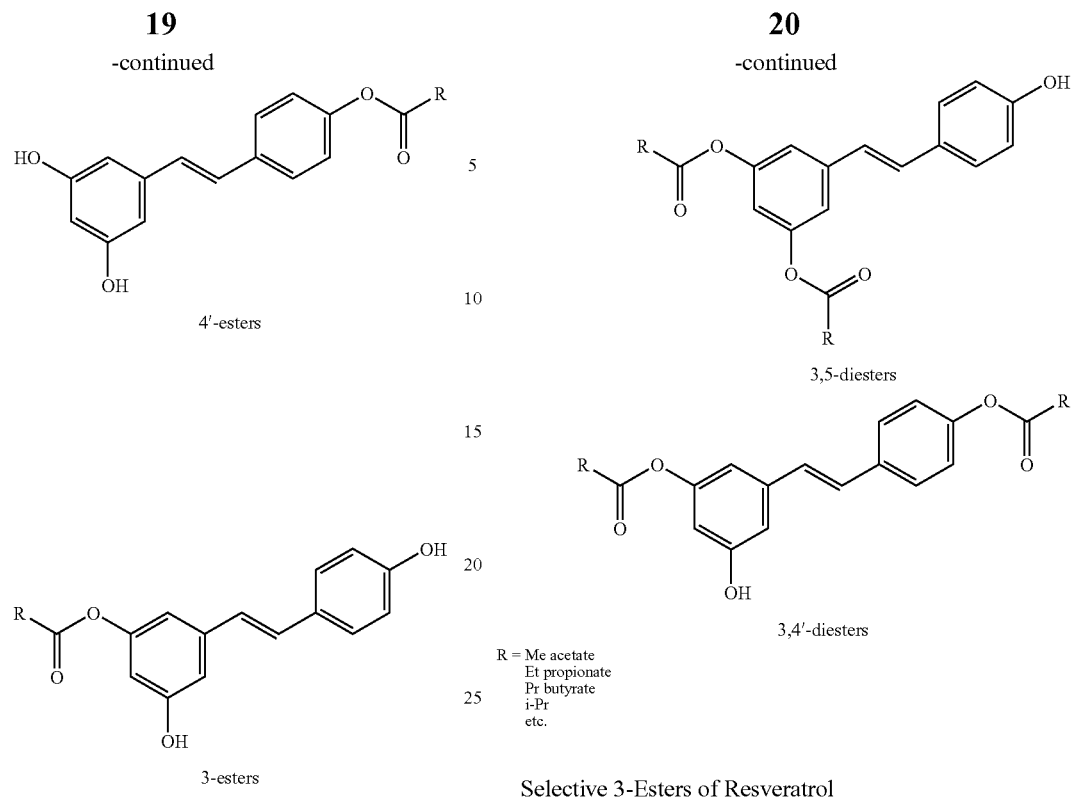
Selective 3-Esters of Resveratrol
Selective 3-ester derivatives of resveratrol may also be prepared by the process depicted in Scheme 4.
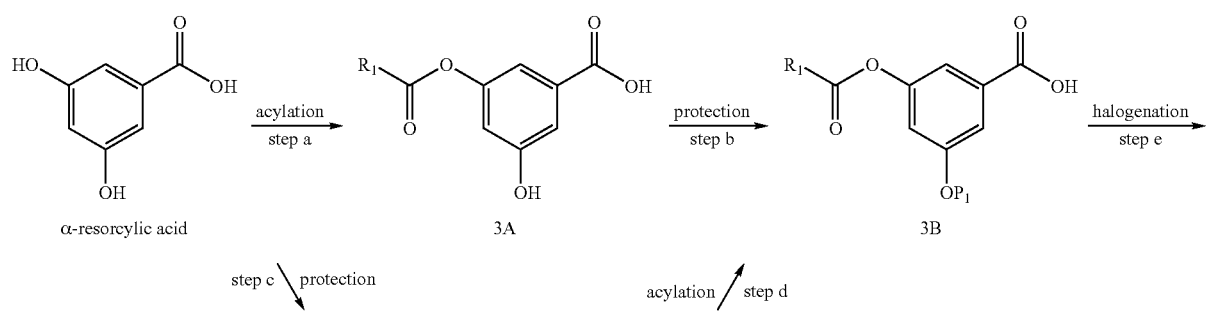
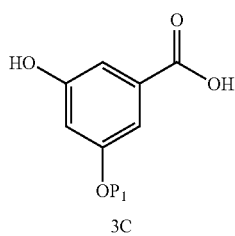

-continued

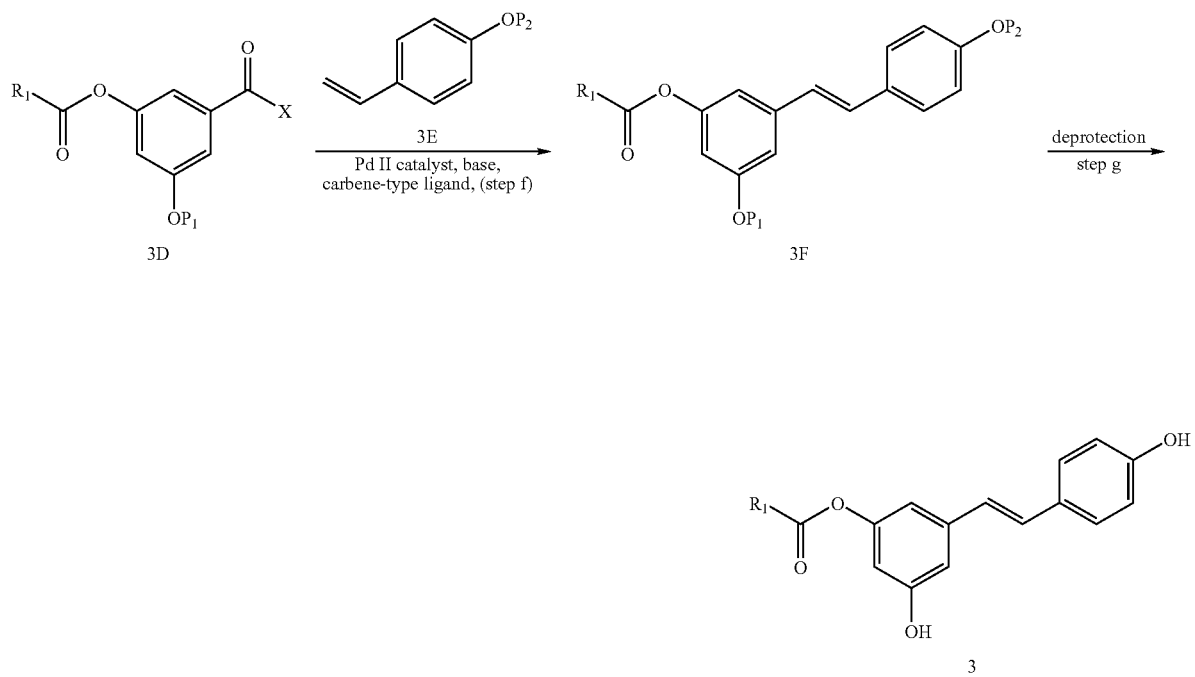

In a preferred embodiment, 3-ester compounds of Formula 3, pharmaceutically and cosmetically acceptable salts thereof wherein $R_1$ is selected from alkyl with at least one carbon atom, aryl, aralkyl, and diastereoisomers of the foregoing, are synthesized from the steps a and b (or alternatively c and d), e, f, and g: wherein step a) is esterifying resorcylic acid with an esterifying agent in solution or in suspension of a first solvent to give the 3-ester of resorcylic acid of Formula 3A; step b) is reacting the hydroxyl of said compound of Formula 3A with a first alcohol protecting agent in solution or in suspension of a second solvent to give a compound of Formula 3B; where $P_1$ is a first alcohol protecting group; step c) is reacting resorcylic acid with a first alcohol protecting agent in solution or in suspension of a second solvent to give a compound of Formula 3C, where $P_1$ is a first alcohol protecting group; step d) is reacting the 5-hydroxy of said compound of Formula 3C with an esterifying agent in solution or in suspension of a first solvent to give the 3-ester of resorcylic acid of Formula 3B; step e) is halogenating said compound of Formula 3B using a halogenating agent in solution or in suspension of a third solvent to give the acid halide of Formula 3D, wherein X is halogen; step f) is coupling said compound of Formula 3B with a compound of Formula 3D, where $P_2$ is a second alcohol protecting group, with Pd II catalyst, N-heterocyclic carbene-type ligand, and a first base in solution or in suspension of a fourth solvent to yield a compound of Formula 3E; and, step g) is deprotecting said first and second alcohol protecting groups from said compound of Formula 3E to give a compound of Formula 3. In some embodiments R is alkyl with at least two carbon atoms.

Compounds of the invention are those prepared by the above process.

As mentioned previously, Scheme 4 illustrates the general procedure for the preparation of the compounds of Formula 3. The compounds of Formula 3 may be generally characterized as the 3-esters of resveratrol, that is, the phenolic hydroxyls at the 5 and 4' positions are the free alcohols while the phenolic hydroxyl at the 3 position is an ester.

The 3-esters of resveratrol are prepared by either 1) reacting one of the resorcylic acid hydroxyls with one or more equivalents of a desired esterifying agent followed by protection of the remaining hydroxyl with a suitable alcohol protection agent or 2) reacting one of the resorcylic acid hydroxyls with one or more equivalents of a suitable protecting agent followed by esterification of the remaining hydroxyl with one or more equivalents of a desired esterifying agent. The esterified/protected acid is halogenated to a corresponding acid halide. A 4-protectedhydroxy styrene is made by reacting 4-hydroxystyrene with a desired protecting agent. The 4-protectedhydroxy styrene is reacted with the esterified/protected acid halide in a decarbonylative Heck reaction as described above. After coupling, the protection groups at the 5 and 4' positions are removed to give the 3-ester of resveratrol.

In either of the above reaction pathways, reaction at one of the two phenolic hydroxyls of resorcylic acid is equivalent (or degenerate) to reaction at the other hydroxyl because of the symmetry of α-resorcylic acid. By way of example, if the first reaction is monoesterification of α-resorcylic acid, reaction at the 3-hydroxyl would be equivalent to the reaction at the 5-hydroxyl as both products would be indistinguishable because of the mirror plane passing along the first and fourth carbons of the aromatic ring. In that regard, compound 3-acetoxy-5-hydroxy benzoic acid is equivalent to the compound 5-acetoxy-3-hydroxy benzoic acid. Therefore, the 5-ester derivatives of resveratrol are equivalent (or degenerate) to the 3-ester derivatives of resveratrol.

Selective 3,5-Diesters of Resveratrol

Selective 3,5-diester derivatives of resveratrol may also be prepared by the process depicted in Scheme 5.

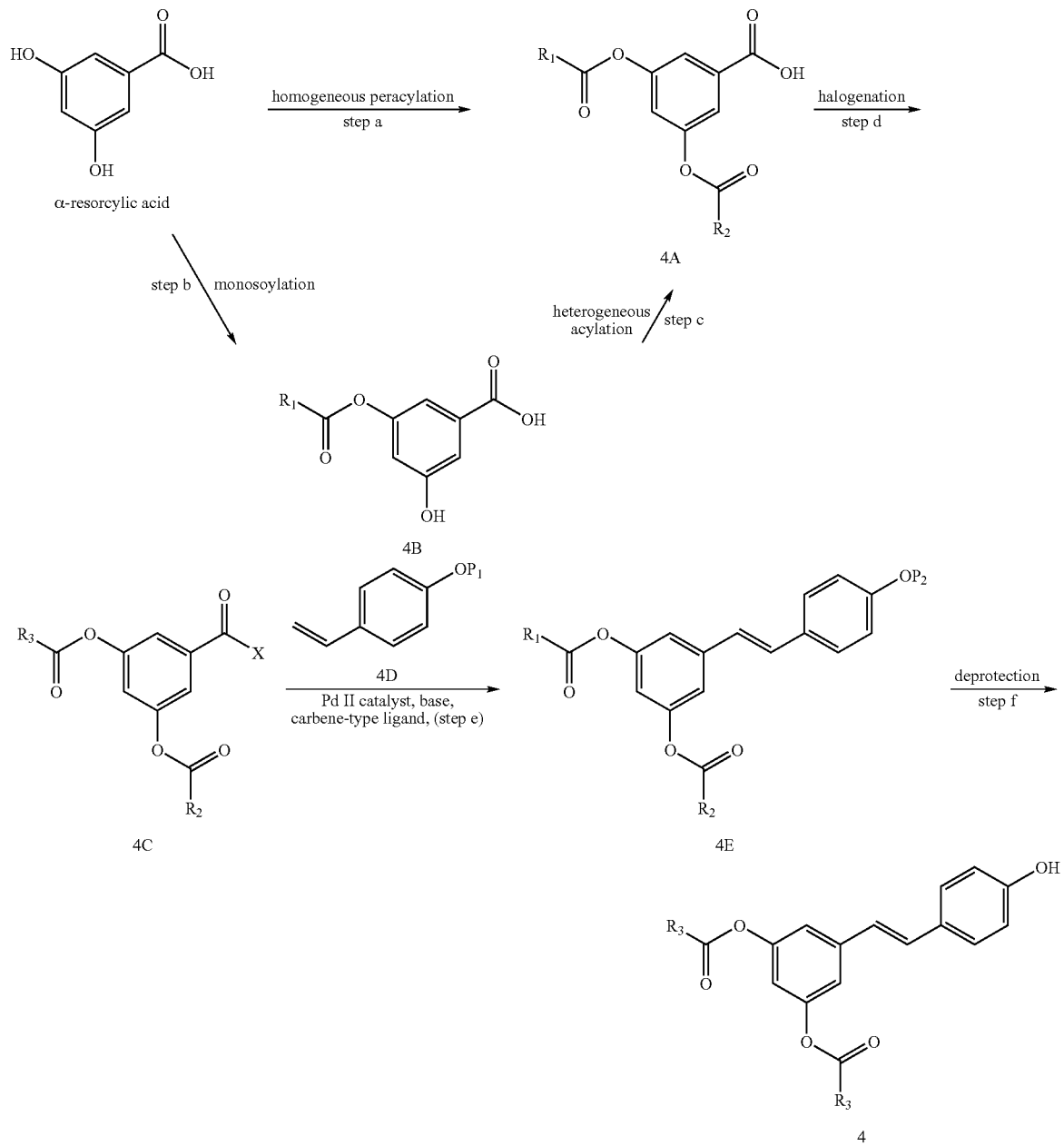

Scheme 5.

In a preferred embodiment, 3,5-diester compounds of Formula 4, pharmaceutically and cosmetically acceptable salts thereof wherein $R_1$ and $R_2$ are independently selected from alkyl with at least one carbon atom, aryl, aralkyl, and diastereoisomers of the foregoing, are synthesized from the steps of a (or alternatively b and c), d, e, and f: wherein step a) is esterifying resorcylic acid with an esterifying agent in solution or in suspension of a first solvent to give the 3,5-diester of resorcylic acid of Formula 4A wherein $R_1$ and $R_2$ are the same; step b) is esterifying resorcylic acid with a first esterifying agent in solution or in suspension of a first solvent to give the 3-ester of Formula 4B; step c) is esterifying said compound of Formula 4B with a second esterifying agent in solution of in suspension of a second solvent to give the 3,5-diester of Formula 4A wherein $R_1$ and $R_2$ are different; step d) is halogenating said compound of Formula 4A using a halogenating agent in solution or in suspension of a third solvent to give the acid halide of Formula 4C, wherein X is halogen; step e) is coupling said compound of Formula 4B with a compound of Formula 4D, wherein $P_1$ is a first alcohol protecting group, with Pd II catalyst, N-heterocyclic carbene-type ligand, and a first base in solution or in suspension of a fourth solvent to yield a compound of Formula 4E; and, step f) is deprotecting said first alcohol protecting group from said compound of Formula 4E to give a compound of Formula 4. In some embodiments R is alkyl with at least two carbon atoms.

Compounds of the invention are those prepared by the above process.

Returning to Scheme 5, the general procedure for the preparation of the compounds of Formula 4 is depicted. The compounds of Formula 4 may be generally characterized as the 3,5-diesters of resveratrol, that is, the phenolic hydroxyl at the 4' position is the free alcohol while the phenolic hydroxyls at the 3 and 5 positions are esters. In some embodiments the 3 and 5 esters are the same while in other embodiments the 3 and 5 esters are different.

the protection group at the 4' position is removed to give the 3,5-diester of resveratrol. A preferred protection group used with the 4-hydroxy styrene is chloroacetoxy.

Selective 3,4'-Diesters of Resveratrol

Selective 3,4'-diester derivatives of resveratrol may also be prepared by the process depicted in Scheme 6.

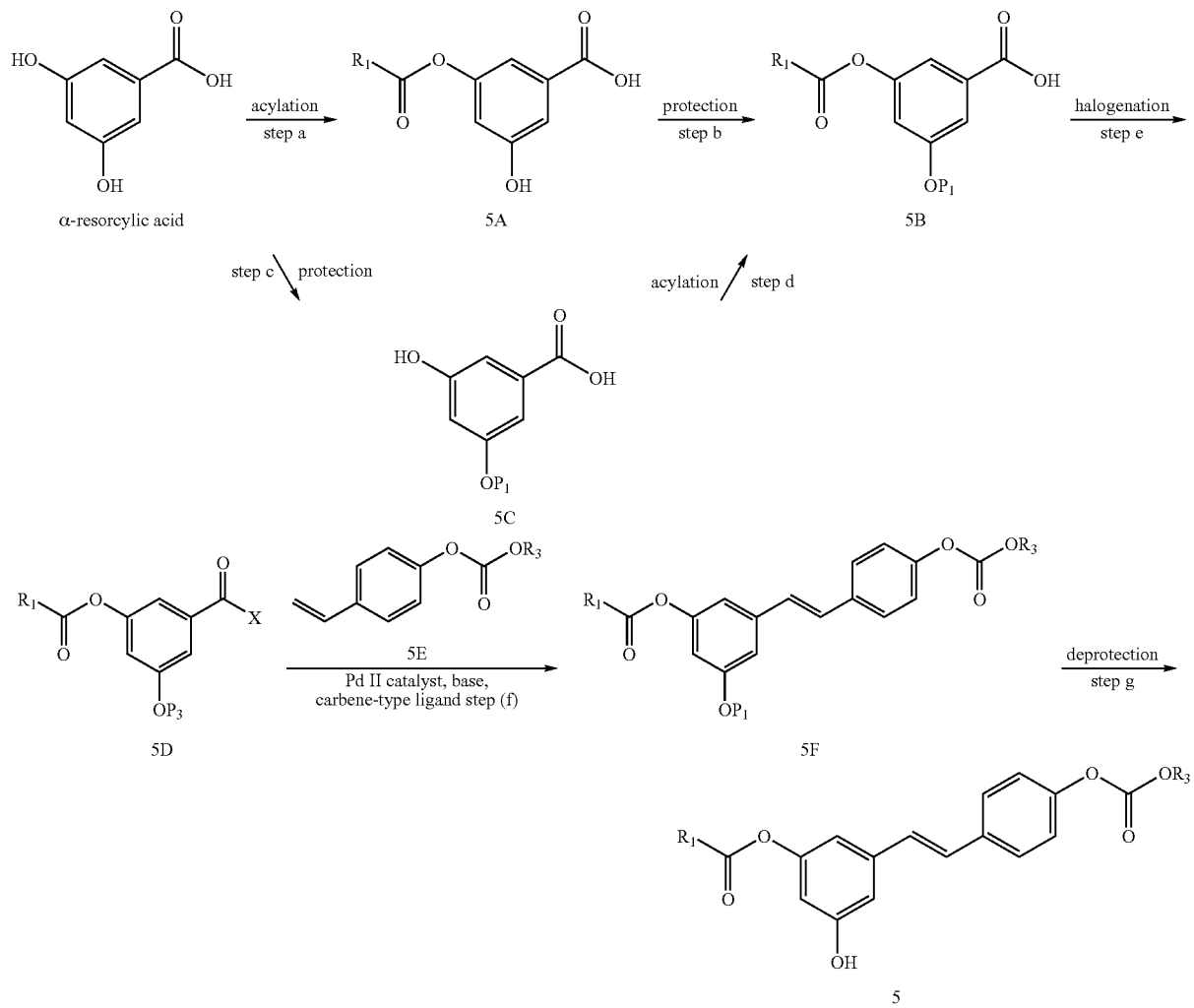

The 3,5-diesters of resveratrol are prepared by reacting resorcylic acid with two or more equivalents of a desired esterifying agent. In the alternative for mixed esters, resorcylic acid is reacted with one or more equivalents of a first esterifying agent and subsequently reacted with one or more equivalents of a second esterifying agent. Advantageously, the mixed ester can be prepared in one pot if the second esterifying agent is added after the first esterifying agent has reacted to completion or near to completion. The diesterified (heterogeneous or homogenous esters) resorcylic acid derivative is halogenated to a corresponding acid halide. A 4-protectedhydroxy styrene is made by reacting 4-hydroxystyrene with a desired protecting agent. The 4-protectedhydroxy styrene is reacted with the diesterified acid chloride in a decarbonylative Heck reaction as described above. After coupling, In another preferred embodiment, 3,4'-diester compounds of Formula 5, pharmaceutically and cosmetically acceptable salts thereof wherein $R_1$ and $R_3$ are independently selected from alkyl with at least one carbon atom, aryl, aralkyl, and diastereoisomers of the foregoing, are synthesized from the steps comprising the steps a and b (or alternatively c and d), and e, f, and g: wherein step a) is esterifying resorcylic acid with an esterifying agent in solution or in suspension of a first solvent to give the 3-ester of resorcylic acid of Formula 5A; step b) is reacting the 5-hydroxy of said compound of Formula 5A with a first alcohol protecting agent in solution or in suspension of a second solvent to give a compound of Formula 5B, where $P_2$ is a first alcohol protecting group; step c) is reacting resorcylic acid with a first alcohol protecting agent in solution or in suspension of a second solvent to give a compound of Formula 5C, where $P_2$ is an alcohol protecting group; step d) is reacting the 5-hydroxy of said compound of Formula 5C with an esterifying agent in solution or in suspension of a first solvent to give the 3-ester of resorcylic acid of Formula 5B; step e) is halogenating said compound of Formula 5B using a halogenating agent in solution or in suspension of a third solvent to give the acid halide of Formula 5D, wherein X is halogen; step f) is coupling said compound of Formula 5D with a compound of Formula 5E, with Pd II catalyst, N-heterocyclic 3arbine-type ligand, and a first base in solution or in suspension of a fourth solvent to yield a compound of Formula 5F; and, step g) is deprotecting said first and second protecting groups from said compound of Formula 5F to give a compound of Formula 5. In some embodiments R is alkyl with at least two carbon atoms.

Compounds of the invention are those prepared by the above process.

Returning to Scheme 6, the general procedure for the preparation of the compounds of Formula 5 is shown. The compounds of Formula 5 may be generally characterized as the 3,4'-diesters of resveratrol, that is, the phenolic hydroxyl at the 5 position is the free alcohol while the phenolic hydroxyls at the 3 and 4' positions are esters.

The 3,4'-diesters of resveratrol are prepared by either 1) reacting one of the resorcylic acid hydroxyls with one or more equivalents of a desired esterifying agent followed by protection of the remaining hydroxyl with a suitable alcohol protection agent or 2) reacting one of the resorcylic acid hydroxyls with one or more equivalents of a suitable protecting agent followed by esterification of the remaining hydroxyl with one or more equivalents of a desired esterifying agent. The esterified/protected acid is halogenated to a corresponding acid halide. A 4-ester styrene is made by reacting 4-hydroxystyrene with a desired esterifying agent. The 4-ester styrene is reacted with the esterified/protected acid halide in a decarbonylative Heck reaction as described above. After coupling, the protection group at the 5 position is removed to give the 3,4'-diester of resveratrol.

As mentioned in relation to the synthesis of the 3-ester (and degenerate 5-ester) derivatives of resveratrol earlier, in either of the above reaction pathways, reaction at one of the two phenolic hydroxyls of resorcylic acid is equivalent (or degenerate) to reaction at the other hydroxyl because of the symmetry of α-resorcylic acid. Hence, the 5,4'-diester derivatives of resveratrol are equivalent (or degenerate) to the 3,4'-diester derivatives of resveratrol.

Selective 4'-Esters of Resveratrol

Selective 4'-ester derivatives of resveratrol may also be prepared by the process depicted in Scheme 7.

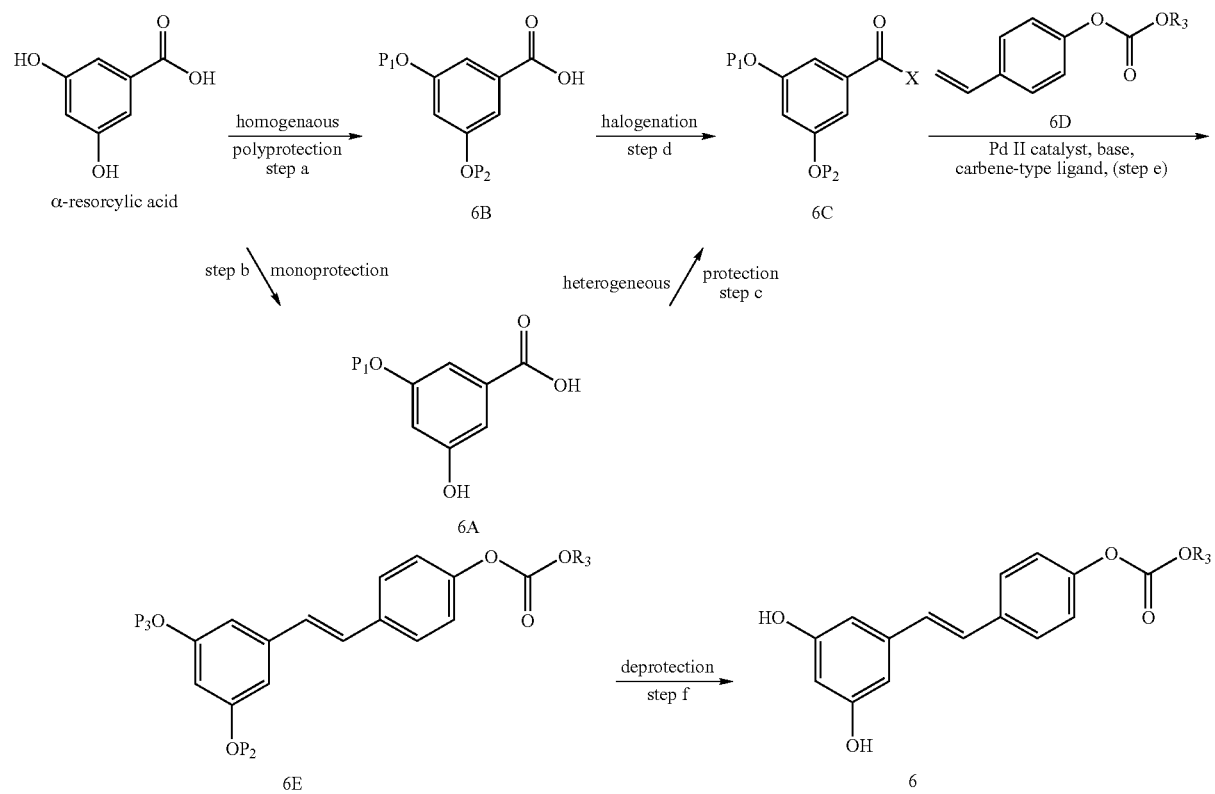

In another preferred embodiment, 4'-ester compounds of Formula 6, pharmaceutically and cosmetically acceptable salts thereof wherein $R_3$ is selected from alkyl with at least one carbon atom, aryl, aralkyl, and diastereoisomers of the foregoing, are synthesized from the steps of a, b (or in the alternative c and d), e, f, and g: wherein step a) is esterifying 4-hydroxy styrene with an esterifying agent in solution or in suspension of a first solvent to give the 4-ester styrene of Formula 6D; step b) is reacting resorcylic acid with an alcohol protecting agent in solution or in suspension of a second solvent to give a compound of Formula 6B; wherein $P_1$ is a first alcohol protecting group and $P_2$ is a second alcohol protecting group; step c) reacting resorcylic acid with a first alcohol protecting agent in solution or in suspension of a second solvent to give a compound of Formula 6A; step d) is reacting a compound of Formula 6A with a second alcohol protecting agent in solution or in suspension of a third solvent to give a compound of Formula 6B where $P_1$ and $P_2$ are different; step e) is halogenating said compound of Formula 6B using a halogenating agent in solution or in suspension of a fourth solvent to give the acid halide of Formula 6C, wherein X is halogen; step f) is coupling said compound of Formula 6D with a compound of Formula 6C with Pd II catalyst, N-heterocyclic carbene-type ligand, and a first base in solution or in suspension of a fifth solvent to yield a compound of Formula 6E; and, step e) is deprotecting said first alcohol protecting group from said compound of Formula 6D to give a compound of Formula 6. In some embodiments R is alkyl with at least two carbon atoms.

Compounds of the invention are those prepared by the above process.

Returning to Scheme 7, the general procedure for the preparation of the compounds of Formula 6 is shown. The compounds of Formula 6 may be generally characterized as the 4'-esters of resveratrol, that is, the phenolic hydroxyls at the 3 and 5 positions are free alcohols while the phenolic hydroxyl at the 4' position is an ester.

The 4'-esters of resveratrol are prepared by reacting resorcylic acid with two or more equivalents of a suitable protecting agent. The diprotected acid is halogenated to a corresponding acid halide. A 4-ester styrene is made by reacting 4-hydroxystyrene with a desired esterifying agent. The 4-ester styrene is reacted with the protected acid halide in a decarbonylative Heck reaction as described above. After coupling, the protection groups at the 3 and 5 positions are removed to give the 4'-ester of resveratrol.

Selective 3,5,4'-Triesters of Resveratrol

Selective 3,5,4'-triester derivatives of resveratrol may also be prepared by the process depicted in Scheme 8.

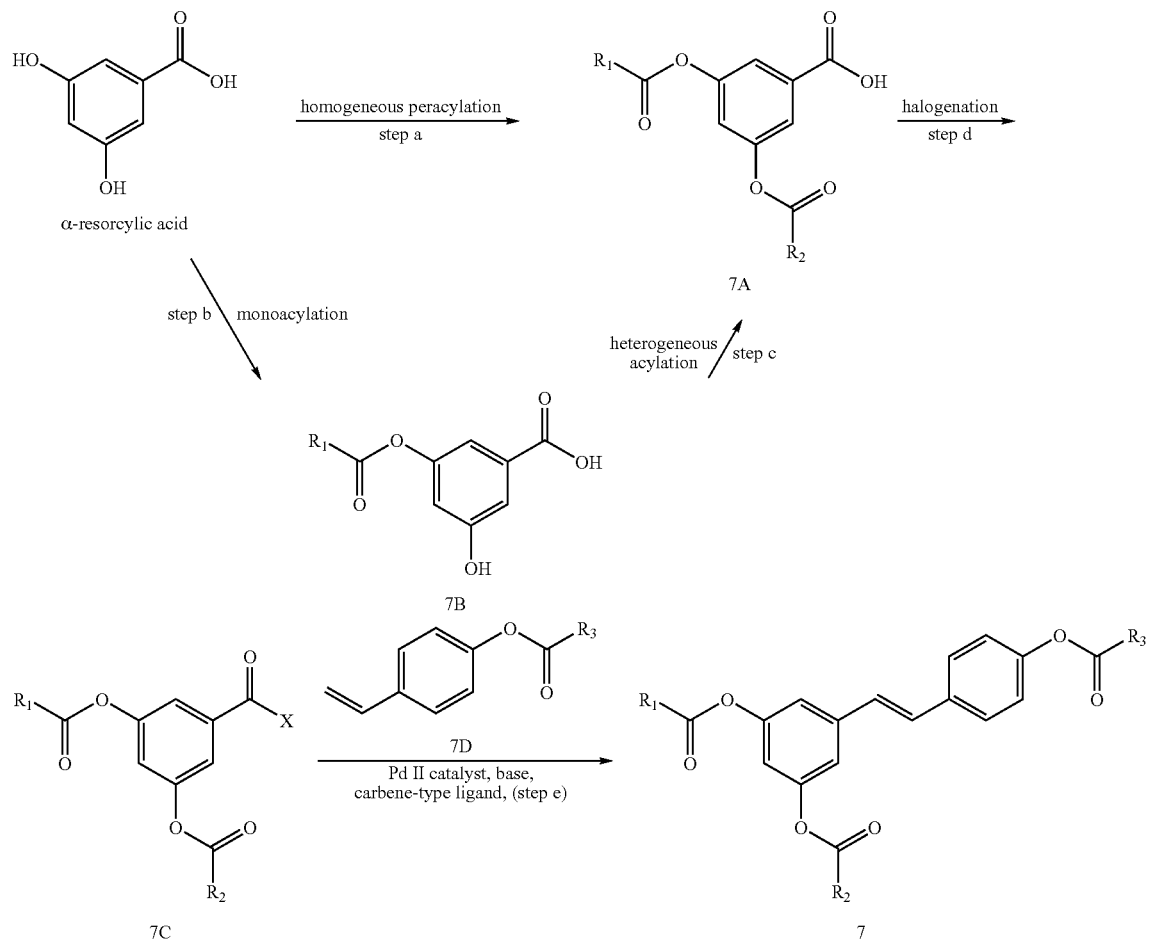

In another preferred embodiment, 3,5,4'-triester compounds of Formula 7, pharmaceutically and cosmetically acceptable salts thereof wherein $R_1$, $R_2$ and $R_3$ are independently selected from alkyl with at least one carbon atom, aryl, aralkyl, and diastereoisomers of the foregoing, are synthesized from the steps of a (or alternatively b and c), d, e, f, and g: wherein step a) is esterifying resorcylic acid with an esterifying agent in solution or in suspension of a first solvent to give the 3,5-diester of resorcylic acid of Formula 7A; step b) is esterifying resorcylic acid with a first esterifying agent in solution or in suspension of a first solvent to give the 3-ester of Formula 7B step c) is esterifying said compound of Formula 7B with a second esterifying agent in solution of in suspension of a second solvent to give the 3,5-diester of Formula 7A where $R_1$ and $R_2$ are different; step d) is halogenating said compound of Formula 7A using a halogenating agent in solution or in suspension of a third solvent to give the acid halide of Formula 7C, wherein X is halogen; step e) is coupling said compound of Formula 7D with a compound of Formula 7C with Pd II catalyst, N-heterocyclic carbene-type ligand, and a first base in solution or in suspension of a fourth solvent to yield said compound of Formula 7. In some embodiments R is alkyl with at least two carbon atoms.

Compounds of the invention are those prepared by the above process.

Returning to Scheme 8, the general procedure for the preparation of the compounds of Formula 7 is shown. The compounds of Formula 7 may be generally characterized as the 3,5,4'-triesters of resveratrol, that is, the phenolic hydroxyls at the 3,5,4' positions are esters.

The 3,5,4'-triesters of resveratrol are prepared by reacting resorcylic acid with two or more equivalents of a desired esterifying agent. The diesterified resorcylic acid is halogenated to a corresponding acid halide. A 4-ester styrene is made by reacting 4-hydroxystyrene with a desired esterifying agent. The 4-ester styrene is reacted with the diesterified acid halide in a decarbonylative Heck reaction as described above to give the 3,5,4'-triester of resveratrol.

Preparation of Resveratrol Esters

The processes described to produce the 3-esters, 3,5-diesters, 3,4'-diesters, 4'-esters, and 3,5,4'-triesters of resveratrol can be used to produce resveratrol itself by augmenting the respective processes with an additional step: hydrolysis with an alkaline earth hydroxide or alkaline earth alkoxide in a polar aprotic solvent followed by acidification.

Preferred Compounds

Compounds of the invention are those prepared by the processes above, especially those selected from: 5,4'-dihydroxy-3-acetoxy stilbene (3-acetoxy resveratrol), 3,5-dihydroxy-4'-acetoxy stilbene (4'-acetoxy resveratrol), 3,4'-dihydroxy-5-acetoxy stilbene (5-acetoxy resveratrol), 4'-hydroxy-3,5-diacetoxy stilbene (3,5-diacetoxy resveratrol), 5-hydroxy-3,4'-diacetoxy stilbene (3,4'-diacetoxy resveratrol), 3,5,4'-triacetoxy stilbene (3,5,4'-triacetoxy resveratrol); 5,4'-dihydroxy-3-propanoate stilbene, 3,5-dihydroxy-4'-propanoate stilbene, 3,4'-dihydroxy-5-propanoate stilbene, 4'-hydroxy-3,5-dipropanoate stilbene, 5-hydroxy-3,4'-dipropanoate stilbene, 3,5,4'-tripropanoate stilbene; 5,4'-dihydroxy-3-butanoate stilbene, 3,5-dihydroxy-4'-butanoate stilbene, 3,4'-dihydroxy-5-butanoate stilbene, 4'-hydroxy-3,5-dibutanoate stilbene, 5-hydroxy-3,4'-dibutanoate stilbene, 3,5,4'-tributanoate stilbene; 5,4'-dihydroxy-3-pentanoate stilbene, 3,5-dihydroxy-4'-pentanoate stilbene, 3,4'-dihydroxy-5-pentanoate stilbene, 4'-hydroxy-3,5-dipentanoate stilbene, 5-hydroxy-3,4'-dipentanoate stilbene, 3,5,4'-tripentanoate stilbene; 5,4'-dihydroxy-3-hexanoate stilbene, 3,5-dihydroxy-4'-hexanoate stilbene, 3,4'-dihydroxy-5-hexanoate stilbene, 4'-hydroxy-3,5-dihexanoate stilbene, 5-hydroxy-3,4'-dihexanoate stilbene, 3,5,4'-trihexanoate stilbene; sorbic fatty acid derivatives including but not limited to: 5,4'-dihydroxy-3-(2,4-hexadienoate) stilbene, 3,5-dihydroxy-4'-(2,4-hexadienoate) stilbene, 3,4'-dihydroxy-5-(2,4-hexadienoate) stilbene, 4'-hydroxy-3,5-di-(2,4-hexadienoate) stilbene, 5-hydroxy-3,4'-di-(2,4-hexadienoate) stilbene, 3,5,4'-tri-(2,4-hexanoate) stilbene; lauric fatty acid derivatives including but not limited to: 5,4'-dihydroxy-3-dodecanoate stilbene, 3,5-dihydroxy-4'-dodecanoate stilbene, 3,4'-dihydroxy-5-dodecanoate stilbene, 4'-hydroxy-3,5-didodecanoate stilbene, 5-hydroxy-3,4'-didodecanoate stilbene, 3,5,4'-tridodecanoate stilbene; palmitic fatty acid derivatives including but not limited to: 5,4'-dihydroxy-3-hexadecanoate stilbene, 3,5-dihydroxy-4'-hexadecanoate stilbene, 3,4'-dihydroxy-5-hexadecanoate stilbene, 4'-hydroxy-3,5-dihexadecanoate stilbene, 5-hydroxy-3,4'-dihexadecanoate stilbene, 3,5,4'-trihexadecanoate stilbene; stearic fatty acid derivatives including but not limited to: 5,4'-dihydroxy-3-octadecanoate stilbene, 3,5-dihydroxy-4'-octadecanoate stilbene, 3,4'-dihydroxy-5-octadecanoate stilbene, 4'-hydroxy-3,5-dioctadecanoate stilbene, 5-hydroxy-3,4'-octadecanoate stilbene, 3,5,4'-trioctadecanoate stilbene; oleic fatty acid derivatives including but not limited to: 5,4'-dihydroxy-3-(9-octadecenoate) stilbene, 3,5-dihydroxy-4'-(9-octadecenoate) stilbene, 3,4'-dihydroxy-5-(9-octadecenoate) stilbene, 4'-hydroxy-3,5-di-(9-octadecenoate) stilbene, 5-hydroxy-3,4'-di-(9-octadecenoate) stilbene, 3,5,4'-tri-(9-octadecenoate) stilbene; linoleic fatty acid derivatives including but not limited to: 5,4'-dihydroxy-3-(9,12-octadecadienoate) stilbene, 3,5-dihydroxy-4'-(9,12-octadecadienoate) stilbene, 3,4'-dihydroxy-5-(9,12-octadecadienoate) stilbene, 4'-hydroxy-3,5-di-(9,12-octadecadienoate) stilbene, 5-hydroxy-3,4'-di-(9,12-octadecadienoate) stilbene, 3,5,4'-tri-(9,12-octadecadienoate) stilbene; linolenic fatty acid derivatives including but not limited to: 5,4'-dihydroxy-3-(6,9,12-octadecatrienoate) stilbene, 3,5-dihydroxy-4'-(6,9,12-octadecatrienoate) stilbene, 3,4'-dihydroxy-5-(6,9,12-octadecatrienoate) stilbene, 4'-hydroxy-3,5-di-(6,9,12-octadecatrienoate) stilbene, 5-hydroxy-3,4'-di-(6,9,12-octadecatrienoate) stilbene, 3,5,4'-tri-(6,9,12-octadecatrienoate) stilbene; linolenic fatty acid derivatives including but not limited to: 5,4'-dihydroxy-3-(9,12,15-octadecatrienoate) stilbene, 3,5-dihydroxy-4'-(9,12,15-octadecatrienoate) stilbene, 3,4'-dihydroxy-5-(9,12,15-octadecatrienoate) stilbene, 4'-hydroxy-3,5-di-(9,12,15-octadecatrienoate) stilbene, 5-hydroxy-3,4'-(9,12,15-octadecatrienoate) stilbene, 3,5,4'-tri-(9,12,15-octadecatrienoate) stilbene; α-linolenic fatty acid derivatives including but not limited to: 5,4'-dihydroxy-3-(3,6,9-octadecatrienoate) stilbene, 3,5-dihydroxy-4'-(3,6,9-octadecatrienoate) stilbene, 3,4'-dihydroxy-5-(3,6,9-octadecatrienoate) stilbene, 4'-hydroxy-3,5-dihydroxy-(3,6,9-octadecatrienoate) stilbene, 5-hydroxy-3,4'-di-(3,6,9-octadecatrienoate) stilbene, 3,5,4'-tri-(3,6,9-octadecatrienoate) stilbene; arachidonic fatty acid derivatives including but not limited to: 5,4'-dihydroxy-3-(5,8,11,14-eicosatetraenoate) stilbene, 3,5-dihydroxy-4'-(5,8,11,14-eicosatetraenoate) stilbene, 3,4'-dihydroxy-5-(5,8,11,14-eicosatetraenoate) stilbene, 4'-hydroxy-3,5-di-(5,8,11,14-eicosatetraenoate) stilbene, 5-hydroxy-3,4'-di-(5,8,11,14-eicosatetraenoate) stilbene, 3,5,4'-tri-(5,8,11,14-eicosatetraenoate) stilbene; eicosapenatoic fatty acid derivatives including but not limited to: 5,4'-dihydroxy-3-(5,8,11,14,17-eicosapentaenoate) stilbene, 3,5-dihydroxy-4'-(5,8,11,14,17-eicosapentaenoate) stilbene, 3,4'-dihydroxy-5-(5,8,11,14,17-eicosapentaenoate) stilbene, 4'-hydroxy-3,5-di-(5,8,11,14,17-eicosapentaenoate) stilbene, 5-hydroxy-3,4'-di-(5,8,11,14,17-eicosapentaenoate) stilbene, 3,5,4'-tri-(5,8,11,14,17-eicosapentaenoate) stilbene; docosahexanoic fatty acid derivatives including but not limited to: 5,4'-dihydroxy-3-(4,7,10,13,16,19-docosahexaenoate) stilbene, 3,5-dihydroxy-4'-(4,7,10,13,16,19-docosahexaenoate) stilbene, 3,4'-dihydroxy-5-(4,7,10,13,16,19-docosahexaenoate) stilbene, 4'-hydroxy-3,5-di-(4,7,10,13,16,19-docosahexaenoate) stilbene, 5-hydroxy-3,4'-di-(4,7,10,13,16,19-docosahexaenoate) stilbene, and 3,5,4'-tri-(4,7,10,13,16,19-docosahexaenoate) stilbene.

Compounds of the invention are also those esters of resorcylic acid halide useful for decarbonylative Heck reactions described above, especially those selected from: 3,5-diacetoxybenzoyl chloride, 3,5-diacetoxybenzoyl bromide, 3,5-diacetoxybenzoyl iodide, 3,5-dipropanoate benzoyl chloride, 3,5-dipropanoate benzoyl bromide, 3,5-diproponate benzoyl iodide, 3,5-dibutanoate benzoyl chloride, 3,5-dibutanoate benzoyl bromide, 3,5-dibutanoate benzoyl iodide, C5: 3,5-dipentanoate benzoyl chloride, 3,5-dipentanoate benzoyl bromide, 3,5-dipentanoate benzoyl iodide, C6: 3,5-dihexanoate benzoyl chloride, 3,5-dihexanoate benzoyl bromide, 3,5-dihexanoate benzoyl iodide, sorbic: 3,5-dihexadienoate benzoyl chloride, 3,5-dihexadienoate benzoyl bromide, 3,5-dihexadienoate benzoyl iodide, lauric: 3,5-didodecanoate benzoyl chloride, 3,5-didodecanoate benzoyl bromide, 3,5-didodecanoate benzoyl iodide, palmitic: 3,5-dihexadecanoate benzoyl chloride, 3,5-dihexadecanoate benzoyl bromide, 3,5-dihexadecanoate benzoyl iodide, stearic: 3,5-dioctadecanoate benzoyl chloride, 3,5-dioctadecanoate benzoyl bromide, 3,5-dioctadecanoate benzoyl iodide, oleic: 3,5-di-(9-octadecenoate) benzoyl chloride, 3,5-di-(9-octadecenoate) benzoyl bromide, 3,5-di-(9-octadecenoate) benzoyl iodide, linoleic: 3,5-di-(9,12-octadecadienoate) benzoyl chloride, 3,5-di-(9,12-octadecadienoate) benzoyl bromide, 3,5-di-(9,12-octadecadienoate) benzoyl iodide, linolenic: 3,5-di-(6,9,12-octadecatrienoate) benzoyl chloride, 3,5-di-(6,9,12-octadecatrienoate) benzoyl bromide, 3,5-di-(6,9,12-octadecatrienoate) benzoyl iodide, 3,5-di-(9,12,15-octadecatrienoate) benzoyl chloride, 3,5-di-(9,12,15-octadecatrienoate) benzoyl bromide, 3,5-di-(9,12,15-octadecatrienoate) benzoyl iodide, α-linolenic: 3,5-di-(3,6,9-octadecatrienoate) benzoyl chloride, 3,5-di-(3,6,9-octadecatrienoate) benzoyl bromide, 3,5-di-(3,6,9-octadecatrienoate) benzoyl iodide, arachidonic: 3,5-di-(5,8,11,14-eicosatetraenoate) benzoyl chloride, 3,5-di-(5,8,11,14-eicosatetraenoate) benzoyl bromide, 3,5-di-(5,8,11,14-eicosatetraenoate) benzoyl iodide, eicosapenatoic: 3,5-di-(5,8,11,14,17-eicosapentaenoate) benzoyl chloride, 3,5-di-(5,8,11,14,17-eicosapentaenoate) benzoyl bromide, 3,5-di-(5,8,11,14,17-eicosapentaenoate) benzoyl iodide, docosahexanoic: 3,5-di-(4,7,10,13,16,19-docosahexaenoate) benzoyl chloride, 3,5-di-(4,7,10,13,16,19-docosahexaenoate) benzoyl bromide, and 3,5-di-(4,7,10,13,16,19-docosahexaenoate) benzoyl iodide.

In yet another aspect of the invention, a compound of Formula I may be made where each Y and each Z is independently selected from —O (ethers and heterocyclic rings), —O—C=O (esters), —O—C=O—O (carbonates), —O—C=O—NH, —O—C=O—NR, —NH—C=O—O, —NR—C=O—O (carbamates), —NH—C=O, —NR—C=O, —C=O—NH, —C=O—NR (primary and secondary amides)-NH, —NR (primary and secondary amines), —N (heterocyclic rings), —S (heterocyclic rings), and halogen, each n and each m is independently the value of 0, 1, 2, 3, 4 or 5, where each A and each B is independently selected from H, R or absent, where each V and each W is independently selected from H, straight or branched alkyl of from 1 to 6 carbon atoms and cycloalkyl of from 3 to 8 carbon atoms, alkoxy, phenyl, benzyl or halogen, and where R is independently selected from the group comprising alkyl with at least one carbon atom, aryl and aralkyl, and includes diastereoisomers of the foregoing.

Scheme 9 illustrates the general procedure for the preparation of the compounds of Formula I where each A and each B are independently selected from the group comprising alkyl with at least one carbon atom, aryl, aralkyl, $P_n$, $P_m$ (wherein $P_n$ and $P_m$ are each a protecting group), and H. It should be appreciated that with regard to compounds of Formulas IB, IC, ID, IE, and IF, A and B do not represent H; and, with regard to compounds of Formula IA and IE, when any Y and any Z is halogen, A or B is absent. In some embodiments A and B is alkyl with at least two carbon atoms. In some embodiments the sum of m and n is greater than or equal to one but less than nine. In other embodiments the sum of m and n is three or more but less than nine.

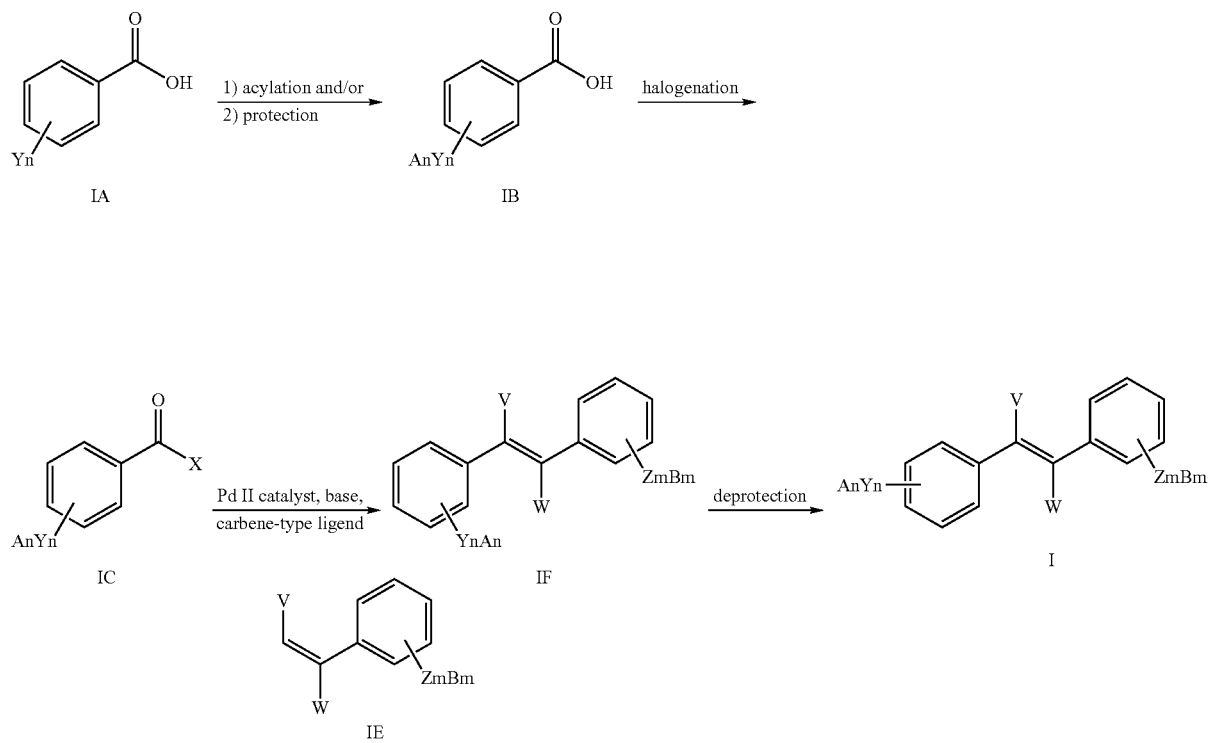

Scheme 9.

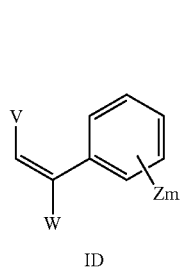

ID

Protection/Acylation of Benzoic Acid Halide Coupling Partner

As depicted in Scheme 9, the benzoic acid derivative IA is optionally acylated and/or optionally protected with a desired number and type of acyl group(s) equal to or less than n and/or with the desired number and type of protecting group(s) equal to or less than n to yield benzoic acid derivative IB where A is selected from the group comprising alkyl with at least one carbon atom, aryl, aralkyl, and $P_n$.

A variety of reaction pathways starting with benzoic acid derivative IA can be used to obtain the benzoic acid derivative IB. These include homogenous peracylation or polyacylation (condition I), homogenous polyprotection (condition II), selective acylation followed by selective protection (condition III), selective protection followed by selective acylation (condition IV), heterogeneous peracylation (condition V), heterogeneous polyprotection (condition VI), selective acylation followed by homogeneous or heterogeneous polyprotection (condition VII) and selective protection followed by homogeneous or heterogeneous peracylation (condition IIX). It is contemplated that under condition VII, selective acylation may occur at one or more substituent sites and polyprotection may occur at one or more substituents sites. In like manner, it is contemplated that under condition IIX, selective protection may occur at one or more substituent sites and peracylation may occur at one or more substituents sites. When each Y or each Z is halogen, the acylation and/or protection and diprotection steps may be entirely omitted. Where one or more of Y and Z are halogen and one or more of Y and Z is neither H nor halogen, the acylation and/or protection and diprotection steps may be implemented.

It is to be understood from this description that benzoic acid IA includes benzoic acid and monohydroxyl benzoic acids, dihydroxyl benzoic acids, trihydroxyl benzoic acids, tetrahydroxyl benzoic acids, and pentahydroxyl benzoic acids.

Benzoic acid IA also includes the monoamino benzoic acids 2-amino benzoic acid (anthranilic acid), 3-amino benzoic acid and 4-amino benzoic acid (Vitamin $H_1$) in which case only conditions I or II can apply. Benzoic acid IA also includes but is not limited to the diamino benzoic acids 2,3-diamino benzoic acid, 2,4-diamino benzoic acid, 3,4-diamino benzoic acid, 3,5-diamino benzoic acid in which case conditions I-VI can apply. Benzoic acid IA also includes but is not limited to the monohydroxyl-monoamino benzoic acids. Illustrative examples of which include but are not limited to 2-amino-5-hydroxy benzoic acid (5-hydroxyanthranilic acid), 3-amino-4-hydroxy benzoic acid, 4-amino-3-hydroxy benzoic acid, 3-amino-2-hydroxy benzoic acid (3-aminosalicylic acid), 4-amino-2-hydroxy benzoic acid (4-aminosalicylic acid) and 5-amino-2-hydroxybenzoic acid (5 aminosalicylic acid) in which case conditions I-VI can apply.

By way of illustration, the 3,5-diaminobenzoic acid analogs of IA, where n=2 and each Y is $NH_2$, the amines can be 1) both acylated with one or more acylating agents (condition I), 2) both protected with a one or more protecting agents (condition II), 3) selectively acylated with an acylating agent and selectively protected with a protecting agent (condition III), 4) selectively protected with a protecting agent and selectively acylated with an acylating agent (condition IV), 5) heterogeneous diacylated with both amines acylated with two different acylating agents (condition V), or 6) heterogeneous diprotection with both amines protected with two different protecting agents (condition VI).

In the example of diacylation (condition I), both amines are reacted with at least 2 equivalents of an acylating agent in a basic solvent (or in an inert solvent with added base) to give the diamide 3,5-diaminobenzoic acid derivative $IB_a$ where $A_1$ and $A_2$ are the same. Preferably, a 5 molar equivalent excess of the acylating agent is used.

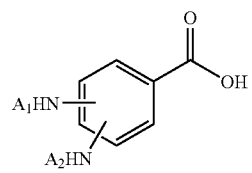

IBa

In the example of diprotection (condition II), both amines are reacted with at least 2 equivalents of a protection agent and under conditions known to one skilled in the art for the desired amine protecting group to give the diprotected 3,5-diaminobenzoic acid derivative $IB_a$ where $A_1$ and $A_2$ are the same.

In the example of selective acylation followed by selective protection (condition III), 3,5-diaminobenzoic acid is first reacted with 1 equivalent or more of an acylating agent in a basic solvent (or in an inert solvent with added base) to give 3,5-diaminobenzoic acid derivative $IB_b$ where $NHA_1$ represents an amide. Intermediate $IB_b$ is then reacted with 1 equivalent or more of a protection agent and under conditions known to one skilled in the art for the desired amine protecting group to give 3,5-diaminobenzoic acid derivative $IB_a$ where $NHA_2$ represents a protected amine.

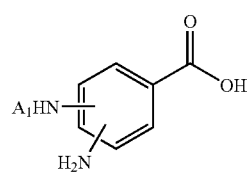

IBb

In the example of selective protection followed by selective acylation (condition IV), 3,5-diaminobenzoic acid is first reacted with 1 equivalent or more of a protection agent and under conditions known to one skilled in the art for the desired amine protecting group to give 3,5-diaminobenzoic acid derivative $IB_b$ where $NHA_1$ represents a protected amine. Intermediate $IB_b$ is then reacted with 1 equivalent or more of an acylating agent in a basic solvent (or in an inert solvent with added base) to give 3,5-diaminobenzoic acid derivative $IB_a$ where $NHA_2$ represents an amide.

In the example of heterogeneous diacylation (condition V), 3,5-diaminobenzoic acid is first reacted with 1 equivalent or more of a first acylating agent in a basic solvent (or in an inert solvent with added base) to give 3,5-diaminobenzoic acid derivative $IB_b$ where $NHA_1$ represents a first amide. Intermediate $IB_b$ is then reacted with 1 equivalent or more of a second acylating agent to give 3,5-diaminobenzoic acid derivative $IB_a$ where $NHA_2$ represents a second amide.

In the example of heterogeneous diprotection (condition VI), 3,5-diaminobenzoic acid is first reacted with 1 equivalent or more of a first protection agent under conditions known to one skilled in the art for the desired amine protecting group to give 3,5-diaminobenzoic acid derivative $IB_b$ where $NHA_1$ represents a first protected amine. Intermediate $IB_b$ is then reacted with 1 equivalent or more of a second protecting agent to give 3,5-diaminoebenzoic acid derivative $1B_a$ where $NHA_2$ represents a second protected amine.

Suitable acylating agents useful in the step or steps described above include those previously described for esterification. In the examples where acylation results in an amide (i.e. Y and/or Z is $NH_2$), acylation is followed by treatment with aqueous mild acid such as formic acid and optionally by recrystallization. Suitable protecting groups are described in T. W. Greene, Protective Groups in Organic Synthesis, John Wiley & Sons, New York, N.Y., 1991, 2nd Edition.

Preferred amine protecting groups are those that can be selectively cleaved over a phenyl amine and include tert-butyloxycarbonyl (BOC), fluorinomethyloxycarbonyl (FMOC), and benzyloxycarbonyl (Cbz).

Halogenation of Acid Chloride Coupling Partner

Returning to Scheme 9, benzoic acid derivative IB is reacted with a halogenating agent in an inert solvent to yield the benzoic acid halide derivative IC where X is any halogen.

Suitable halogenating agents useful in this step include but are not limited to any of the halogenating agents known to the art, such as thionyl halides including thionyl chloride, thionyl bromide and thionyl iodide, oxalyl halides including oxalyl chloride, oxalyl bromide and oxalyl iodide, phosphorous tri- and pentahalides and phosphorous oxyhalides. Halogenation is carried out in an inert solvent including but not limited to halogenated alkanes such as methylene chloride and chloroform; cyclic ethers, such as THF and dioxane; N,N-dialkyl-substituted acylamides, such as DMF and DMAC; and mixtures of said solvents.

The halogenation reaction may optionally include a buffering agent capable of associating with HX acid. Suitable buffering agents include weak bases. Benzotriazole is a preferred buffering agent during halogenation because it precipitates as a salt after reacting with a HX acid.

The reaction is effected at a temperature from about 0 to about 100° C. Preferably, the reaction is effected using thionyl chloride or oxalyl chloride in a polar solvent such as methylene chloride, at 80° C., in the presence of benzotriazole to yield the corresponding acid chloride.

Optionally, the intermediate IC is recrystallized from hexane.

Preparation of Styrene Coupling Partner

Also depicted in Scheme 9 is styrene derivative ID. A variety of reaction pathways starting with styrene derivative ID can be used to obtain the styrene derivative IE. These pathways include homogenous peracylation or polyacylation (condition I), homogenous polyprotection (condition II), selective acylation followed by selective protection (condition III), selective protection followed by selective acylation (condition IV), heterogeneous peracylation (condition V), heterogeneous polyprotection (condition VI), selective acylation followed by homogeneous or heterogeneous polyprotection (condition VII) and selective protection followed by homogeneous or heterogeneous peracylation (condition IIX). It is contemplated that under condition VII, selective acylation may occur at one or more substituent sites and polyprotection may occur at one or more substituents sites. In like manner, it is contemplated that under condition IIX, selective protection may occur at one or more substituent sites and peracylation may occur at one or more substituents sites.

It is to be understood from this description that styrene derivative IA includes styrene and the monohydroxyl styrenes, dihydroxyl styrenes, trihydroxyl styrenes, tetrahydroxyl styrenes, and pentahydroxyl styrenes.

Styrene derivative ID also includes the monoamino styrenes 2-amino styrene, 3-amino styrene and 4-amino styrene in which case only conditions I or II can apply. Styrene derivative ID also includes but is not limited to the diamino styrenes 2,3-diamino styrene, 2,4-diamino styrene, 3,4-diamino styrene, 3,5-diamino styrene in which case conditions I-VI can apply.

Styrene derivative ID also includes but is not limited to the monohydroxyl-monoamino styrenes. Illustrative examples of which include but are not limited to 2-amino-5-hydroxy styrene, 3-amino-4-hydroxy styrene, 4-amino-3-hydroxy styrene, 3-amino-2-hydroxy styrene, 4-amino-2-hydroxy styrene and 5-amino-2-hydroxystyrene in which case conditions I-VI can apply.

By way of illustration, the monoamino styrene analogs of ID (where n=1 and Z is $NH_2$) has one amine that can be 1) acylated with an acylating agent (condition I) or 2) protected with a protecting agent (condition II).

Coupling Step Via Decarbonylative Heck Reaction

Returning to Scheme 9, benzoic acid halide IC is reacted with styrene IE via a decarbonylative coupling reaction to give stilbene IF. The reaction conditions associated with the coupling reaction can include an inert apolar, high-boiling point aromatic or hydrocarbon solvent with a transition metal catalyst, N-heterocyclic carbene-type ligand and base.

Suitable inert solvents useful in the coupling step include but are not limited to benzene, toluene, xylene, chlorobenzne, decane, dodecane, and mixtures of those solvents. Xylene is a preferred solvent in the coupling step.

A preferred transition metal catalyst used in the coupling step is $Pd(OAc)_2$.

A preferred N-heterocyclic carbene-type ligands useful in the coupling step is N,N-bis-(2,6-diisopropylphenyl) 4,5-dihydroimidazolium chloride in an amount of 0.1-10 mol %, preferably 5-10 mol %.

Non-coordinating amine bases result in greater yields than coordinating amine bases. Examples of non-coordinating bases useful in the process include but are not limited to N-ethylmorpholine (NEM), N,N-dimethylbenzylamine, dimethylaminopyridine (DMAP), proton sponge (1,8-diaminonaphthalene), diisopropylethylamine (Hunig's base) and triethylamine. N-ethylmorpholine and N,N-dimethylbenzylamine are preferred bases in the coupling step. Use of smaller amines capable of transition metal coordination still work to obtain the coupled product IF but are less efficient. Furthermore, phosphine ligands can also be added to the reaction; however, added phosphine ligand inhibits the reaction giving greatly lowered yields.

The reaction is effected at a temperature from about 0 to about 150° C. Preferably, the reaction is refluxed in xylene.

The decarbonylative Heck reaction depicted in Scheme 9 is concluded using standard work-up conditions and the reaction products can be purified using a variety of techniques known to those skilled in the art including silica gel chromatography.

Deprotection Step

After performing the coupling reaction, in those cases where one or more protecting groups exist on the stilbene derivative IF, the protection groups may be deprotected as described in T. W. Greene, Protective Groups in Organic Synthesis, John Wiley & Sons, New York, N.Y., 1991, 2nd Edition for each of the respective protection groups and may require one or more steps to complete.

In the example of stilbene derivatives IF akin to resveratrol, where Y=$NH_2$ at the 3 and 5 positions, n=2, Z=$NH_2$ at the 4' position and m=1, the derivative may be 1) deacylated at all three amine sites (3,5, and 4'), 2) deprotected and/or deacylated at all three amine sites and 3) selectively deprotected at any of the three amine sites.

Olefin Isomerization

As discussed previously, the stilbene compounds of the present invention possess a conjugated double bond. The double bond may exist in the cis or trans configuration. When V and W are H, the decarbonylative Heck reaction yields a trans product. However, depending on the nature of the V and W substitutions (i.e. other than H), the decarbonylative Heck reaction of the present invention may yield a cis or trans product. The present invention includes both cis and trans isomers as mixtures or in purified form. Furthermore, one aspect of the present invention includes a process for isomerizing between the cis and trans configurations. As depicted in Scheme 10, the isomerization step may be conducted to the stilbene derivatives when Y is acylated, protected, or hydrolyzed. Compounds of Formula I can be diluted in an inert solvent and irradiated with ultraviolet light, preferably of wavelength λ=280-350 nm. This ultraviolet irradiation is carried in organic solution, at temperatures of 0° to 50°, preferably of 10° to 30°. The irradiation can be carried out with the aid of the most diverse commercial ultraviolet apparatuses. By way of example, irradiation can be carried out with a medium-pressure mercury vapor lamp through a pyrex filter. The irradiation time is generally from 2 to 100 hours, preferably 5 to 50 hours, especially 10 to 20 hours.

Scheme 10.

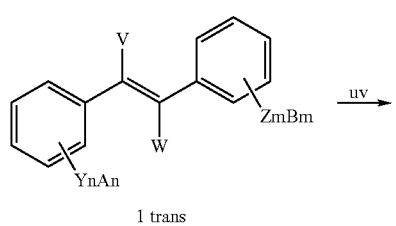

Compounds of Formulas I and 1-7 are capable of further forming both pharmaceutical and cosmetically acceptable formulations.

Pharmaceutical Uses

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula 1 or a corresponding pharmaceutically acceptable salt of a compound of Formula 1.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, table, cachet, or lozenge itself, or it can be the appropriate number of any of these in packaged form.

The quantity of active component in a unit dose preparation may be varied or adjusted from 0.1 mg to 1000 mg preferably 0.5 mg to 100 mg according to the particular application and the potency of the active component. The composition can, if desired, also contain other compatible therapeutic agents.

Cosmetic Uses

For preparing cosmetic compositions from the processes and compounds of the present invention, cosmetically acceptable vehicles or carriers facilitate distribution when the composition is applied to the skin. The vehicle may be aqueous, anhydrous or an emulsion. Preferably, the compositions are aqueous or an emulsion, especially water-in-oil or oil-in-water emulsion. Water when present will be in amounts which may range from 5 to 99%, preferably from 20 to 70%, optimally between 35 and 60% by weight.

Besides water, relatively volatile solvents may also serve as carriers within compositions of the present invention. Most preferred are monohydric $C_1$-$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxones and polyether siloxane copolymers. he essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are: (1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate; (2) ether-esters such as fatty acid esters of ethoxylated fatty alcohols; (3) polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters; (4) wax esters such as beeswax, spermaceti, myristyl myristate, stearyl stearate and arachidyl behenate; and, (5) sterols esters, of which cholesterol fatty acid esters are examples thereof; fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylen polyols and their derivatives, including propylene glycol, dipropylene glycol, polypropylene glycol, polyethylene glycol and derivatives thereof, sorbitol, hydroxypropyl sorbitol, hexylene glycol, 1,3-dibutylene glycol, 1,2,6-trihexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, acyl glutamates, $C_8$-$C_{20}$ alkyl ether phosphates and combinations thereof.

Sunscreens may be present in cosmetic compositions of the present invention. Sunscreens include those materials commonly employed to block ultraviolet light. Illustrative compounds are the derivatives of PABA, cinnamate and salicylate. For example, avobenzophenone (Parsol 1789™) octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation.

Many cosmetic compositions, especially those containing water, must be protected against the growth of potentially harmful microorganisms. Preservatives are, therefore, often necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the composition.

Powders may be incorporated into the cosmetic composition of the invention. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

Cosmetic formulations according to the invention are used in various fields. For example, the following preparations especially come into consideration: skin-care preparations, e.g. skin-washing and cleansing preparations in the form of tablet-form or liquid soaps, synthetic detergents or washing pastes; bath preparations, e.g. liquid (foam baths, milks, shower preparations) or solid bath preparations, e.g. bath cubes and bath salts; skin-care preparations, e.g. skin emulsions, multi-emulsions or skin oils; cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipstick, lip gloss, lip contour pencils, nail-care preparations, such as nail varnish, nail varnish remover, nail hardeners, or cuticle removers; intimate hygiene preparations, e.g. intimate washing lotions or intimate sprays; foot-care preparations, e.g. foot baths, foot powders, foot creams or foot balsams, special deodorants and antiperspirants or callous-removing preparations; light-protective preparations, such as sun milks, lotions, creams, oils, sun blocks or tropicals, pre-tanning preparations or after-sun preparations; skin-tanning preparations, e.g. self-tanning creams; depigmenting preparations, e.g. preparations for bleaching the skin or skin-lightening preparations; insect-repellents, e.g. insect-repellent oils, lotions, sprays or sticks; deodorants, such as deodorant sprays, pump-action sprays, deodorant gels, sticks or roll-ons; antiperspirants, e.g. antiperspirant sticks, creams or roll-ons; preparations for cleansing and caring for blemished skin, e.g. synthetic detergents (solid or liquid), peeling or scrub preparations or peeling masks; hair-removal preparations in chemical form (depilation), e.g. hair-removing powders, liquid hair-removing preparations, cream- or paste-form hair-removing preparations, hair-removing preparations in gel form or aerosol foams; shaving preparations, e.g. shaving soap, foam shaving creams, non-foaming shaving creams, foams, gels, preshave preparations for dry shaving, aftershaves or aftershave lotions; fragrance preparations, e.g. fragrances (eau de Cologne, eau de toilette, eau de parfum, parfum de toilette, perfume), perfume oils or perfume creams; dental-care, denture-care and mouth-care preparations, e.g. toothpastes, gel tooth-pastes, tooth powders, mouthwash concentrates, anti-plaque mouthwashes, denture cleaners or denture fixatives; and, cosmetic hair-treatment preparations, e.g. hair-washing preparations in the form of shampoos and conditioners, hair-care preparations, e.g. pre-treatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hair sprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or camomile.

The compounds of the present invention have significantly improved biological activity and can be stored over a long period without alteration.

The following non-limiting examples illustrate the preferred methods for preparing the compounds of the invention.

Nutritional Uses

When the composition is incorporated into various media such as foods, it may simply be orally ingested. The food can be a dietary supplement (such as a snack or wellness dietary supplement) or, especially for animals, comprise the nutritional bulk (e.g., when incorporated into the primary animal feed).

EXAMPLES

Air and moisture sensitive reagents were introduced via dry syringe or cannula. Toluene, xylene, pyridine, ethyl acetate, and N-methyl morpholine were distilled from $CaH_2$. DMF were dried by storage over 4 Å Molecular sieves. Reagents were purchased from Aldrich and Lancaster. Flash chromatography was carried out using 60-230 mesh silica gel. Radical chromatography was performed using 1, 2, and 4 mm plates loaded with 230-400 mesh PF-254 gypsum bound silica. Analytical thin-layer chromatography (TLC) was performed with Merck silica gel 60 $F_{254}$, 0.25 mm pre-coated TLC plates. TLC plates were visualized using $UV_{254}$. All $^1$H NMR spectra were obtained with 300 Varian spectrometers using TMS (0.00 ppm), Chloroform (7.26 ppm), or acetone-$d_6$ (2.05 ppm) as an internal reference. Signals are reported as m (multiplet), s (singlet), d (doublet), t (triplet), q (quartet), and bs (broad singlet). $^{13}$C NMR were obtained with 75 MHz Varian spectrometer using TMS (0.0 ppm), Chloroform (77.2 ppm), or acetone-$d_6$ (30.6 ppm) as the internal standard. Mass spectra date (HRMS, EI) were obtained from the Brigham Young University mass spectrometry facility. Combustion analysis was performed by M-H-W Laboratories, Phoenix, Ariz.

The following are prepared according to Scheme 11.

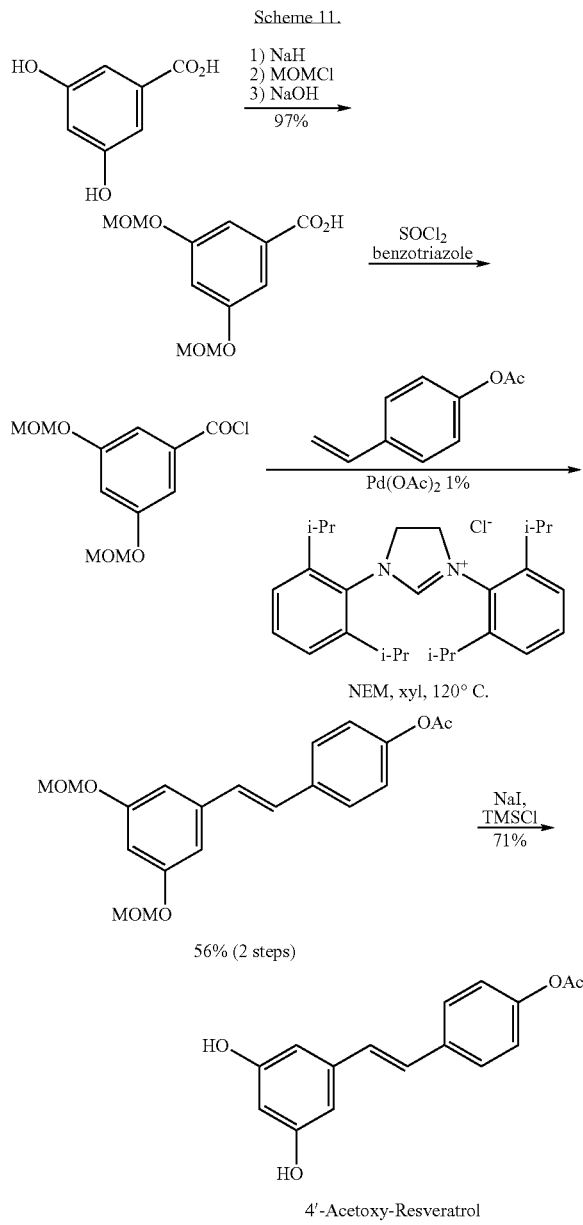

1. Preparation of 3,5-bis(methoxymethoxy)benzoic acid

A flame dried flask was charged with dry DMF (75 mL) and 60% oil dispersion NaH (3.8 g, 95 mmol). A solution of 3,5-dihydroxybenzoic acid (4.6 g, 30 mmol) in DMF (25 mL) was added dropwisely over 20 minutes. The mixture was allowed to stir for one hour under $N_2$. MOMCl (7.5 mL, 100 mmol) was added slowly so that the inner temperature did not exceed 50° C. After 30 hours, the insoluble material was filtered off and the filtrate was concentrated to an oil residue, which was partitioned between benzene and water. The water layer was extracted with benzene for another three times. The combined benzene extracts was dried over $Na_2SO_4$ and concentrated to pale yellow oil, which was dissolved in 50 mL methanol. 2N Aqueous NaOH (25 mL, 50 mmol) was added and the mixture was stirred for three hours. The mixture was concentrated and dissolved in 30 mL water. The aqueous solution was washed with benzene and acidified with 10% aqueous HCl. The precipitated white solid was filtered and washed with water and dried to give 6.6 g (91%) product, which can be further purified by recrystallization from EtOAc-hexane. Data are: $^1$H NMR (CDCl$_3$, 300 MHz) δ 7.44 (d, 2H), 6.98 (t, 1H), 5.21 (s, 4H), 3.50 (s, 6H); $^{13}$C NMR (CDCl$_3$, 75 MHz) δ 170.9, 158.4, 131.4, 111.5, 110.7, 94.7, 56.4; mp=129-130° C.; HRMS (EI$^+$) found 242.0796 M$^+$, calcd 242.0790 for $C_{11}H_{14}O_6$.

2. Preparation of 3,5-bis(methoxymethoxy)benzoyl chloride

A stock solution was prepared by dissolving benzotriazole (1.49 g, 0.0125 mmol), thionyl chloride (0.91 mL, 0.0125 mmol) in 8.0 mL DCM. Reaction was carried out by adding the stock solution intermittently into a stirred solution of 3,5-dimethoxybenzoic acid (2.42 g, 10 mmol) in 200 ml DCM. Before the addition was complete, benzotriazole hydrochloride started precipitating out as white solid. The mixture was stirred for another ten minutes. After filtration, the filtrate was stirred with MgSO$_4$ 7H$_2$O (5 g) to destroy excess thionyl chloride. The white solid was filtered off and the filtrate was concentrated to give 2.5 g (97%) crude product, which was used for the next step without further purification. Data are: $^1$H NMR (CDCl$_3$, 300 MHz) δ 7.44 (d, 2H), 7.04 (t, 1H), 5.20 (s, 4H), 3.49 (s, 6H); $^{13}$C NMR (CDCl$_3$, 75 MHz) δ 168.1, 158.5, 135.3, 112.6, 111.9, 94.7, 56.4; HRMS (EI$^+$) found 260.0465 M$^+$, calcd 260.0452 for $C_{11}H_{13}O_5Cl$.

3. Preparation of 4'-acetoxy-3,5-bis(methoxymethoxy)stilbene

A 50 mL round bottom flask was charged with p-xylene (20 mL), Pd II catalyst (22.5 mg, 0.1 mmol), 1,3-bis-(2,6-diisopropylphenyl)imidazolinium chloride (42.7 mg, 0.1 mmol), 3,5-bis(methoxymethoxy)benzoyl chloride (2.42 g, 10 mmol), 4-acetoxystyrene (1.94 g, 12 mmol), and N-methyl morpholine (1.38 g, 12 mmol). The mixture was stirred at 120° C. for 3.5 h under nitrogen atmosphere. Then it was cooled to room temperature and EtOAc was added and filtered. The filtrate was washed with brine and dried over Na$_2$SO$_4$. Then it was filtered and purified via flash chromatography and gave the product (2.1 g, 59%) as white solid. Data are: $^1$H NMR (CDCl$_3$, 300 MHz) δ 7.48 (d, 2H), 7.08-6.93 (m, 4H), 6.86 (d, 2H), 6.66 (t, 1H), 5.19 (s, 4H), 3.50 (s, 6H), 2.30 (s, 3H); $^{13}$C NMR (CDCl$_3$, 75 MHz) δ 169.5, 158.7, 150.3, 139.5, 135.0, 128.7, 128.5, 127.6, 121.9, 108.0, 104.5, 94.6, 56.2, 21.2; HRMS (EI+) found 358.1409 M+, calcd 358.1416 for $C_{20}H_{22}O_6$.

4. Preparation of 4'-acetoxy-3,5-dihydroxystilbene

To a solution of 4'-acetoxy-3,5-bis(methoxymethoxy)stilbene (0.358 g, 1 mmol) in dry DCM (50 mL) and dry $CH_3CN$ (50 mL) were added NaI (1.8 g, 24 mmol) and freshly distilled TMSCl (1.52 g, 24 mmol). The mixture was stirred under argon for 15 minutes. The solution was diluted with DCM (50 mL) and washed with a fresh aqueous saturated solution of $Na_2S_2O_3$ (3×40 mL) and saturated $NaHCO_3$, and water. The organic layer was dried over $Na_2SO_4$, filtered and concentrated. The crude product was purified by flash column and gave 0.20 g product (72%). Data are: $^1H$ NMR (Aceton-$d_6$, 300 MHz) δ 8.25 (s, 1H), 7.60 (m, 2H), 7.13-7.08 (m, 4H), 6.59 (d, 2H), 6.32 (t, 1H), 2.25 (s, 3H); $^{13}C$ NMR (Aceton-d6, 75 MHz) δ 169.7, 159.7, 151.4, 140.4, 136.0, 130.0, 128.3, 128.3, 123.0, 106.1, 103.3, 21.1; HRMS (EI+) found 270.0889 M+, calcd 270.0892 for $C_{16}H_{16}O_4$.

The following are prepared according to Scheme 12.

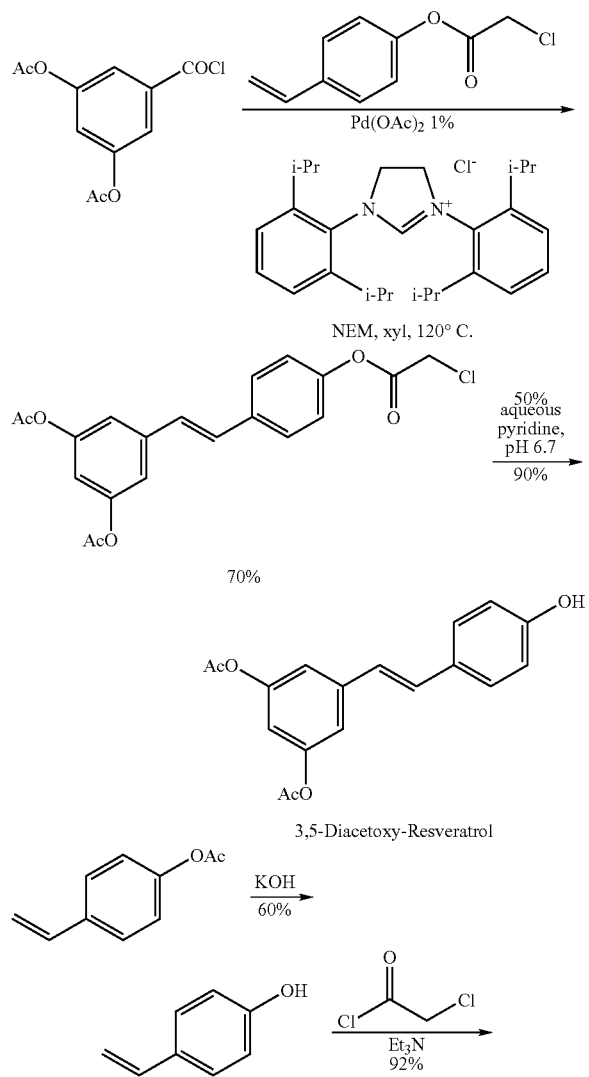

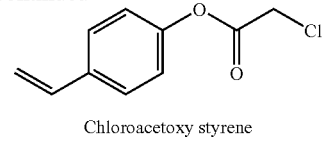

Chloroacetoxy styrene

5. Preparation of 3,5-diacetoxybenzoic acid

To a solution of 3,5-dihydroxybenzoic acid (7.71 g, 50 mmol) in EtOAc (110 mL) were added acetic anhydride (12.25 mL, 130 mmol) and pyridine (8.08 mL, 100 mmol) in an ice-water bath under a nitrogen atmosphere. The mixture was stirred at 0° C. for 40 min and then stirred at ambient temperature for 4 h. 98% Formic acid (2.36 mL, 60 mmol) was added and the resulting mixture was stirred for 1 h. Then, it was poured into water and extracted with EtOAc. The organic phase was washed with water and brine, dried over $Na_2SO_4$, filtered, and evaporated in vacuo. Purification of the residue via recrystallization from n-heptane/EtOAc provided 3,5-diacetoxybenzoic acid (8.97 g, 75.3%) as white solid. Data are: $^1H$ NMR (CDCl$_3$, 300 MHz) δ 12.1 (bs, 1H), 7.73 (d, 2H), 7.21 (t, 1H), 2.32 (s, 6H); $^{13}C$ NMR (CDCl$_3$, 75 MHz) δ 170.4, 169.0, 151.2, 131.5, 121.3, 121.0, 21.2; mp=161-162° C.; HRMS (EI+) found 238.0475 M+, calcd 238.0477 for $C_{11}H_{10}O_6$; Anal. Calcd for $C_{11}H_{10}O_6$: C, 55.47; H, 4.23. Found: C, 55.62; H, 4.37.

6. Preparation of 3,5-diacetoxybenzoyl chloride

To a mixture of 3,5-diacetoxybenzoic acid (8.00 g, 33.59 mmol) and dimethylformamide (5 drops) in toluene was added freshly distilled thionylchloride (16 mL). The mixture was stirred for 15 min under nitrogen atmosphere at ambient temperature. Then it was refluxed for 2 h at 80° C. in a hot water bath. The excess thionyl chloride was evaporated in vacuo and toluene was added. Insoluble yellow solid was discarded. Toluene was evaporated in vacuo and gave 3,5-diacetoxybenzoyl chloride (8.23 g, 95.5%), which can be recrystallized from hexane. Data are: $^1H$ NMR (CDCl$_3$, 300 MHz) δ 7.75 (d, 2H), 7.29 (t, 1H), 2.34 (s, 6H); $^{13}C$ NMR (CDCl$_3$, 75 MHz) δ 168.8, 167.0, 151.4, 135.3, 122.8, 122.0, 21.2; mp=89.5-91° C.; HRMS (EI+) found 256.0130 M+, calcd 256.0139 for $C_{11}H_9O_5Cl$; Anal. Calcd for $C_{11}H_9O_5Cl$: C, 51.48; H, 3.53. Found: C, 51.60; H, 3.68.

7. Preparation of 4-chloroacetoxystyrene

A flask was charged with 4-acetoxystyrene (10 g, 61.73 mmol), methanol (30 mL), and KOH (0.125 g, 2.23 mmol), and 1 drop of water. After the mixture was stirred for 5 minutes under $N_2$, the temperature was raised to 65° C. The mixture was stirred for 1.5 h and then cooled to room temperature. Acetic acid (0.144 g, 2.44 mmol) in methanol (0.5 mL) was added slowly over 5 min. The mixture was stirred for another 5 min and then concentrated. The residue was dissolved in toluene and filtered. The filtrate was cooled to −78° C. and the 4-hydroxystyrene was precipitated, filtered and dried to give 4.5 g product (60%).

To a solution of 4-hydroxystyrene (1.22 g, 10 mmol) in ethyl ether 140 mL was added chloroacetic chloride (2.26 g, 20 mmol) and $Et_3N$ (1.62 g, 16 mmol). After it was stirred for 2 h, the mixture was washed with brine and water. The ether solution was dried over $Na_2SO_4$ and concentrated. After purification by flash column, the 4-chloroacetoxystyrene (1.8 g, 92%) was obtained. Data are: $^1$H NMR (CDCl$_3$, 300 MHz) δ 7.46 (d, 2H, J=1.8 Hz), 7.11 (d, 2H, J=8.4 Hz), 6.73 (dd, 1H, J=17.7 Hz), 5.74 (d, 1H, J=18 Hz), 5.29 (d, J=11.1 Hz), 4.31 (s, 2H). $^{13}$C NMR (CDCl$_3$, 75 MHz) δ166.0, 150.0, 136.0, 135.8, 127.4, 121.3, 114.6, 41.0.

8. Preparation of 3,5-diacetoxy-4'-chloroacetoxy stilbene

A 10 mL round bottom flask was charged with p-xylene (4 mL), Pd II catalyst (4.5 mg, 0.02 mmol), 1,3-bis-(2,6-diisopropylphenyl)imidazolinium chloride (8.6 mg, 0.02 mmol), 3,5-diacetoxybenzoyl chloride (0.7695 g, 3 mmol), 4-chloroacetoxystyrene (0.393 g, 2 mmol), and N-methyl morpholine (0.276 g, 2.4 mmol). The mixture was stirred at 120° C. for 3.5 h under nitrogen atmosphere. Then it was cooled to room temperature and EtOAc was added and filtered. The filtrate was washed with brine and dried over Na$_2$SO$_4$. Then it was filtered and purified via flash chromatography and gave the product (0.54 g, 69.4%) as white solid. Data are: $^1$H NMR (CDCl$_3$, 300 MHz) δ 7.47 (d, 2H, J=8.7 Hz), 7.14-7.10 (m, 4H), 6.99 (q, 2H, J=16.2 Hz), 6.83 (t, 1H, J=2.1 Hz), 4.29 (s, 2H), 2.29 (s, 6H); $^{13}$C NMR (CDCl$_3$, 75 MHz) δ 169.1, 165.9, 151.4, 150.1, 139.5, 135.1, 129.5, 127.9, 127.7, 121.6, 117.1, 114.7, 41.0, 21.2; HRMS (EI$^+$) found 388.0710 M$^+$, calcd 388.0714 for C20H17ClO6.

9. Preparation of 3,5-diacetoxy-4'-hydroxy stilbene

A solution of 3,5-diacetoxy-4'-chloroacetoxy stilbene (0.388 g, 1 mmol) in 50% aqueous pyridine, which was adjusted to pH 6.7 with hydrochloric acid, was stirred for 6 h at room temperature. The mixture was concentrated and diluted with EtOAc. The mixture was washed with 1 N aqueous HCl, saturated NaHCO$_3$ and water. Then the EtOAc solution was dried and concentrated. After purification by radial chromatography, the product (0.28 g, 90%) was obtained. Data are: $^1$H NMR (Aceton-d$_6$, 300 MHz) δ 8.55 (bs, 1H), 7.47 (m, 2H), 7.25-7.00 (m, 4H), 6.86 (m, 2H), 6.82 (t, 1H, J=2.1 Hz), 2.27 (s, 3H); $^{13}$C NMR (Aceton-d$_6$, 75 MHz) δ169.5, 158.7, 152.7, 141.2, 131.4, 129.5, 129.2, 124.8, 117.5, 116.6, 115.1, 21.0; HRMS (EI$^+$) found 312.0993 M$^+$, calcd 312.0998 for C$_{18}$H$_{16}$O$_6$.

The following are prepared according to Scheme 13.

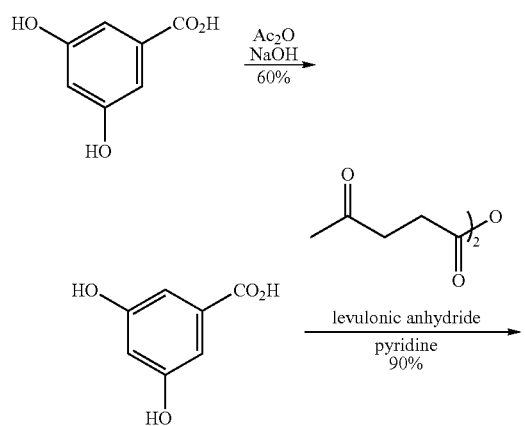

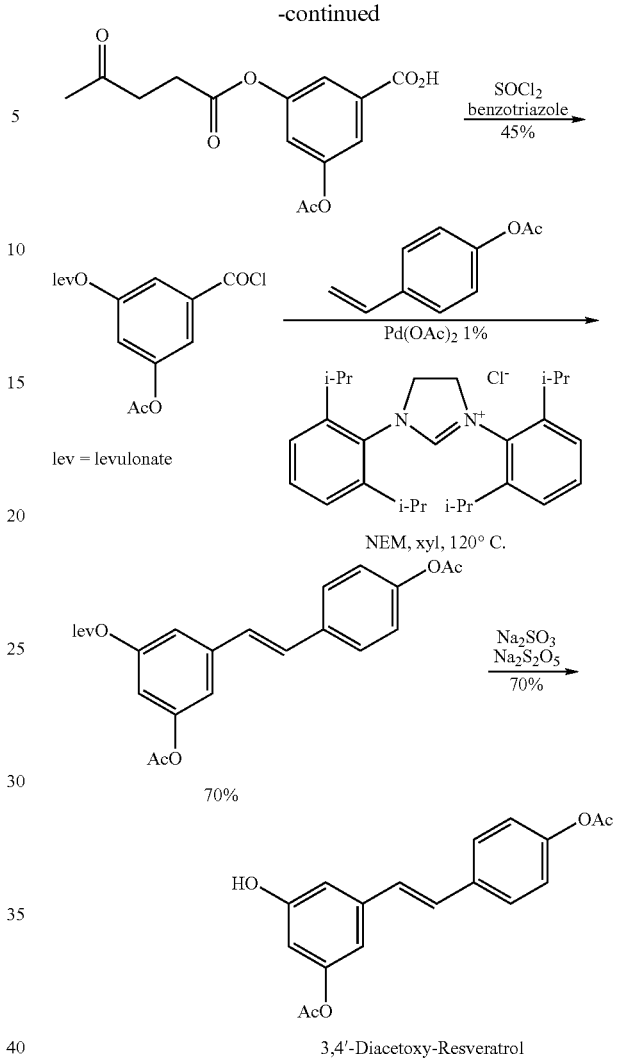

10. Preparation of 3-acetoxy-5-hydroxybenzoic acid

To 3,5-dihydroxybenzoic acid (20 g, 129 mmol) was added NaOH (15.6 g, 390 mmol) in 100 mL water. After the mixture was cooled to 0° C., Ac$_2$O (13.2 g, 129 mmol) was added. The solution was stirred for 40 min and then acidified with 10% H$_2$SO$_4$ at 0° C. The precipitate was filtered and washed with cold water. The crude product was recrystallized from water to give 3-acetoxy-5-hydroxybenzoic acid (15.2 g, 60%). Data are: $^1$H NMR (Aceton-d$_6$, 300 MHz) δ 8.96 (s, 1H), 7.40 (dd, 1H, J=1.5 Hz), 7.26 (dd, 1H, J=1.5 Hz), 6.86 (t, 1H, 2.1H), 2.27 (s, 3H); HRMS (EI$^+$) found 196.0380 M$^+$, calcd 196.0372 for C$_9$H$_8$O$_6$.

11. Preparation of 3-acetoxy-5-levulinoxybenzoic acid

To a solution of 3-acetoxy-5-hydroxybenzoic acid (2.45 g, 12.5 mmol) in CH$_2$Cl$_2$ (25 mL) was added levulinic anhydride (5.4 g, 25 mmol) and pyridine (1.22 mL, 15 mmol) at 0° C. The mixture was stirred at 0° C. for another 0.5 h and then warmed to room temperature. After 3 h, 98% formic acid was added and stirred for 1 h. The mixture was washed with 1 N HCl, saturated NaHCO$_3$ and water. Then it was dried by Na₂SO₄ and concentrated. The crude product was purified by flash column and give 3-acetoxy-5-levulinoxybenzoic acid (3.52 g, 96%). Data are: ¹H NMR (CDCl₃, 300 MHz) δ 7.72 (d, 2H, J=1.2 Hz), 7.20 (t, 1H, 1.2 Hz), 2.85 (m, 4H), 2.32 (s, 3H), 2.24 (s, 3H); ¹³C NMR (CDCl₃, 75 MHz) δ 206.6, 177.6, 171.0, 170.0, 169.0, 151.2, 131.7, 121.1, 121.1, 121.0, 38.1, 30.0, 28.3, 21.2; HRMS (EI⁺) found 294.0741 M⁺, calcd 294.0740 for C₁₄H₁₄O₇.

12. Preparation of 3-acetoxy-5-levulinoxybenzoyl chloride

A stock solution was prepared by dissolving benzotriazole (1.49 g, 12.5 mmol), thionyl chloride (0.91 mL, 12.5 mmol) in 8.0 mL DCM. Reaction was carried out by adding the stock solution intermittently into a stirred solution of 3-acetoxy-5-levulinoxybenzoic acid (2.94 g, 10 mmol) in 200 ml DCM. Before the addition was complete, benzotriazole hydrochloride started precipitating out as white solid. The mixture was stirred for another ten minutes. After filtration, the filtrate was stirred with MgSO₄.7H₂O (5 g) to destroy the excess thionyl chloride. After concentration, the residue was extracted by hot dry hexane several times and recrystallized from hexane to give 3-acetoxy-5-levulinoxybenzoyl chloride (1.4 g, 45%). Data are: ¹H NMR (CDCl₃, 300 MHz) δ 7.75 (d, 2H, J=2.1 Hz), 7.28 (t, 1H, J=2.1 Hz), 2.86 (m, 4H), 2.33 (s, 3H), 1.24 (s, 1H); ¹³C NMR (CDCl₃, 75 MHz) δ 206.3, 170.9, 168.7, 167.1, 151.42, 151.38, 135.3, 122.8, 122.1, 121.9, 38.0, 30.0, 28.3, 21.2; HRMS (EI⁺) found 312.0390 M⁺, calcd 312.0401 for C₁₄H₁₃O₆Cl.

13. Preparation of 3,4'-diacetoxy-5-levulinoxystilbene

A 25 mL round bottom flask was charged with p-xylene (6 mL), Pd II catalyst (6.9 mg, 0.03 mmol), 1,3-bis-(2,6-diisopropylphenyl)imidazolinium chloride (12.9 mg, 0.03 mmol), 3-acetoxy-5-levulinoxybenzoyl chloride (0.936 g, 3 mmol), 4-acetoxystyrene (0.583 g, 3.6 mmol), and N-methyl morpholine (0.42 g, 3.6 mmol). The mixture was stirred at 120° C. for 3.5 h under nitrogen atmosphere. Then it was cooled to room temperature and EtOAc was added and filtered. The filtrate was washed with brine and dried over Na₂SO₄. Then it was filtered and purified via flash chromatography and gave the product (0.86 g, 70%) as white solid. Data are: ¹H NMR (CDCl₃, 300 MHz) δ 7.48 (m, 2H), 7.12 (m, 6H), 6.81 (t, 1H, J=1.2 Hz), 2.85 (m, 4H), 2.31 (s, 1H), 2.30 (s, 1H), 2.23 (s, 1H); ¹³C NMR (CDCl₃, 75 MHz) δ 206.4, 171.2, 169.5, 169.1, 151.5, 150.6, 140.0, 134.7, 129.8, 127.8, 127.4, 122.1, 117.14, 117.09, 114.6, 38.1, 30.0, 28.4, 21.32, 21.29.

14. Preparation of 3,4'-diacetoxy-5-hydroxystilbene

To a solution of 3,4'-diacetoxy-5-levulinoxystilbene (0.72 g, 1.75 mmol) in THF (5 mL) was added a solution of Na₂SO₃ and Na₂S₂O₅ (0.26 g, 2.1 mmol and 0.1 g, 0.53 mmol) in water (5 mL). The reaction mixture was stirred for 9 h at room temperature under N₂. Then the mixture was poured into water and extracted with ethyl acetate three times and dried over Na₂SO₄. The solvent was removed under reduced pressure and purified by radial chromatography to give 3,4'-diacetoxy-5-hydroxystilbene (0.40 g, 73%). Data are: ¹H NMR (Aceton-d₆, 300 MHz) δ 8.66 (bs, 1H), 7.63 (m, 2H), 7.25 (m, 4H), 6.94 (t, 1H, J=1.8 Hz), 6.86 (t, 1H, J=1.8 Hz), 6.54 (t, 1H, J=2.1 Hz), 2.26 (s, 3H), 2.25 (s, 3H); ¹³C NMR (Aceton-d₆, 75 MHz) δ 169.7, 169.6, 159.2, 153.2, 151.6, 140.4, 135.6, 129.4, 128.8, 128.3, 122.9, 111.85, 111.79, 109.4, 21.07, 21.02; HRMS (EI⁺) found 312.0996 M⁺, calcd 312.0998 for C₁₈H₁₆O₅.

The following are prepared according to Scheme 14.

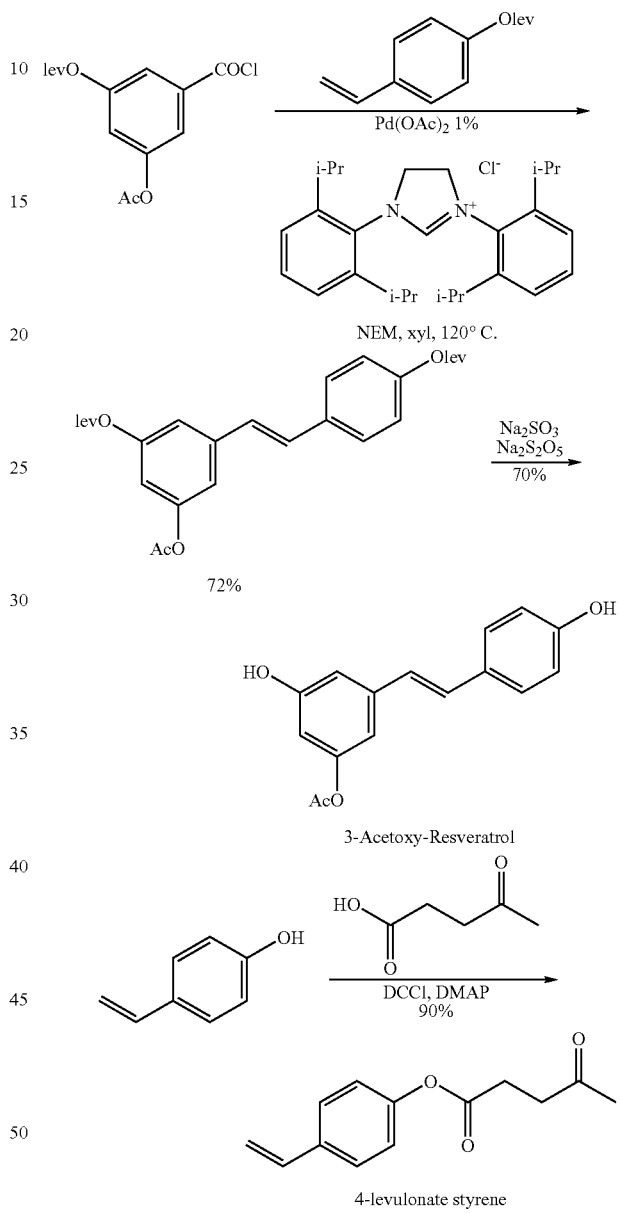

Scheme 14.

3-Acetoxy-Resveratrol 4-levulonate styrene

15. Preparation of 4-levulinoxystyrene

A flame dried flask was charged with dioxane (120 mL), 4-hydroxystyrene (3.66 g, 30 mmol), levulinic acid (6.97 g, 60 mmol), DCCI (12.39 g, 60 mmol), DMAP (300 mg). The mixture was stirred under N₂ for 3.5 h. Then the mixture was washed with water, dried over Na₂SO₄, concentrated under reduced pressure and purified by flash column to give 4-levulinoxystyrene (5.9 g, 90%). Data are: ¹H NMR (CDCl₃, 300 MHz) δ 7.39 (m, 2H), 7.04 (m, 2H), 6.68 (dd, 1H), 5.69 (d, 1H, J=17.7 Hz), 5.69 (d, 1H, J=10.8 Hz), 2.82 (m, 4H), 2.20 (s, 3H); ¹³C NMR (CDCl₃, 75 MHz) δ 206.5, 171.5, 150.4, 136.0, 135.5, 127.3, 121.7, 114.1, 38.0, 30.0, 28.3; HRMS (EI⁺) found 218.0955 M⁺, calcd 218.0943 for $C_{13}H_{14}O_3$.

16. Preparation of 3-acetoxy-4',5-dilevulinoxystilbene

A 25 mL round bottom flask was charged with p-xylene (6 mL), Pd II catalyst (6.9 mg, 0.03 mmol), 1,3-bis-(2,6-diisopropylphenyl)imidazolinium chloride (12.9 mg, 0.03 mmol), 3-acetoxy-5-levulinoxybenzoyl chloride (0.936 g, 3 mmol), 4-levulinoxystyrene (0.786 g, 3.6 mmol), and N-methyl morpholine (0.42 g, 3.6 mmol). The mixture was stirred at 120° C. for 3.5 h under nitrogen atmosphere. Then it was cooled to room temperature and EtOAc was added and filtered. The filtrate was washed with brine and dried over $Na_2SO_4$. Then it was filtered and purified via flash chromatography and gave the product (1.0 g, 72%) as white solid. Data are: ¹H NMR (CDCl₃, 300 MHz) δ 7.47 (m, 2H), 7.11-6.92 (m, 6H), 6.81 (t, 2.1 Hz), 2.89-2.80 (m, 8H), 2.29 (s, 3H), 2.224 (s, 3H), 2.221 (s, 3H); ¹³C NMR (CDCl₃, 75 MHz) δ 206.6, 206.5, 171.5, 171.2, 169.1, 151.4, 151.5, 150.6, 139.7, 134.6, 129.8, 127.8, 127.3, 122.0, 117.10, 117.05, 114.5, 38.07, 38.02, 30.01, 30.00, 28.32, 28.30, 21.3; HRMS (EI⁺) found 466.1636 M⁺, calcd 466.1628 for $C_{26}H_{26}O_8$.

17. Preparation of 3-acetoxy-4',5-dihydroxystilbene

A solution of 3-acetoxy-4',5-dilevulinoxystilbene (0.47 g, 1.0 mmol) in THF (3 mL) was added a solution of $Na_2SO_3$ and $Na_2S_2O_5$ (0.30 g, 2.4 mmol and 0.11 g, 0.6 mmol) in water (3 mL). The reaction mixture was stirred for 7 h at room temperature under $N_2$. Then the mixture was poured into water and extracted with ethyl acetate three times and dried over $Na_2SO_4$. The solvent was removed under reduced pressure and purified by chromatography to give 3-acetoxy-4',5-dihydroxystilbene (0.19 g, 70%). Data are: ¹H NMR (Aceton-d₆, 300 MHz) δ 8.56 (bs, 1H), 7.45 (m, 2H), 7.04 (dd, 2H, J=48.9 Hz), 6.90-6.80 (m, 4H), 6.50 (t, 1H, 2.1 Hz), 2.24 (s, 1H); ¹³C NMR (Aceton-d₆, 75 MHz) δ 169.6, 159.2, 158.5, 153.3, 141.1, 129.8, 130.3, 129.0, 116.5, 111.5, 111.4, 108.8, 21.1; HRMS (EI⁺) found 270.0896 M⁺, calcd 270.0892 for $C_{16}H_{16}O_4$.

The following are prepared according to Scheme 15.

Scheme 15.

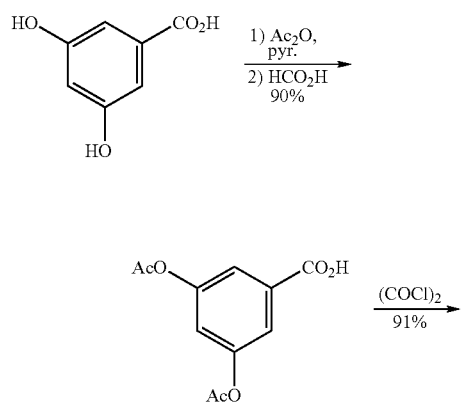

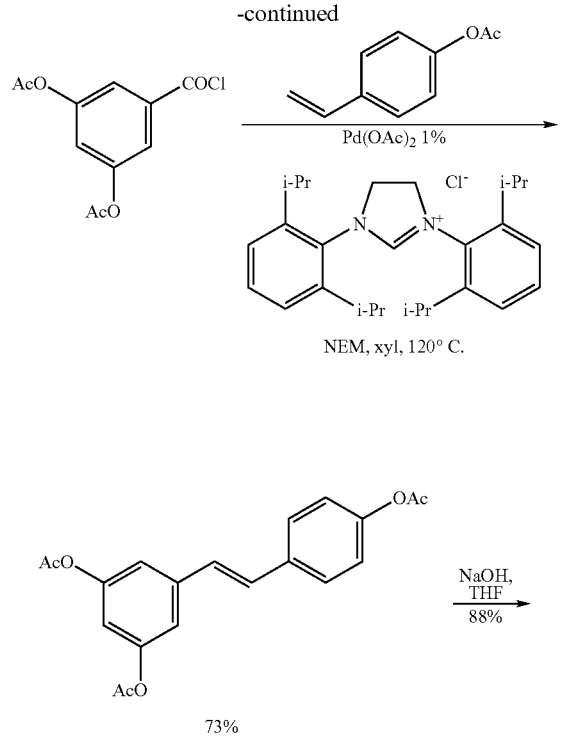

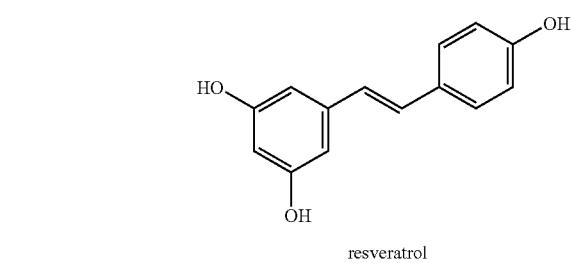

resveratrol

18. Preparation of 3,5,4'-triacetoxy stilbene

A 100 mL round bottom flask was charged with p-xylene (56 mL), Pd(OAc)₂ (62.86 mg, 0.28 mmol), 1,3-bis-(2,6-diisopropylphenyl)imidazolinium chloride (119.53 mg, 0.28 mmol), 3,5-diacetoxybenzoyl chloride (7.19 g, 28 mmol), 4-acetoxystyrene (5.35 mL, 33.6 mmol), and N-methyl morpholine (4.2 mL, 33.6 mmol). The mixture was stirred at 120° C. for 3.5 h at nitrogen atmosphere. Then it was cooled to room temperature and EtOAc was added and filtered. The filtrate was washed with brine and dried over $Na_2SO_4$. Then it was filtered and purified via flash chromatography (15% EtOAc/hexane, 25% EtOAc/Hexene, then 35% EtOAc/hexane) and gave resveratrol triacetate (6.95 g, 70.1%) as white solid. Data are: ¹H NMR (CDCl₃, 300 MHz) δ 7.50 (d, 2H), 7.12-6.94 (m, 6H), 6.82 (t, 1H), 2.31 (s, 9H); ¹³C NMR (CDCl₃, 75 MHz) δ 169.6, 169.2, 151.5, 150.6, 139.7, 134.7, 129.9, 127.9, 127.4, 122.1, 117.1, 114.6, 21.4; mp=116-118° C.; HRMS (EI⁺) found 354.1118 M⁺, calcd 354.1103 for $C_{20}H_{18}O_6$; Anal. Calcd for $C_{20}H_{18}O_6$: C, 67.79; H, 5.12. Found: C, 67.93; H, 5.26.

The following are prepared according to Scheme 16.

Scheme 16
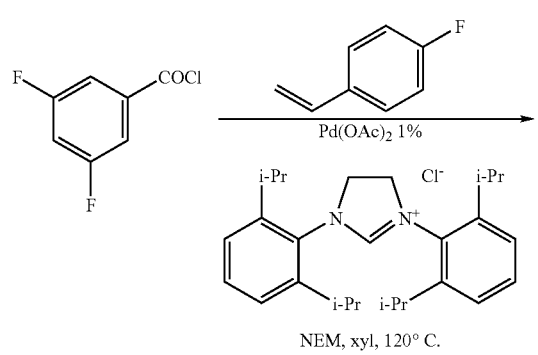
trifluoro
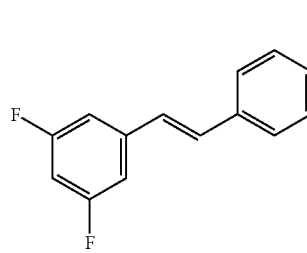
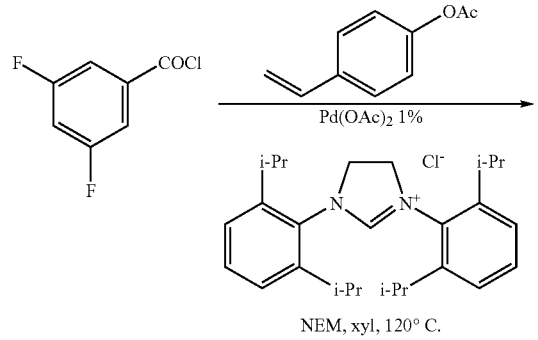
3,5-difluoro
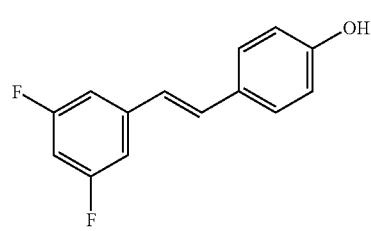
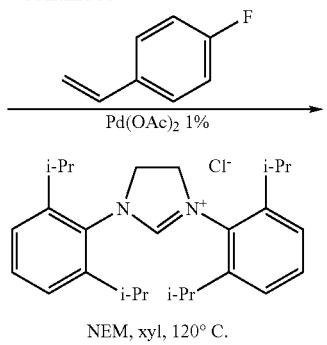
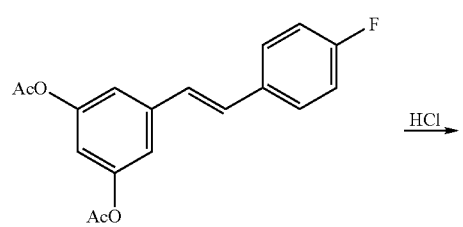
HCl →
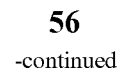
4'-fluoro
1) BnOH, NaH
2) Pd(OAc)₂ 3%
   (o-tol)₃P 6%
   Et₃N, DMF
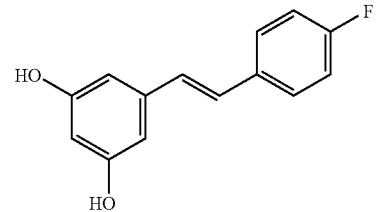
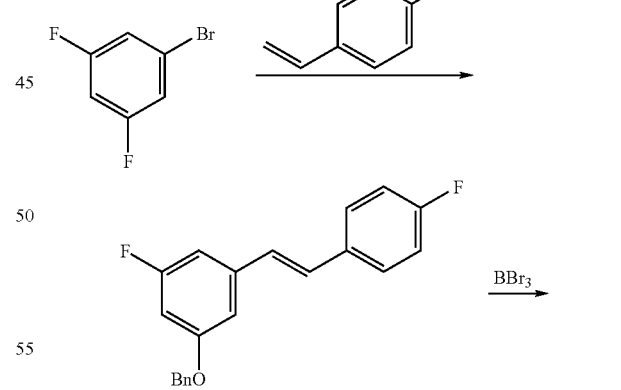
3,4'-difluoro
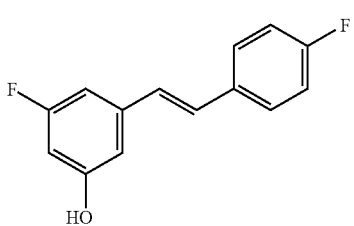
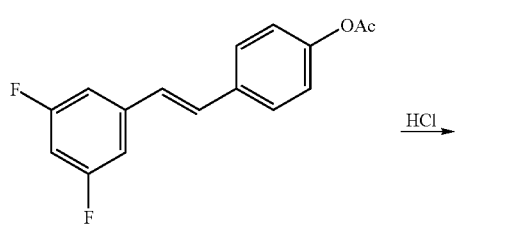

-continued

1) BnOH, NaH
2) Pd(OAc)₂ 3%
(o-tol)₃P 6%
Et₃N, DMF

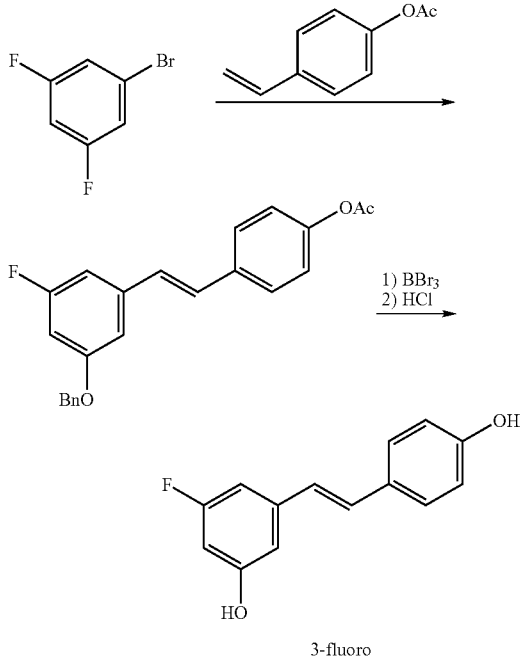

3-fluoro

19. Preparation of 3,5,4'-trifluorostilbene

A 25 mL round bottom flask was charged with p-xylene (10 mL), Pd(OAc)₂ (11.3 mg, 0.05 mmol), 1,3-bis-(2,6-diisopropylphenyl)imidazolinium chloride (21.4 mg, 0.05 mmol), 3,5-difluorobenzoyl chloride (0.89 g, 5 mmol), 4-fluorostyrene (0.74 g, 6 mmol), and N-methyl morpholine (0.69 g, 6 mmol). The mixture was stirred at 120° C. for 3.5 h under nitrogen atmosphere. Then it was cooled to room temperature and EtOAc was added and filtered. The filtrate was washed with brine and dried over Na₂SO₄. Then it was filtered and purified via flash chromatography and gave the product (0.94 g, 80%) as white solid. Data are: $^1$H NMR (CDCl₃, 300 MHz) δ 7.47 (m, 2H), 7.08-6.88 (m, 6H), 6.70 (tt, 1H); $^{13}$C NMR (CDCl₃, 75 MHz) δ 163.52 (dd), 162.98 (d), 140.82 (t), 132.77, 130.26, 128.58 (d), 126.53, 116.03 (d), 109.20 (q), 102.98 (t); $^{19}$F NMR (CDCl₃, 282 MHz) δ −31207.2 (q, 2F), −31965.6 (q, 1F); HRMS (EI⁺) found 234.0645 M⁺, calcd 234.0656 for $C_{14}H_9F_3$.

20. Preparation of 4'-acetoxy-3,5-difluorostilbene

A 25 mL round bottom flask was charged with p-xylene (10 mL), Pd(OAc)₂ (11.3 mg, 0.05 mmol), 1,3-bis-(2,6-diisopropylphenyl)imidazolinium chloride (21.4 mg, 0.05 mmol), 3,5-difluorobenzoyl chloride (0.89 g, 5 mmol), 4-acetoxystyrene (0.97 g, 6 mmol), and N-methyl morpholine (0.69 g, 6 mmol). The mixture was stirred at 120° C. for 3.5 h under nitrogen atmosphere. Then it was cooled to room temperature and EtOAc was added and filtered. The filtrate was washed with brine and dried over Na₂SO₄. Then it was filtered and purified via flash chromatography and gave the product (1.02 g, 74%) as white solid. Data are: $^1$H NMR (CDCl₃, 300 MHz) δ 7.51 (d, J=8.4 Hz, 2H), 7.12-6.97 (m, 6H), 6.70 (t, 1H), 2.31 (s, 3H).

21. Preparation of 3,5-difluoro-4'-hydroxystilbene

To a solution of 3,5-difluoro-4'-acetoxystilbene (0.69 g, 2.5 mmol) in MeOH (10 ml) was added 5 mL 4M HCl in 1,4-dioxane. The mixture was stirred for 20 minutes at ambient temperature. After purification by flash column, 3,5-difluoro-4'-hydroxystilbene (0.51 g, 88%) was obtained. Data are: $^1$H NMR (CDCl₃, 300 MHz) δ 7.40 (m, 2H), 7.05-6.83 (m, 6H), 6.67 (tt, 1H), 4.88 (s, 1H); $^{13}$C NMR (CDCl₃, 75 MHz) δ 164.49 (d), 162.47, 156.01, 141.29, 130.90, 128.53, 124.74, 115.96, 109.03 (t), 102.53 (t); $^{19}$F NMR (CDCl₃, 282 MHz) δ −31278.95 (t, J=1720.2 Hz); HRMS (EI⁺) found 232.0715 M⁺, calcd 232.0700 for $C_{14}H_{10}F_2O$.

22. Preparation of 3,5-diacetoxy-4'-fluorostilbene

A 25 mL round bottom flask was charged with p-xylene (10 mL), Pd(OAc)₂ (11.3 mg, 0.05 mmol), 1,3-bis-(2,6-diisopropylphenyl)imidazolinium chloride (21.4 mg, 0.05 mmol), 3,5-diacetoxybenzoyl chloride (1.28 g, 5 mmol), 4-fluorostyrene (0.73 g, 6 mmol), and N-methyl morpholine (0.69 g, 6 mmol). The mixture was stirred at 120° C. for 3.5 h under nitrogen atmosphere. Then it was cooled to room temperature and EtOAc was added and filtered. The filtrate was washed with brine and dried over Na₂SO₄. Then it was filtered and purified via flash chromatography and gave the product (1.15 g, 73%) as white solid. Data are: $^1$H NMR (CDCl₃, 300 MHz) δ 7.45 (dd, 2H), 7.11-6.91 (m, 6H), 6.82 (t, J=1.95 Hz, 1H).

23. Preparation of 4'-fluoro-3,5-dihydroxystilbene

To a solution of 3,5-diacetoxy-4'-fluorostilbene (0.79 g, 2.5 mmol) in MeOH (10 ml), 10 mL 4M HCl in 1,4-dioxane was added. The mixture was stirred for 30 minutes at ambient temperature. After purification by flash column, 3,5-difluoro-4'-hydroxy-stilbene (0.49 g, 85%) was obtained. Data are: $^1$H NMR (Aceton-d₆, 300 MHz) δ 8.25 (s, 1H), 7.61 (m, 2H), 7.16-7.00 (m, 4H), 6.58 (d, J=2.4 Hz), 6.31 (t, J=2.3 Hz); $^{13}$C NMR (Aceton-d₆, 75 MHz) δ; $^{19}$F NMR (Aceton-d₆, 282 MHz) δ −32881.41 (m); HRMS (EI⁺) found 230.0737 M⁺, calcd 230.0743 for $C_{14}H_{11}FO_2$.

24. Preparation of 5-benzyloxy-3-fluorophenyl bromide

To a stirred solution of benzyl alcohol (3.86 g, 20 mmol) in DMA (30 ml), NaH (60% dispersion in oil, 0.80 g, 20 mmol) was drop wisely added. After one hour, 1-bromo-3,5-difluorobenzen (3.86 g, 20 mmol) was added at such a rate to maintain the temperature no more than 40° C. The mixture was stirred at ambient temperature overnight. The reaction was quenched by water and extracted with EtOAc. It was purified via flash chromatography and gave the product (4.17 g, 74%) as colorless oil. Data are: $^1$H NMR (CDCl₃, 300 MHz) δ 7.41-7.43 (m, 5H), 6.94 (m, 1H), 6.86 (dt, 1H), 6.63 (dt, 1H), 5.02 (s, 2H); $^{13}$C NMR (CDCl₃, 75 MHz) δ 165.20, 161.89, 160.72, 160.56, 136.01, 128.94, 128.57, 127.77, 127.73, 122.99, 122.83, 114.58, 114.53, 112.18, 111.84, 102.29, 101.96, 70.76; $^{19}$F NMR (CDCl₃, 282 MHz) δ −31129.40 (t, J=2583.12 Hz).

25. Preparation of 5-benzyloxy-3,4'-difluorostilbene

A mixture of 5-benzyloxy-3-fluorophenyl Bromide (2.81 g, 10 mmol), Pd(OAc)₂ (0.067 g, 0.3 mmol), tri-o-tolylphosphine (0.18 g, 0.6 mmol), 4-fluorostyrene (1.53 g, 12.5 mmol), and Et₃N (1.26 g, 12.5 mmol) in 20 ml dry DMF was stirred at 100° C. for 24 hours under N$_2$. The dark mixture was distributed between EtOAc and 1N HCl. The organic layer was separated and washed with water and brine, dried over Na$_2$SO$_4$, filtered, and evaporated. After flash column, the desired product (2.93 g, 91%) was obtained. Data are: $^1$H NMR (CDCl$_3$, 300 MHz) δ 7.49-7.34 (m, 7H), 7.08-6.81 (m, 6H), 6.60 (dt, 1H), 5.08 (s, 2H); $^{19}$F NMR (CDCl$_3$, 282 MHz) δ −31666.54 (t), −32136.54 (t). HRMS (EI$^+$) found 322.1169 M$^+$, calcd 322.1169 for C$_{21}$H$_{16}$F$_2$O.

26. Preparation of 3,4'-difluoro-5-hydroxystilbene

A 1 M solution of BBr$_3$ (9 ml, 9 mmol) in CH$_2$Cl$_2$ was added to a well-stirred solution of 5-benzyloxy-3,4'-difluorostilbene (0.97 g, 3 mmol) in dry CH$_2$Cl$_2$ (120 ml) at −78° C. The mixture was warmed to −20° C. and stirred for 10 minutes. Then MeOH was added at −78° C. The mixture was washed with saturated NaHCO$_3$, and water. Flash chromatography gave the 3,4'-difluoro-5-hydroxystilbene (0.60 g, 86%) as white solid. Data are: $^1$H NMR (CDCl$_3$, 300 MHz) δ 7.46 (m, 2H), 7.08-6.73 (m, 6H), 6.48 (dt, 1H), 4.85 (s, 1H); $^{13}$C NMR (CDCl$_3$, 75 MHz) δ 165.05 (d), 161.78 (d), 157.06 (d), 140.43 (d), 133.06 (d), 129.40 (s), 128.45 (d), 127.25 (t), 115.95 (d), 109.42 (d), 105.91 (d), 102.60 (d); $^{19}$F NMR (CDCl$_3$, 282 MHz) δ −31703.17 (t), −32099.92 (t); HRMS (EI$^+$) found 232.0714 M$^+$, calcd 232.0700 for C$_{14}$H$_{10}$F$_2$O.

27. Preparation of 4'-acetoxy-5-benzyloxy-3-fluorostilbene

A mixture of 5-benzyloxy-3-fluorophenyl bromide (2.81 g, 10 mmol), Pd(OAc)$_2$ (0.067 g, 0.3 mmol), tri-o-tolylphosphine (0.18 g, 0.6 mmol), 4-acetoxystyrene (2.03 g, 12.5 mmol), and Et$_3$N (1.26 g, 12.5 mmol) in 20 mL dry DMF was stirred at 100° C. for 24 hours under N$_2$. The dark mixture was distributed between EtOAc and 1N HCl. The organic layer was separated and washed with water and brine, dried over Na$_2$SO$_4$, filtered, and evaporated. After flash column, the desired product (3.19 g, 88%) was obtained. Data are: $^1$H NMR (CDCl$_3$, 300 MHz) δ 7.51-7.34 (m, 7H), 7.11-6.82 (m, 6H), 6.60 (dt, 1H); $^{13}$C NMR (CDCl$_3$, 75 MHz) δ 169.66, 165.64, 162.40, 160.47, 150.58, 140.07 (d), 136.59, 134.76, 129.41, 128.91, 128.41, 128.04 (d), 127.79 (d), 122.11, 109.36 (d), 105.86 (d), 101.91 (d), 70.57, 21.37; $^{19}$F NMR (CDCl$_3$, 282 MHz) δ −31675.70 (t); HRMS (EI$^+$) found 362.1302 M$^+$, calcd 362.1318 for C$_{23}$H$_{19}$FO$_3$.

28. Preparation of 3-fluoro-5,4'-dihydroxystilbene

A 1 M solution of BBr$_3$ (9 ml, 9 mmol) in CH$_2$Cl$_2$ was added to a well-stirred solution of 5-benzyloxy-3-fluoro-4'-acetoxystilbene (1.09 g, 3 mmol) in dry CH$_2$Cl$_2$ (120 mL) at −78° C. The mixture was warmed to −20° C. and stirred for 10 minutes. Then MeOH was added at −78° C. The mixture was washed with saturated NaHCO$_3$, and water, dried over Na$_2$SO$_4$, filtered and evaporated. The 4'-acetoxy-3-fluoro-5-hydroxystilbene (0.50 g, 61%) was obtained as white solid. To a solution of the crude 4'-acetoxy-3-fluoro-5-hydroxystilbene (0.50 g, 1.8 mmol) in MeOH (7.5 ml) was added 3.7 ml 4M HCl in 1,4-dioxane. The mixture was stirred for 20 minutes at ambient temperature. After purification by flash column, 3-fluoro-5,4'-dihydroxystilbene (0.33 g, 78%) was obtained. Data are: $^1$H NMR (Aceton-d$_6$, 300 MHz) δ 8.624 (s, 2H), 7.46 (m, 2H), 7.06 (q, 2H), 6.84 (m, 4H), 6.66 (dt, 1H); $^{13}$C NMR (Aceton-d$_6$, 75 MHz) δ 164.90 (d), 159.96 (d), 158.57, 142.02 (d), 130.84, 129.63, 129.10, 125.55 (d), 116.53, 110.28 (d), 104.44 (d), 102.00 (d); $^{19}$F NMR (Aceton-d$_6$, 282 MHz) δ −32429.72 (t); HRMS (EI$^+$) found 230.0738 M$^+$, calcd 230.0743 for C$_{14}$H$_{11}$FO$_2$.

The invention claimed is:

1. A process for preparing a compound of Formula I

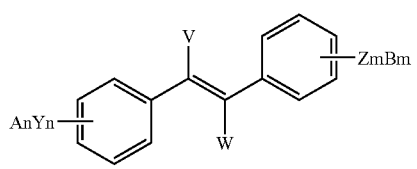

wherein each Y and each Z when present is independently selected from: —O, —O(C=O), —(C=O)—O, —O—(C=O)—O, —O—(C=O)—NH, —O—(C=O)—NR, —NH—(C=O)—O, —NR—(C=O)—O, —NH—(C=O), —NR—(C=O), —(C=O)—NH, —(C=O)—NR, —NH, —NR, N-containing heterocylic ring, —S, and halogen;

each n and each m is independently the value of: 0, 1, 2, 3, 4, or 5;

each A and each B when present is independently selected from: H and R, wherein when any Y or Z is —O, then A and B may also be selected from R, H, and P;

V and W are H;

each R when present is independently selected from: alkyl, aryl, and aralkyl;

each P when present is an alcohol protecting group;

and pharmaceutically and cosmetically acceptable salts thereof and diastereoisomers of the foregoing;

comprising the step of coupling a benzoyl halide compound of Formula IC

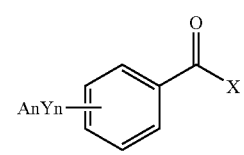

wherein X is halogen, with a 4-substituted styrene compound of Formula IE

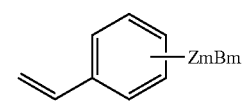

with a transition metal catalyst, N-heterocyclic carbene-type ligand and a first base.

2. The process according to claim 1, wherein each R when present is independently selected from: alkyl with at least two carbon atoms, aryl, and aralkyl; and diastereoisomers of the foregoing.

3. The process according to claim 1, wherein each R when present is independently selected from: alkyl with at least two carbon atoms, aryl, and aralkyl; and diastereoisomers of the foregoing.

4. The process according to claim 1, wherein X is Cl.

5. The process according to claim 1, wherein said first base is a non-coordinating amine base selected from the group consisting of: N,N-dimethylbenzylamine, N-methylmorpholine, and dimethylaminopyridine.

6. The process according to claim 1, wherein said N-heterocyclic carbene-type ligand is selected from imidazolium, 1,3-disubstituted imidazolium, and 1,3-disubstituted-4,5-dihydroimidazolium carbene-type ligands.

7. The process according to claim 1, wherein said N-heterocyclic carbene-type ligand is selected from N,N'-bis-(2,6-diisopropylphenyl)imidazolium chloride, N,N'-bis-(dimesityl)imidazolium chloride, and N,N'-bis-adamantylimidazolium chloride.

8. The process according to claim 1, comprising the step of irradiating the compound of Formula I with ultraviolet light.

9. The process according to claim 1, wherein the transition metal catalyst is a Pd(II) catalyst selected from Pd(OAc)$_2$, PdBr$_2$, and PdCl$_2$.

10. The method according to claim 1, wherein the compound of Formula I is in the trans configuration.

11. The compound according to claim 1, wherein the compound of Formula I is in the cis configuration.

12. The process according to claim 1, wherein the compound prepared is

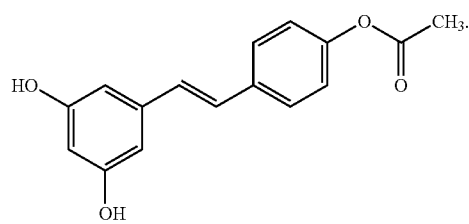 [SMILES: CC(=O)Oc1ccc(/C=C/c2cc(O)cc(O)c2)cc1]

13. A process for preparing a compound of Formula 1A3:

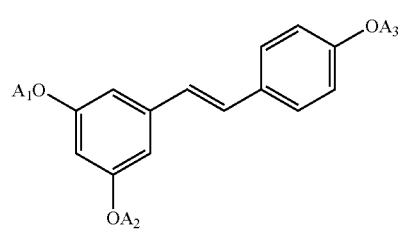

wherein $A_1$ is selected from: $P_1$ and $(CO)R_1$;
$A_2$ is selected from: $P_2$ and $(CO)R_2$;
$A_3$ is selected from: $P_3$ and $(CO)R_3$;
wherein $P_1$ when present is a first alcohol protecting group, $P_2$ when present is a second alcohol protecting group, $P_3$ when present is a third alcohol protecting group;
$R_1$, $R_2$, and $R_3$ when present are each independently selected from: alkyl, aryl, and aralkyl; and diastereoisomers of the foregoing,
and pharmaceutically and cosmetically acceptable salts thereof comprising the step of coupling a benzoyl halide compound of Formula 1A4

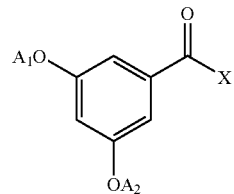

wherein X is halogen, with a 4-substituted styrene compound of Formula 1A5

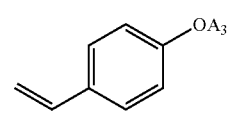

with a transition metal catalyst, N-heterocyclic carbene-type ligand and a first base.

14. The process according to claim 13, wherein the compound is of Formula 3

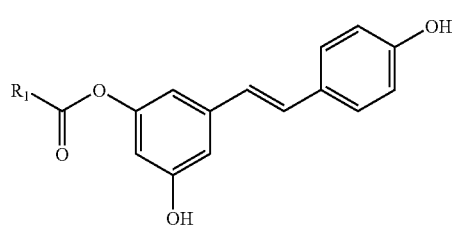

wherein $R_1$ is selected from: alkyl, aryl, and aralkyl; and pharmaceutically and cosmetically acceptable salts thereof and diastereoisomers of the foregoing, comprising:

(a) esterifying a first alcohol of resorcylic acid with an acylating agent;

(b) reacting a second alcohol of resorcylic acid with a first alcohol protecting agent;

wherein the sequence of steps (a) and (b) are interchangeable, to give the mono-ester, mono-protected alcohol of Formula 3B

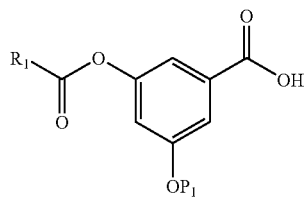

wherein $P_1$ is a first alcohol protecting group;

(c) halogenating the compound of Formula 3B using a halogenating agent to give the acid halide of Formula 3D

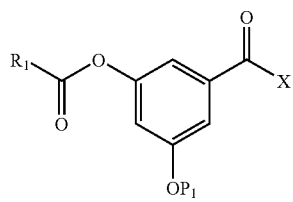

3D wherein X is halogen;

(d) coupling the compound of Formula 3E with a compound of Formula 3D

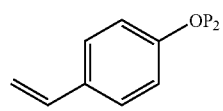

3E where $P_2$ is a second alcohol protecting group, with a transition metal catalyst, a N-heterocyclic carbene-type ligand, and a first base to yield a compound of Formula 3F;

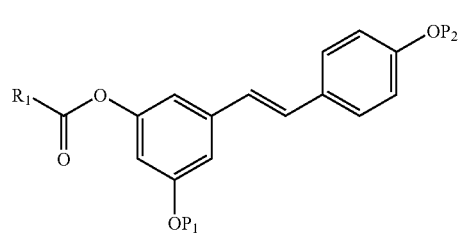

3F (e) deprotecting the first and second alcohol protecting groups from the compound of Formula 3F to give the compound of Formula 3.

15. The process according to claim 14, wherein $R_1$ is selected from alkyl with at least two carbon atoms, aryl, and aralkyl.

16. The process according to claim 13, wherein the compound is of Formula 4

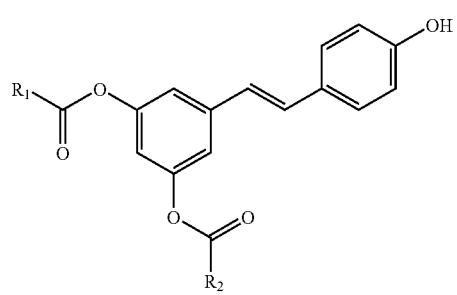

4 wherein $R_1$ and $R_2$ are independently selected from: alkyl, aryl, and aralkyl, and pharmaceutically and cosmetically acceptable salts thereof and diastereoisomers of the foregoing, comprising:

(a) esterifying resorcylic acid with an acylating agent to give the 3,5-diester of resorcylic acid of Formula 4A;

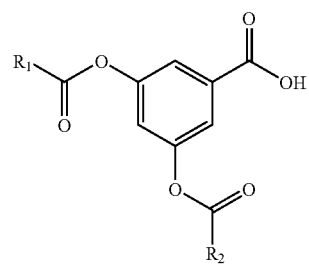

4A (b) halogenating the compound of Formula 4a using a halogenating agent to give the acid halide of Formula 4C

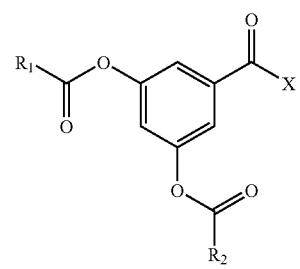

4C wherein X is halogen;

(c) coupling the compound of Formula 4C with a compound of Formula 4D

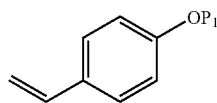

4D wherein $P_1$ is a first alcohol protecting group, with a transition metal catalyst, a N-heterocyclic carbene-type ligand, and a first base to yield a compound of Formula 4E;

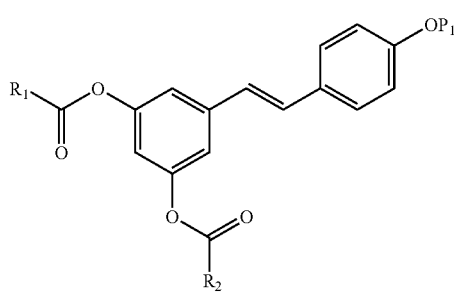

4E (d) deprotecting the first alcohol protecting group from the compound of Formula 4E to give the compound of Formula 4.

17. The process according to claim 16, wherein $R_1$ and $R_2$ are independently selected from alkyl with at least two carbon atoms, aryl, and aralkyl, and pharmaceutically and cosmetically acceptable salts thereof and diastereoisomers of the foregoing.

18. The process according to claim 13, wherein the compound is of Formula 5

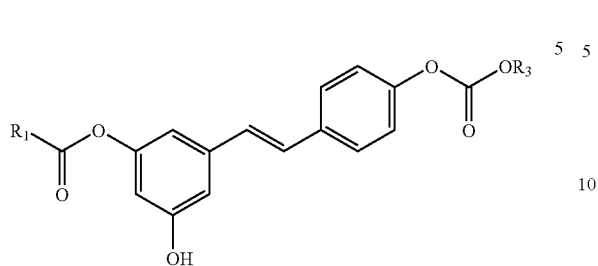
5 wherein $R_1$ and $R_3$ are independently selected from alkyl, aryl, and aralkyl, and pharmaceutically and cosmetically acceptable salts thereof and diastereoisomers of the foregoing, comprising:
 (a) esterifying a first alcohol of resorcylic acid with an acylating agent;
 (b) reacting a second alcohol of resorcylic acid with a first alcohol protecting agent,
wherein the sequence of steps (a) and (b) are interchangeable to give the mono-ester, mono-protected alcohol of Formula 5B

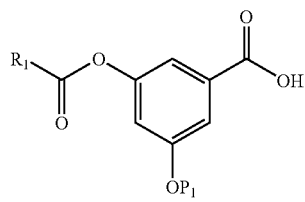
5B wherein $P_1$ is a first alcohol protecting group;
 (c) halogenating the compound of Formula 5B using a halogenating agent to give the acid halide of Formula 5D

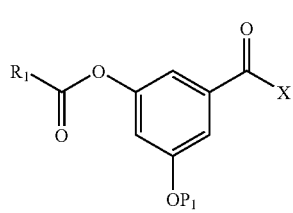
5D wherein X is halogen;
 (d) coupling the compound of Formula 5D with a compound of Formula 5E

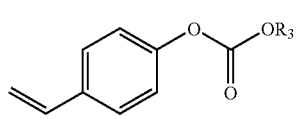
5E with a transition metal catalyst, a N-heterocyclic carbene-type ligand, and a first base to yield a compound of Formula 5F;

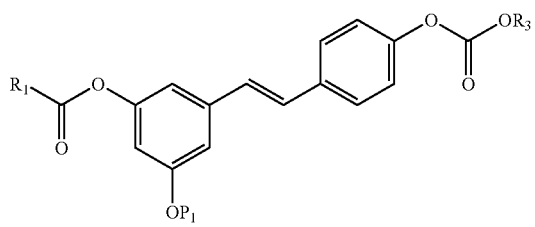
5F (e) deprotecting the first and second protecting groups from the compound of Formula 5F to give the compound of Formula 5.

19. The process according to claim 18, wherein $R_1$ and $R_3$ are independently selected from alkyl with at least two carbon atoms, aryl, and aralkyl, and pharmaceutically and cosmetically acceptable salts thereof and diastereoisomers of the foregoing.

20. The process according to claim 13, wherein the compound is of Formula 6

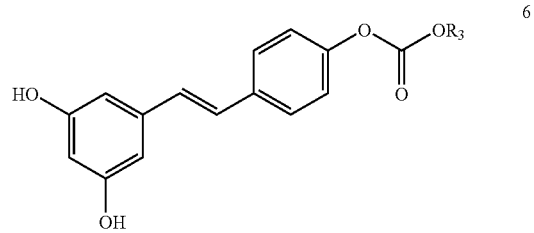
6 where $R_3$ is selected from alkyl, aryl, and aralkyl, and diastereoisomers of the foregoing, comprising:
 (a) esterifying 4-hydroxy styrene with an acylating agent to give a 4-ester styrene of Formula 6D;

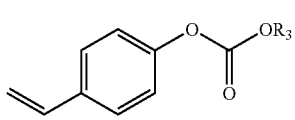
6D (b) reacting resorcylic acid with an alcohol protecting agent to give a compound of Formula 6B

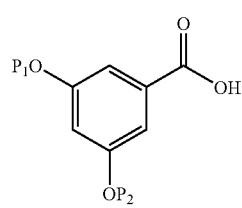
6B wherein $P_1$ is a first alcohol protecting group and $P_2$ is a second alcohol protecting group;
 (c) halogenating the compound of Formula 6B using a halogenating agent to give an acid halide of Formula 6C

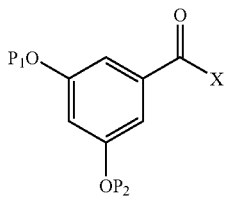

6C wherein X is halogen;
(d) coupling the compound of Formula 6D with a compound of Formula 6C with a transition metal catalyst, a N-heterocyclic carbene-type ligand, and a first base to yield a compound of Formula 6E;

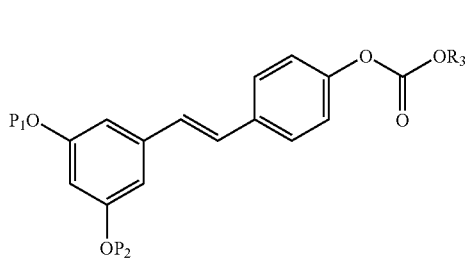

6E (e) deprotecting the first alcohol protecting group from the compound of Formula 6E to give the compound of Formula 6.

21. The process according to claim 20, wherein $R_3$ is selected from alkyl with at least two carbon atoms, aryl, and aralkyl, and pharmaceutically and cosmetically acceptable salts thereof and diastereoisomers of the foregoing.

22. The process according to claim 20, wherein the compound prepared is

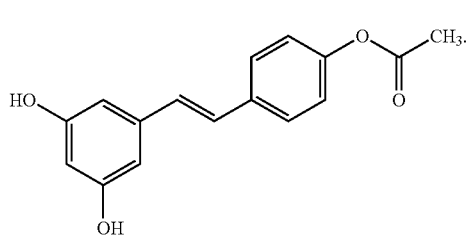 [SMILES: CC(=O)Oc1ccc(/C=C/c2cc(O)cc(O)c2)cc1]

23. The process according to claim 13, wherein the compound is of Formula 7

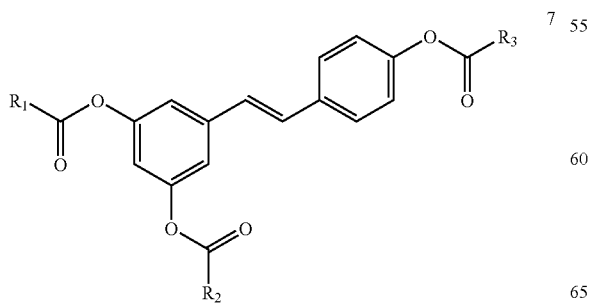

7 wherein $R_1$, $R_2$, and $R_3$ are independently selected from alkyl, aryl, and aralkyl, and pharmaceutically and cosmetically acceptable salts thereof and diastereoisomers of the foregoing, comprising:

(a) esterifying resorcylic acid with an acylating agent to give a 3,5-diester of resorcylic acid of Formula 7A;

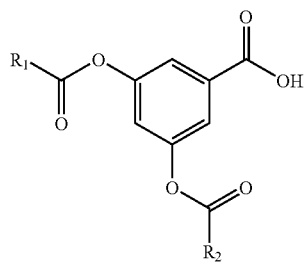

7A (b) halogenating the compound of Formula 7A using a halogenating agent to give an acid halide of Formula 7C

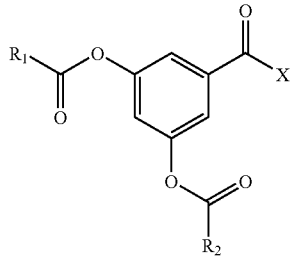

7C wherein X is halogen;
(c) coupling the compound of Formula 7C with a compound of Formula 7D

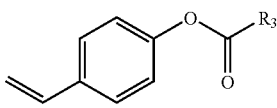

7D with a transition metal catalyst, a N-heterocyclic carbene-type ligand, and a first base.

24. The process according to claim 23, wherein $R_1$, $R_2$ and $R_3$ are independently selected from alkyl with at least two carbon atoms, aryl, and aralkyl, and pharmaceutically and cosmetically acceptable salts thereof and diastereoisomers of the foregoing.-

25. The process according to claim 13, wherein the compound is of Formula 7

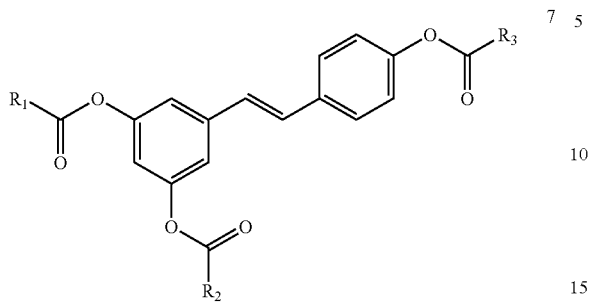

7 wherein $R_1$, $R_2$, and $R_3$ are independently selected from alkyl, aryl, and aralkyl, and pharmaceutically and cosmetically acceptable salts thereof and diastereoisomers of the foregoing, comprising:
(a) esterifying resorcylic acid with an acylating agent to give a 3,5-diester of resorcylic acid of Formula 7A;

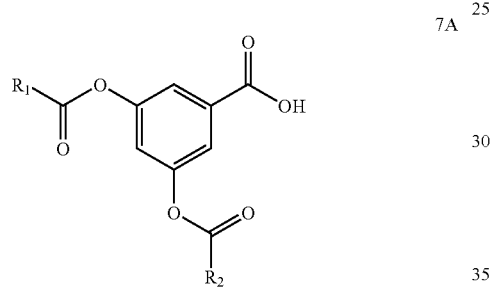

7A (b) halogenating the compound of Formula 7A using a halogenating agent to give an acid halide of Formula 7C

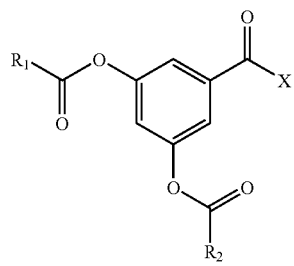

7C wherein X is halogen;

(c) coupling the compound of Formula 7C with a compound of Formula 7D

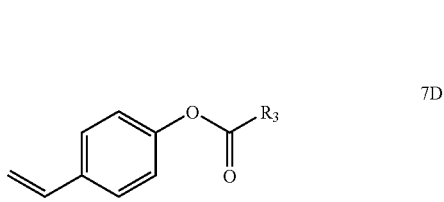

7D with a transition metal catalyst, an imidazolium carbene-type ligand, and a first base.

26. A process for preparing resveratrol from compounds of Formula 1A3

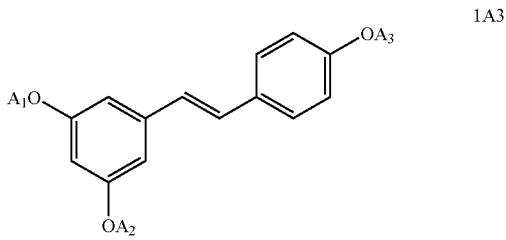

1A3 wherein $A_1$ is selected from: $P_1$ and $(CO)R_1$;

$A_2$ is selected from: $P_2$ and $(CO)R_2$;

$A_3$ is selected from $P_3$ and $(CO)R_3$;

wherein $P_1$ when present is a first alcohol protecting group, $P_2$ when present is a second alcohol protecting group, and $P_3$ when present is a third alcohol protecting group;

$R_1$, $R_2$, and $R_3$ when present are each independently selected from alkyl, aryl, and aralkyl;

comprising the step or steps:
(a) reacting the compounds of Formula 1A3 with a first base; and/or,
(b) reacting the compounds of Formula 1A3 with one or more deprotection reactants to remove the alcohol protecting groups $P_1$, $P_2$ and $P_3$.

27. The process according to claim 26, where $R_1$, $R_2$, and $R_3$ when present are each independently selected from alkyl with at least two carbon atoms, aryl, and aralkyl, and diastereoisomers of the foregoing.

* * * * *